(12) United States Patent
Mitchell et al.

(10) Patent No.: US 6,280,978 B1
(45) Date of Patent: Aug. 28, 2001

(54) METHODS AND COMPOSITIONS FOR USE IN SPLICEOSOME MEDIATED RNA TRANS-SPLICING

(75) Inventors: Lloyd G. Mitchell; Mariano A. Garcia-Blanco, both of Durham, NC (US)

(73) Assignee: Intronn Holdings, LLC, Silver Springs, MD (US)

( * ) Notice: Subject to any disclaimer, the term of this patent is extended or adjusted under 35 U.S.C. 154(b) by 0 days.

(21) Appl. No.: 09/158,863

(22) Filed: Sep. 23, 1998

Related U.S. Application Data

(63) Continuation-in-part of application No. 09/133,717, filed on Aug. 13, 1998, now Pat. No. 6,083,702, which is a continuation-in-part of application No. 09/087,233, filed on May 28, 1998, now abandoned, which is a continuation-in-part of application No. 08/766,354, filed on Dec. 13, 1996, now Pat. No. 6,013,487.
(60) Provisional application No. 60/008,717, filed on Dec. 15, 1995.

(51) Int. Cl.$^7$ .............................. C07H 21/02; C12N 5/10; C12N 15/09; C12P 19/34

(52) U.S. Cl. ................. 435/91.3; 435/91.31; 435/320.1; 435/325; 435/455; 536/23.1

(58) Field of Search ................................. 435/69.1, 91.3, 435/91.31, 320.1, 325, 366, 375, 455; 514/44; 536/23.1, 23.5, 23.7, 24.5, 25.1

(56) References Cited

U.S. PATENT DOCUMENTS

| | | | |
|---|---|---|---|
| 5,498,531 | * | 3/1996 | Jarrell ................................. 435/91.31 |
| 5,641,673 | * | 6/1997 | Haseloff et al. ....................... 435/325 |
| 5,667,969 | * | 9/1997 | Sullenger et al. ......................... 435/6 |
| 5,780,272 | * | 7/1998 | Jarrell ................................. 435/91.31 |
| 5,863,774 | * | 1/1999 | Haseloff et al. .................... 435/172.3 |
| 5,866,384 | * | 2/1999 | Haseloff et al. .................... 435/172.3 |
| 5,874,414 | * | 2/1999 | Haseloff et al. ......................... 514/44 |
| 5,882,907 | * | 3/1999 | Haseloff et al. .................... 435/172.3 |

FOREIGN PATENT DOCUMENTS

| | | |
|---|---|---|
| 9213089 | * | 8/1992 (WO) . |
| 9513379 | * | 5/1995 (WO) . |

OTHER PUBLICATIONS

Konarska, Padgett, and Sharp, Cell, (Aug. 1985), 165–171, "Trans Splicing of mRNA Precursors in Vitro", vol. 42.*
Phillip A. Sharp, Cell (Jul. 1987) , 147–148, Trans Splicing: Variation on a Familiar Theme?, vol. 50.*
Masayori Inouye, Gene, (1988), 25–34, "Antisense RNA: Its Functions and Applications in Gene Gegulation—Review", vol. 72.
Harold M. Weintraub, Scientific American (Jan. 1990), 40–46, "Antisense RNA and DNA".
E. Uhlmann and A. Peyman, Chemical Reviews (Jun. 1990), 543–584, "Antisense Oligonucleotides: A New Therapeutic Principle", vol. 90 No. 4.
M. Vellard et al., Oncogene, (1991), 505–514, "C–mybproto–oncogene: Evidence for Intermolecular Recombination of Coding Sequences", 6.
Vellard et al., Proc. Natl. Acad. Sci. USA, (Apr. 1992), 2511–2515. A Potential Splicing Factor is Encoded by the Opposite Strand of the Transpliced c–myb Exon:, vol. 89.
Hadjduk et al, The American Journal of the Medical Sciences, (Apr. 1992), 258–270, "Molecular Biology of African Trypanosomes: Development of new Strategies to Combat an Old Disease", vol. 303, No. 4.
Linda Bonen, The FASEB Journal, (Jan. 1993), 40–46, "Trans–splicing of Pre–mRNA in Plants, Animals, and Protists", vol. 7.
Richard C. Mulligan, Science, (May 1993), 926–932, "The Basic Science of Gene Therapy", vol. 260.
Purcell and Martin, Journal of Virology, (Nov. 1993), 6365–6378, "Alternative Splicing of Human Immunodeficiencny Virus Type 1 mRNA Modulates Viral Protein Expression, Republication, and Infectivity", vol. 67 No. 11.
Wittop–Koning and Schümperli, Eur. J. Biochem., (1994), "RNAs and Ribonucleoproteins in Recognition and Catalysis", 219:25–42.
Gesteland and Atkins, Cell (Jun. 1994), 801–802, "The RNA World: A Snapshot in Time", vol. 77.
Phillip A. Sharp, Cell, (Jun. 1994), 805–815, "Split Genes and RNA Splicing", vol. 77.
Timothy W. Nilsen, Cell (Jul. 1994), 1–4, "RNA–RNA Interactions in the Splicesome: unraveling the Ties That Bind", vol. 78.
Sullenger and T. Cech, Nature (Oct. 1994), 619–622, "Ribozyme–mediated Repair of Defective mRNA by Targeted Trans–splicing" vol.371.
J. Cohen and M. Hogan, Sicentific American, (Dec. 1994), 76–82, "The New Genetic Medicines".

(List continued on next page.)

*Primary Examiner*—John L. LeGuyader
*Assistant Examiner*—Thomas G. Larson

(57) ABSTRACT

The molecules and methods of the present invention provide a means for in vivo production of a trans-spliced molecule in a selected subset of cells. The pre-trans-splicing molecules of the invention are substrates for a trans-splicing reaction between the pre-trans-splicing molecules and a pre-mRNA which is uniquely expressed in the specific target cells. The in vivo trans-splicing reaction provides a novel mRNA which is functional as mRNA or encodes a protein to be expressed in the target cells. The expression product of the mRNA is a protein of therapeutic value to the cell or host organism a toxin which causes killing of the specific cells or a novel protein not normally present in such cells. The invention further provides PTMs that have been genetically engineered for the identification of exon/intron boundaries of pre-mRNA molecules using an exon tagging method. The PTMs of the invention can also be designed to result in the production of chimeric RNA encoding for peptide affinity purification tags which can be used to purify and identify proteins expressed in a specific cell type.

32 Claims, 27 Drawing Sheets

OTHER PUBLICATIONS

Christoffersen et al. (1995) "Ribozymes as Human Therapeutic Agents" J. Med. Chem. 38:2023–2037.

Crystal, (1995) "Transfer of Genes to Humans: Early Lessons and Obstacles to Success" Science 270:4044.

Eul, Grasessmann and Grasessmann, The EMBO Journal, (1995), 3226–3235, "Experimental Evidence for RNA trans--splicing in Mammalian Cells". vol. 14, No. 13.

Report and Recommendations of the Panel to Access the NIH Investment in Research on Gene Therapy (1995) Orkin and Motalsky, co–chairs, National Institutes of Health.

Stull et al. (1995) "Antigene, Ribozyme and Aptamer Nucleic Acid Drugs: Progress and Prospects" Pharm. Res. 12:465–483.

* cited by examiner

1. PTM+SF:

2. PTM+SF-Py1:

3. PTM+SF-Py2:

EXON 1 OF βHCG6 ↓                    ↓ 1ST CODING NUCLEOTIDE OF DT-A
5'-CAGGGGACGCACCAAGGATGGAGATGTTCCAG-GGCGCTGATGATGTTGTT
GATTCTTCTTAAATC

1. NUCLEOTIDE SEQUENCES OF THE cis-SPLICED PRODUCT (285 bp):

BioLac-TR1
GGCTTTCGCTACCTGGAGAGACGGCCCGCTGATCCTTTGCGAATACGCCCACGCGATGGTAACAGTCTTG

Splice junction
GCCGGTTTCGCTAAATACTGGCAGGCGTTTCGTCAGTATCCCCGTTTACAG/GGCGGCTTCGTCTAATAATG

GGACTGGGTGGATCAGTCGCTGATTAAATATGATGAAAACGGCAACCCTGGTCGGCTTACGGCGGTGATTT

Lac-TR2
TGGCGGATACGCCCGAACGGATCGCCCAGTTCTGTCTCTGGTCTCTGCCGACCGCCACCGCCATCCAG

2. NUCLEOTIDE SEQUENCES OF THE trans-SPLICED PRODUCT (195 bp):

BioLac-TR1
GGCTTTCGCTACCTGGAGAGACGGCCCGCTGATCCTTTGCGAATACGCCCACGCGATGGTAACAGTCTTGG

Splice junction
CGGTTTCGCTAAATACTGGCAGGCGTTTCGTCAGTATCCCCGTTTACAG/GGGCTGCTGCTGTTGCTGCTGCT

HCGR2
GAGCATGGGGGGGACATGGGCATCCAAGGAGGCCACTTCGGCCACGGTGCCG

FIG.12B

CFTR Pre-therapeutic molecule (PTM or "bullet")

CFTR mini-gene target-construction

Trans-splicing Repair

SEQUENCE LISTING

```
<160> NUMBER OF SEQ ID NOS: 68

<210> SEQ ID NO: 1
<211> LENGTH: 132
<212> TYPE: DNA
<213> ORGANISM: Homo sapiens

<400> SEQUENCE: 1
caggggacgc accaaggatg gagatgttcc agggcgctga tgatgttgtt gattcttctt      60
aaatcttttg tgatggaaaa cttttcttcg taccacggga ctaaacctgg ttatgtagat     120
tccattcaaa aa                                                         132

<210> SEQ ID NO: 2
<211> LENGTH: 29
```

```
<212> TYPE: DNA
<213> ORGANISM: Corynebacterium diptheriae

<400> SEQUENCE: 2
ggcgctgcag ggcgctgatg atgttgttg                                29

<210> SEQ ID NO: 3
<211> LENGTH: 36
<212> TYPE: DNA
<213> ORGANISM: Corynebacterium diptheriae

<400> SEQUENCE: 3
ggcgaagctt ggatccgaca cgatttcctg cacagg                        36

<210> SEQ ID NO: 4
<211> LENGTH: 68
<212> TYPE: DNA
<213> ORGANISM: Artificial Sequence
<220> FEATURE:
<223> OTHER INFORMATION: oligonucleotide

<400> SEQUENCE: 4
aattctctag atgcttcacc cgggcctgac tcgagtacta actggtacct cttctttttt    60
ttcctgca                                                       68

<210> SEQ ID NO: 5
<211> LENGTH: 60
<212> TYPE: DNA
<213> ORGANISM: Artificial Sequence
<220> FEATURE:
<223> OTHER INFORMATION: oligonucleotide

<400> SEQUENCE: 5
ggaaaaaaaa gaagaggtac cagttagtac tcgagtcagg cccgggtgaa gcatctagag    60

<210> SEQ ID NO: 6
<211> LENGTH: 24
<212> TYPE: DNA
<213> ORGANISM: Artificial Sequence
<220> FEATURE:
<223> OTHER INFORMATION: oligonucleotide

<400> SEQUENCE: 6
tcgagcaacg ttataataat gttc                                     24

<210> SEQ ID NO: 7
<211> LENGTH: 24
<212> TYPE: DNA
<213> ORGANISM: Artificial Sequence
<220> FEATURE:
<223> OTHER INFORMATION: oligonucleotide

<400> SEQUENCE: 7
tcgagaacat tattataacg ttgc                                     24

<210> SEQ ID NO: 8
<211> LENGTH: 35
<212> TYPE: DNA
<213> ORGANISM: Artificial Sequence
<220> FEATURE:
<223> OTHER INFORMATION: oligonucleotide

<400> SEQUENCE: 8
aattctctag atcaggcccg ggtgaagcac tcgag                         35
```

```
<210> SEQ ID NO: 9
<211> LENGTH: 25
<212> TYPE: DNA
<213> ORGANISM: Artificial Sequence
<220> FEATURE:
<223> OTHER INFORMATION: oligonucleotide

<400> SEQUENCE: 9
tgcttcaccc gggcctgatc tagag                                    25

<210> SEQ ID NO: 10
<211> LENGTH: 18
<212> TYPE: DNA
<213> ORGANISM: Homo sapiens

<400> SEQUENCE: 10
tgcttcaccc gggcctga                                            18

<210> SEQ ID NO: 11
<211> LENGTH: 16
<212> TYPE: DNA
<213> ORGANISM: Homo sapiens

<400> SEQUENCE: 11
ctcttctttt ttttcc                                              16

<210> SEQ ID NO: 12
<211> LENGTH: 18
<212> TYPE: DNA
<213> ORGANISM: Homo sapiens

<400> SEQUENCE: 12
caacgttata ataatgtt                                            18

<210> SEQ ID NO: 13
<211> LENGTH: 16
<212> TYPE: DNA
<213> ORGANISM: Homo sapiens

<400> SEQUENCE: 13
ctgtgattaa tagcgg                                              16

<210> SEQ ID NO: 14
<211> LENGTH: 16
<212> TYPE: DNA
<213> ORGANISM: Homo sapiens

<400> SEQUENCE: 14
cctggacgcg gaagtt                                              16

<210> SEQ ID NO: 15
<211> LENGTH: 51
<212> TYPE: DNA
<213> ORGANISM: Homo sapiens

<400> SEQUENCE: 15
ctgggacaag gacactgctt cacccggtta gtagaccaca gccctgaagc c        51

<210> SEQ ID NO: 16
<211> LENGTH: 17
<212> TYPE: DNA
<213> ORGANISM: Homo sapiens

<400> SEQUENCE: 16
```

-continued

```
cttctgtttt ttttctc                                              17

<210> SEQ ID NO: 17
<211> LENGTH: 16
<212> TYPE: DNA
<213> ORGANISM: Homo sapiens

<400> SEQUENCE: 17
cttctgtatt attctc                                               16

<210> SEQ ID NO: 18
<211> LENGTH: 16
<212> TYPE: DNA
<213> ORGANISM: Homo sapiens

<400> SEQUENCE: 18
gttctgtcct tgtctc                                               16

<210> SEQ ID NO: 19
<211> LENGTH: 29
<212> TYPE: DNA
<213> ORGANISM: Corynebacterium diptheriae

<400> SEQUENCE: 19
ggcgctgcag ggcgctgatg atgttgttg                                 29

<210> SEQ ID NO: 20
<211> LENGTH: 36
<212> TYPE: DNA
<213> ORGANISM: Corynebacterium diptheriae

<400> SEQUENCE: 20
ggcgaagctt ggatccgaca cgatttcctg cacagg                         36

<210> SEQ ID NO: 21
<211> LENGTH: 21
<212> TYPE: DNA
<213> ORGANISM: Corynebacterium diptheriae

<400> SEQUENCE: 21
catcgtcata atttccttgt g                                         21

<210> SEQ ID NO: 22
<211> LENGTH: 20
<212> TYPE: DNA
<213> ORGANISM: Corynebacterium diptheriae

<400> SEQUENCE: 22
atggaatcta cataaccagg                                           20

<210> SEQ ID NO: 23
<211> LENGTH: 20
<212> TYPE: DNA
<213> ORGANISM: Corynebacterium diptheriae

<400> SEQUENCE: 23
gaaggctgag cactacacgc                                           20

<210> SEQ ID NO: 24
<211> LENGTH: 20
<212> TYPE: DNA
<213> ORGANISM: Homo sapiens
```

```
<400> SEQUENCE: 24
cggcaccgtg gccgaagtgg                                          20

<210> SEQ ID NO: 25
<211> LENGTH: 30
<212> TYPE: DNA
<213> ORGANISM: Homo sapiens

<400> SEQUENCE: 25
accggaattc atgaagccag gtacaccagg                               30

<210> SEQ ID NO: 26
<211> LENGTH: 20
<212> TYPE: DNA
<213> ORGANISM: Homo sapiens

<400> SEQUENCE: 26
gggcaaggtg aacgtggatg                                          20

<210> SEQ ID NO: 27
<211> LENGTH: 19
<212> TYPE: DNA
<213> ORGANISM: Homo sapiens

<400> SEQUENCE: 27
atcaggagtg gacagatcc                                           19

<210> SEQ ID NO: 28
<211> LENGTH: 39
<212> TYPE: DNA
<213> ORGANISM: Artificial Sequence
<220> FEATURE:
<223> OTHER INFORMATION: Oligonucleotide primer complimentary to the
      Escherichia coli lacZ gene

<400> SEQUENCE: 28
gcatgaattc ggtaccatgg gggggttctc atcatcatc                     39

<210> SEQ ID NO: 29
<211> LENGTH: 36
<212> TYPE: DNA
<213> ORGANISM: Artificial Sequence
<220> FEATURE:
<223> OTHER INFORMATION: Oligonucleotide primer complimentary to the
      Escherichia coli lacZ gene

<400> SEQUENCE: 29
ctgaggatcc tcttacctgt aaacgcccat actgac                        36

<210> SEQ ID NO: 30
<211> LENGTH: 38
<212> TYPE: DNA
<213> ORGANISM: Artificial Sequence
<220> FEATURE:
<223> OTHER INFORMATION: Oligonucleotide primer complimentary to the
      Escherichia coli lacZ gene

<400> SEQUENCE: 30
gcatggtaac cctgcagggc ggcttcgtct gggactgg                      38

<210> SEQ ID NO: 31
<211> LENGTH: 38
<212> TYPE: DNA
<213> ORGANISM: Artificial Sequence
<220> FEATURE:
```

<223> OTHER INFORMATION: Oligonucleotide primer complimentary to the
      Escherichia coli lacZ gene

<400> SEQUENCE: 31
ctgaaagctt gttaacttat tatttttgac accagacc                              38

<210> SEQ ID NO: 32
<211> LENGTH: 47
<212> TYPE: DNA
<213> ORGANISM: Artificial Sequence
<220> FEATURE:
<223> OTHER INFORMATION: Oligonucleotide primer complimentary to the
      Escherichia coli lacZ gene

<400> SEQUENCE: 32
gcatggtaac cctgcagggc ggcttcgtct aataatggga ctgggtg                    47

<210> SEQ ID NO: 33
<211> LENGTH: 37
<212> TYPE: DNA
<213> ORGANISM: Artificial Sequence
<220> FEATURE:
<223> OTHER INFORMATION: Oligonucleotide primers complimentary to beta
      HCG6 gene (accession #X00266)

<400> SEQUENCE: 33
gcatggatcc tccggagggc ccctgggcac cttccac                               37

<210> SEQ ID NO: 34
<211> LENGTH: 38
<212> TYPE: DNA
<213> ORGANISM: Artificial Sequence
<220> FEATURE:
<223> OTHER INFORMATION: Oligonucleotide primers complimentary to beta
      HCG6 gene (accession #X00266)

<400> SEQUENCE: 34
ctgactgcag ggtaaccgga caaggacact gcttcacc                              38

<210> SEQ ID NO: 35
<211> LENGTH: 35
<212> TYPE: DNA
<213> ORGANISM: Artificial Sequence
<220> FEATURE:
<223> OTHER INFORMATION: Oligonucleotide primers complimentary to beta
      HCG6 gene (accession #X00266)

<400> SEQUENCE: 35
gcatggtaac cctgcagggg ctgctgctgt tgctg                                 35

<210> SEQ ID NO: 36
<211> LENGTH: 37
<212> TYPE: DNA
<213> ORGANISM: Artificial Sequence
<220> FEATURE:
<223> OTHER INFORMATION: Oligonucleotide primers complimentary to beta
      HCG6 gene (accession #X00266)

<400> SEQUENCE: 36
ctgaaagctt gttaaccagc tcaccatggt ggggcag                               37

<210> SEQ ID NO: 37
<211> LENGTH: 22
<212> TYPE: DNA
<213> ORGANISM: Artificial Sequence
<220> FEATURE:
<223> OTHER INFORMATION: Oligonucleotide primer complimentary to the Escherichia coli lacZ gene

<400> SEQUENCE: 37
ggctttcgct acctggagag ac                                               22

<210> SEQ ID NO: 38
<211> LENGTH: 21
<212> TYPE: DNA
<213> ORGANISM: Artificial Sequence
<220> FEATURE:
<223> OTHER INFORMATION: Oligonucleotide primer complimentary to the
      Escherichia coli lacZ gene

<400> SEQUENCE: 38
gctggatgcg gcgtgcggtc g                                                21

<210> SEQ ID NO: 39
<211> LENGTH: 20
<212> TYPE: DNA
<213> ORGANISM: Artificial Sequence
<220> FEATURE:
<223> OTHER INFORMATION: Oligonucleotide primers complimentary to beta
      HCG6 gene (accession #X00266)

<400> SEQUENCE: 39
cggcaccgtg gccgaagtgg                                                  20

<210> SEQ ID NO: 40
<211> LENGTH: 45
<212> TYPE: DNA
<213> ORGANISM: Homo sapiens

<400> SEQUENCE: 40
acctgggccc acccattatt aggtcattat ccgcggaaca ttata                      45

<210> SEQ ID NO: 41
<211> LENGTH: 35
<212> TYPE: DNA
<213> ORGANISM: Homo sapiens

<400> SEQUENCE: 41
acctctgcag gtgaccctgc aggaaaaaaa agaag                                 35

<210> SEQ ID NO: 42
<211> LENGTH: 30
<212> TYPE: DNA
<213> ORGANISM: Homo sapiens

<400> SEQUENCE: 42
acctctgcag acttcacttc taatgatgat                                       30

<210> SEQ ID NO: 43
<211> LENGTH: 51
<212> TYPE: DNA
<213> ORGANISM: Homo sapiens

<400> SEQUENCE: 43
acctgcggcc gcctaatgat gatgatgatg atgctcttct agttggcatg c               51

<210> SEQ ID NO: 44
<211> LENGTH: 32
<212> TYPE: DNA
<213> ORGANISM: Homo sapiens

<400> SEQUENCE: 44

```
gacctctcga gggatttggg gaattatttg ag                    32

<210> SEQ ID NO: 45
<211> LENGTH: 35
<212> TYPE: DNA
<213> ORGANISM: Homo sapiens

<400> SEQUENCE: 45
ctgacctgcg gccgctacag tgttgaatgt ggtgc                 35

<210> SEQ ID NO: 46
<211> LENGTH: 35
<212> TYPE: DNA
<213> ORGANISM: Homo sapiens

<400> SEQUENCE: 46
ctgacctgcg gccgcccaac tatctgaatc atgtg                 35

<210> SEQ ID NO: 47
<211> LENGTH: 32
<212> TYPE: DNA
<213> ORGANISM: Homo sapiens

<400> SEQUENCE: 47
gacctcttaa gtagactaac cgattgaata tg                    32

<210> SEQ ID NO: 48
<211> LENGTH: 21
<212> TYPE: DNA
<213> ORGANISM: Homo sapiens

<400> SEQUENCE: 48
ctaatgatga tgatgatgat g                                21

<210> SEQ ID NO: 49
<211> LENGTH: 21
<212> TYPE: DNA
<213> ORGANISM: Homo sapiens

<400> SEQUENCE: 49
cgcctaatga tgatgatgat g                                21

<210> SEQ ID NO: 50
<211> LENGTH: 21
<212> TYPE: DNA
<213> ORGANISM: Homo sapiens

<400> SEQUENCE: 50
cttcttggta ctcctgtcct g                                21

<210> SEQ ID NO: 51
<211> LENGTH: 32
<212> TYPE: DNA
<213> ORGANISM: Homo sapiens

<400> SEQUENCE: 51
gacctctcga gggatttggg gaattatttg ag                    32

<210> SEQ ID NO: 52
<211> LENGTH: 21
<212> TYPE: DNA
<213> ORGANISM: Homo sapiens
```

-continued

<400> SEQUENCE: 52
aactagaagg cacagtcgag g                                            21

<210> SEQ ID NO: 53
<211> LENGTH: 24
<212> TYPE: DNA
<213> ORGANISM: Artificial Sequence
<220> FEATURE:
<223> OTHER INFORMATION: trans-spliced product containing Human
      chorionic gonadotropin gene 6 sequences and Corynebacterium
      diphtheriae diphtheria toxin A sequences

<400> SEQUENCE: 53
gagatgttcc agggcgtgat gatg                                         24

<210> SEQ ID NO: 54
<211> LENGTH: 125
<212> TYPE: RNA
<213> ORGANISM: Artificial Sequence
<220> FEATURE:
<223> OTHER INFORMATION: PTM intramolecular base-paired stem
<221> NAME/KEY: misc_feature
<222> LOCATION: (57)...(70)
<223> OTHER INFORMATION: Loop comprising a combination of 14 nucleotides
      according to the specification

<400> SEQUENCE: 54
gcuagccugg gacaaggaca cugcuucacc cgguuaguag accacagccc ugagccnnnn    60
nnnnnnnnnn aucguuaacu aauaaacuac uaacuaacug ggugaauguu uuucucggc    120 ugcag                                                              125

<210> SEQ ID NO: 55
<211> LENGTH: 127
<212> TYPE: RNA
<213> ORGANISM: Artificial Sequence
<220> FEATURE:
<223> OTHER INFORMATION: PTM intramolecular base-paired stem
<221> NAME/KEY: misc_feature
<222> LOCATION: (57)...(70)
<223> OTHER INFORMATION: Loop comprising a combination of 14 nucleotides
      according to the specification

<400> SEQUENCE: 55
gcuagccugg gacaaggaca cugcuucacc cgguuaguag accacagccc ugagccnnnn    60
nnnnnnnnnn aucguuaacu aauaaacuac uaacugggug aacuucugua uuauucga    120 gcugcag                                                            127

<210> SEQ ID NO: 56
<211> LENGTH: 127
<212> TYPE: RNA
<213> ORGANISM: Artificial Sequence
<220> FEATURE:
<223> OTHER INFORMATION: PTM intramolecular base-paired stem
<221> NAME/KEY: misc_feature
<222> LOCATION: (57)...(70)
<223> OTHER INFORMATION: Loop comprising a combination of 14 nucleotides
      according to the specification

<400> SEQUENCE: 56
gcuagccugg gacaaggaca cugcuucacc cgguuaguag accacagccc ugagccnnnn    60
nnnnnnnnnn aucguuaacu aauaaacuac uaacuggguc aaguucuguc cuugucucga   120
gcugcag                                                            127

```
<210> SEQ ID NO: 57
<211> LENGTH: 132
<212> TYPE: DNA
<213> ORGANISM: Artificial Sequence
<220> FEATURE:
<223> OTHER INFORMATION: trans-spliced product containing Human
      chorionic gonadotropin gene 6 sequences and Corynebacterium
      diphtheriae diphtheria toxin A sequences

<400> SEQUENCE: 57
caggggacgc accaaggatg gagatgttcc agggcgctga tgatgttgtt gattcttctt       60
aaatcttttg tgatggaaaa cttttcttcg taccacggga ctaaacctgg ttatgtagat      120
tccattcaaa aa                                                          132

<210> SEQ ID NO: 58
<211> LENGTH: 18
<212> TYPE: DNA
<213> ORGANISM: Artificial Sequence
<220> FEATURE:
<223> OTHER INFORMATION: Artificial sequence comprising sequences
      derived from Escherichia coli lacZ gene

<400> SEQUENCE: 58
gaattcggta ccatgggg                                                     18

<210> SEQ ID NO: 59
<211> LENGTH: 33
<212> TYPE: DNA
<213> ORGANISM: Artificial Sequence
<220> FEATURE:
<223> OTHER INFORMATION: Artificial sequence comprising sequences
      derived from Escherichia coli lacZ gene and human
      chorionic gonadotropin gene 6 intron 1

<400> SEQUENCE: 59
cgtttacagg taagaggatc ctccggaggg ccc                                    33

<210> SEQ ID NO: 60
<211> LENGTH: 30
<212> TYPE: DNA
<213> ORGANISM: Artificial Sequence
<220> FEATURE:
<223> OTHER INFORMATION: Artificial sequence comprising sequences
      derived from Escherichia coli lacZ gene

<400> SEQUENCE: 60
tggtgtcaaa aataataagt taacaagctt                                        30

<210> SEQ ID NO: 61
<211> LENGTH: 25
<212> TYPE: DNA
<213> ORGANISM: Artificial Sequence
<220> FEATURE:
<223> OTHER INFORMATION: trans-spliced product containing Escherichia
      coli lacZ gene sequences and human chorionic
      gonadotropin gene 6 exon 2 sequences

<400> SEQUENCE: 61
cagcagcccc tgtaaacggg gatac                                             25

<210> SEQ ID NO: 62
<211> LENGTH: 286
<212> TYPE: DNA
<213> ORGANISM: Artificial Sequence
<220> FEATURE:
<223> OTHER INFORMATION: trans-spliced product containing Escherichia
      coli lacZ gene sequences
```

<400> SEQUENCE: 62

```
ggctttcgct acctggagag acgcgcccgc tgatcctttg cgaatacgcc cacgcgatgg      60
gtaacagtct tggcggtttc gctaaatact ggcaggcgtt tcgtcagtat ccccgtttac     120
agggcggctt cgtctaataa tgggactggg tggatcagtc gctgattaaa tatgatgaaa     180
acgggcaacc cgtggtcggc ttacggcggt gattttggcg atacgccgaa cgatcgccag     240
ttctgtatga acggtctggt ctttgccgac cgcacgccgc atccag                    286
```

<210> SEQ ID NO: 63
<211> LENGTH: 196
<212> TYPE: DNA
<213> ORGANISM: Artificial Sequence
<220> FEATURE:
<223> OTHER INFORMATION: trans-spliced product containing Escherichia
    coli lacZ gene sequences and human chorionic
    gonadotropin gene 6 exon 2 sequences

<400> SEQUENCE: 63

```
ggctttcgct acctggagag acgcgcccgc tgatcctttg cgaatacgcc cacgcgatgg      60
gtaacagtct tggcggtttc gctaaatact ggcaggcgtt tcgtcagtat ccccgtttac     120
aggggctgct gctgttgctg ctgctgagca tgggcgggac atgggcatcc aaggagccac     180
ttcggccacg gtgccg                                                     196
```

<210> SEQ ID NO: 64
<211> LENGTH: 420
<212> TYPE: DNA
<213> ORGANISM: Artificial Sequence
<220> FEATURE:
<223> OTHER INFORMATION: trans-spliced product comprising cystic
    fibrosis transmembrane regulator-derived sequences and His
    tag sequences

<400> SEQUENCE: 64

```
gctagcgttt aaacgggccg acccatcatt attaggtcat tatccgcgga acattattat      60
aacgttgctc gagtactaac tggaacctct tcttttttt cctgcagact tcacttctaa     120
tgatgattat gggagaactg gagccttcag agggtaaaat taagcacagt ggaagaattt     180
cattctgttc tcagttttcc tggattatgc ctggcaccat taaagaaaat atcatctttg     240
gcggccgcca ctgtgctgga tatctgcaga attccaccac actggactag tggatccgag     300
ctcggtacca aggttaagtt taaaccgctg atcagcctcg actgtgcctt ctagttgcca     360
gccatctgtt gtttgcccct cccccgtgcc ttccttgacc ctggaaggtg ccactcccac     420
```

<210> SEQ ID NO: 65
<211> LENGTH: 20
<212> TYPE: DNA
<213> ORGANISM: Artificial Sequence
<220> FEATURE:
<223> OTHER INFORMATION: Splice junction sequence

<400> SEQUENCE: 65

```
atgttccagg gcgtgatgat                                                  20
```

<210> SEQ ID NO: 66
<211> LENGTH: 7
<212> TYPE: PRT
<213> ORGANISM: Artificial Sequence
<220> FEATURE:
<223> OTHER INFORMATION: C terminal residues of
    glutathione-S-transferase

```
<400> SEQUENCE: 66

Asp Tyr Lys Asp Asp Asp Lys
 1               5

<210> SEQ ID NO: 67
<211> LENGTH: 15
<212> TYPE: DNA
<213> ORGANISM: Artificial Sequence
<220> FEATURE:
<223> OTHER INFORMATION: Artificial sequence comprising sequences
      derived from Escherichia coli lacZ gene

<400> SEQUENCE: 67
ggagttgatc ccgtc                                                    15

<210> SEQ ID NO: 68
<211> LENGTH: 37
<212> TYPE: DNA
<213> ORGANISM: Artificial Sequence
<220> FEATURE:
<223> OTHER INFORMATION: Artificial sequence comprising sequences
      derived from Escherichia coli lacZ gene and human
      chorionic gonadotropin gene 6 intron 1

<400> SEQUENCE: 68
gcagtgtcct tgtgcggtta ccctgcaggg cggcttc                            37
```

METHODS AND COMPOSITIONS FOR USE IN SPLICEOSOME MEDIATED RNA TRANS-SPLICING

The present application is a continuation-in-part of application Ser. No. 09/133,717, filed on Aug. 13, 1998, now U.S. Pat. No. 6,083,702 which is a continuation-in-part of Ser. No. 09/087,233, filed on May 28, 1998, now abandoned, which is a continuation-in-part of application Ser. No. 08/766,354 filed on Dec. 13, 1996, now U.S. Pat. No. 6,013,487, which claims benefit to provisional application No. 60/008,717 filed on Dec. 15, 1995.

INTRODUCTION

The present invention provides methods and compositions for generating novel nucleic acid molecules through targeted spliceosomal trans-splicing. The compositions of the invention include pre-trans-splicing molecules (PTMs) designed to interact with a natural target precursor messenger RNA molecule (target pre-mRNA) and mediate a trans-splicing reaction resulting in the generation of a novel chimeric RNA molecule (chimeric RNA). The PTMs of the invention are genetically engineered so as to result in the production of a novel chimeric RNA which may itself perform a function, such as inhibiting the translation of the RNA, or that encodes a protein that complements a defective or inactive protein in a cell, or encodes a toxin which kills specific cells. Generally, the target pre-mRNA is chosen as a target because it is expressed within a specific cell type thus providing a means for targeting expression of the novel chimeric RNA to a selected cell type. The invention further relates to PTMs that have been genetically engineered for the identification of exon/intron boundaries of pre-mRNA molecules using an exon tagging method. In addition, PTMs can be designed to result in the production of chimeric RNA encoding for peptide affinity purification tags which can be used to purify and identify proteins expressed in a specific cell type. The methods of the invention encompass contacting the PTMs of the invention with a target pre-mRNA under conditions in which a portion of the PTM is trans-spliced to a portion of the target pre-mRNA to form a novel chimeric RNA molecule. The methods and compositions of the invention can be used in cellular gene regulation, gene repair and suicide gene therapy for treatment of proliferative disorders such as cancer or treatment of genetic, autoimmune or infectious diseases. The methods and compositions of the invention can also be used to map intron-exon boundaries and to identify novel proteins expressed in any given cell.

BACKGROUND OF THE INVENTION

DNA sequences in the chromosome are transcribed into pre-mRNAs which contain coding regions (exons) and generally also contain intervening non-coding regions (introns). Introns are removed from pre-mRNAs in a precise process called splicing (Chow et al., 1977, Cell 12:1–8; and Berget, S. M. et al., 1977, Proc. Natl. Acad. Sci. USA 74:3171–3175). Splicing takes place as a coordinated interaction of several small nuclear ribonucleoprotein particles (snRNP's) and many protein factors that assemble to form an enzymatic complex known as the spliceosome (Moore et al., 1993, in The RNA World, R. F. Gestland and J. F. Atkins eds. (Cold Spring Harbor Laboratory Press, Cold Spring Harbor, N.Y.); Kramer, 1996, Annu. Rev. Biochem., 65:367–404; Staley and Guthrie, 1998, Cell 92:315–326).

Pre-mRNA splicing proceeds by a two-step mechanism. In the first step, the 5' splice site is cleaved, resulting in a "free" 5' exon and a lariat intermediate (Moore, M. J. and P. A. Sharp, 1993, Nature 365:364–368). In the second step, the 5' exon is ligated to the 3' exon with release of the intron as the lariat product. These steps are catalyzed in a complex of small nuclear ribonucleoproteins and proteins called the spliceosome.

The splicing reaction sites are defined by consensus sequences around the 5' and 3' splice sites. The 5' splice site consensus sequence is AG/GURAGU (where A=adenosine, U=uracil, G=guanine, C=cytosine, R=purine and/=the splice site). The 3' splice region consists of three separate sequence elements: the branch point or branch site, a polypyrimidine tract and the 3' splice consensus sequence (YAG). These elements loosely define a 3' splice region, which may encompass 100 nucleotides of the intron upstream of the 3' splice site. The branch point consensus sequence in mammals is YNYUR<u>A</u>C (where N=any nucleotide, Y=pyrimidine). The underlined A is the site of branch formation (the BPA=branch point adenosine). The 3' splice consensus sequence is YAG/G. Between the branch point and the splice site there is usually found a polypyrimidine tract, which is important in mammalian systems for efficient branch point utilization and 3' splice site recognition (Roscigno, R., F. et al., 1993, J. Biol. Chem. 268:11222–11229). The first YAG trinucleotide downstream from the branch point and polypyrimidine tract is the most commonly used 3' splice site (Smith, C. W. et al., 1989, Nature 342:243–247).

In most cases, the splicing reaction occurs within the same pre-mRNA molecule, which is termed cis-splicing. Splicing between two independently transcribed pre-mRNAs is termed trans-splicing). Trans-splicing was first discovered in trypanosomes (Sutton & Boothroyd, 1986, Cell 47:527; Murphy et al., 1986, Cell 47:517) and subsequently in nematodes (Krause & Hirsh, 1987, Cell 49:753); flatworms (Rajkovic et al., 1990, Proc. Nat'l. Acad. Sci. USA, 87:8879; Davis et al., 1995, J. Biol. Chem. 270:21813) and in plant mitochondria (Malek et al., 1997, Proc. Nat'l. Acad. Sci. USA 94:553). In the parasite *Trypanosoma brucei,* all mRNAs acquire a splice leader (SL) RNA at their 5' termini by trans-splicing. A 5' leader sequence is also trans-spliced onto some genes in *Caenorhabditis elegans.* This mechanism is appropriate for adding a single common sequence to many different transcripts.

The mechanism of trans-splicing, which is nearly identical to that of conventional cis-splicing, proceeds via two phosphoryl transfer reactions. The first causes the formation of a 2'–5' phosphodiester bond producing a 'Y' shaped branched intermediate, equivalent to the lariat intermediate in cis-splicing. The second reaction, exon ligation, proceeds as in conventional cis-splicing. In addition, sequences at the 3' splice site and some of the snRNPs which catalyze the trans-splicing reaction, closely resemble their counterparts involved in cis-splicing.

Trans-splicing may also refer to a different process, where an intron of one pre-mRNA interacts with an intron of a second pre-mRNA, enhancing the recombination of splice sites between two conventional pre-mRNAs. This type of trans-splicing was postulated to account for transcripts encoding a human immunoglobulin variable region sequence linked to the endogenous constant region in a transgenic mouse (Shimizu et al.,1989, Proc. Nat'l. Acad. Sci. USA 86:8020). In addition, trans-splicing of c-myb pre-RNA has been demonstrated (Vellard, M. et al. Proc. Nat'l. Acad. Sci. 89:2511–2515) and more recently, RNA transcripts from cloned SV40 trans-spliced to each other were detected in cultured cells and nuclear extracts (Eul et al., 1995, EMBO. J. 14:3226). However, naturally occurring trans-splicing of mammalian pre-mRNAs is thought to be an exceedingly rare event. The reaction mechanism of trans-splicing is believed to be nearly identical to conventional cis-splicing. It proceeds via the formation of a 2'-5' phosphodiester bond producing a 'Y' shaped branched intermediate (equivalent to the lariat intermediated in cis-splicing).

In vitro trans-splicing has been used as a model system to examine the mechanism of splicing by several groups (Konarska & Sharp, 1985, Cell 46:165–171 Solnick, 1985, Cell 42:157; Chiara & Reed, 1995, Nature 375:510; Pasman and Garcia-Blanco, 1996, Nucleic Acids Res. 24:1638). Reasonably efficient trans-splicing (30% of cis-spliced analog) was achieved between RNAs capable of base pairing to each other, splicing of RNAs not tethered by base pairing was further diminished by a factor of 10. Other in vitro trans-splicing reactions not requiring obvious RNA-RNA interactions among the substrates were observed by Chiara & Reed (1995, Nature 375:510), Bruzik J. P. & Maniatis, T. (1992, Nature 360:692) and (Bruzik J. P. and Maniatis, T., 1995, Proc. Nat'l. Acad. Sci. USA 92:7056–7059). These reactions occur at relatively low frequencies and require specialized elements, such as a downstream 5' splice site or exonic splicing enhancers.

In addition to splicing mechanisms involving the binding of multiple proteins to the precursor mRNA which then act to correctly cut and join RNA, a third mechanism involves cutting and joining of the RNA by the intron itself, by what are termed catalytic RNA molecules or ribozymes. The cleavage activity of ribozymes has been targeted to specific RNAs by engineering a discrete "hybridization" region into the ribozyme. Upon hybridization to the target RNA, the catylytic region of the ribozyme cleaves the target. It has been suggested that such ribozyme activity would be useful for the inactivation or cleavage of target RNA in vivo, such as for the treatment of human diseases characterized by production of foreign of aberrant RNA. The use of antisense RNA has also been proposed as an alternative mechanism for targeting and destruction of specific RNAs. In such instances small RNA molecules are designed to hybridize to the target RNA and by binding to the target RNA prevent translation of the target RNA or cause destruction of the RNA through activation of nucleases.

Until recently, the practical application of targeted trans-splicing to modify specific target genes has been limited to group I ribozyme-based mechanisms. Using the Tetrahymena group I ribozyme, targeted trans-splicing was demonstrated in *E. coli. coli* (Sullengen B. A. and Cech. T. R., 1994, Nature 341:619–622), in mouse fibroblasts (Jones, J. T. et al., 1996, Nature Medicine 2:643–648), human fibroblasts (Phylacton, L. A. et al. Nature Genetics 18:378–381) and human erythroid precursors (Lan et al., 1998, Science 280:1593–1596). While many applications of targeted RNA trans-splicing driven by modified group I ribozymes have been explored, targeted trans-splicing mediated by native mammalian splicing machinery, i.e., spliceosomes, has not been previously reported.

SUMMARY OF THE INVENTION

The present invention relates to compositions and methods for generating novel nucleic acid molecules through spliceosome-mediated targeted trans-splicing. The compositions of the invention include pre-trans-splicing molecules (hereinafter referred to as "PTMs") designed to interact with a natural target pre-mRNA molecule (hereinafter referred to as "pre-mRNA") and mediate a spliceosomal trans-splicing reaction resulting in the generation of a novel chimeric RNA molecule (hereinafter referred to as "chimeric RNA"). The methods of the invention encompass contacting the PTMs of the invention with a natural target pre-mRNA under conditions in which a portion of the PTM is spliced to the natural pre-mRNA to form a novel chimeric RNA. The PTMs of the invention are genetically engineered so that the novel chimeric RNA resulting from the trans-splicing reaction may itself perform a function such as inhibiting the translation of RNA, or alternatively, the chimeric RNA may encode a protein that complements a defective or inactive protein in the cell, or encodes a toxin which kills the specific cells. Generally, the target pre-mRNA is chosen because it is expressed within a specific cell type thereby providing a means for targeting expression of the novel chimeric RNA to a selected cell type. The target cells may include, but are not limited to those infected with viral or other infectious agents, benign or malignant neoplasms, or components of the immune system which are involved in autoimmune disease or tissue rejection. The PTMs of the invention can also be genetically engineered to tag exon sequences in a mRNA molecule as a method for identifying intron/exon boundaries in target pre-mRNA. The invention further relates to the use of PTM molecules that are genetically engineered to encode a peptide affinity purification tag for use in the purification and identification of proteins expressed in a specific cell type. The methods and compositions of the invention can be used in gene regulation, gene repair and targeted cell death. Such methods and compositions can be used for the treatment of various diseases including, but not limited to, genetic, infectious or autoimmune diseases and proliferative disorders such as cancer.

Figure 1A:
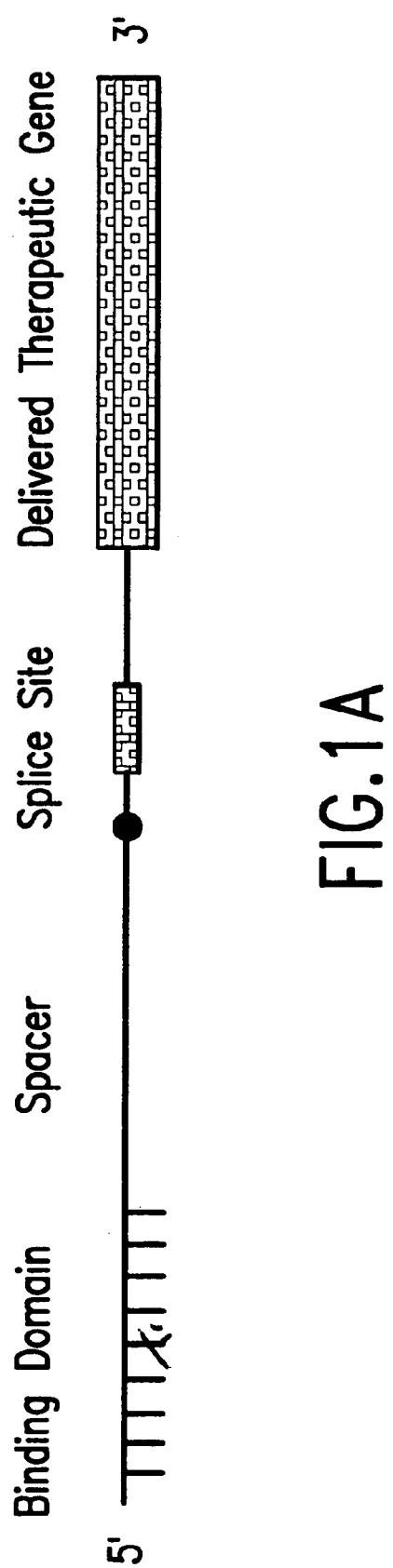
FIG. 1A. Model of Pre-Trans-splicing RNA.
Figure 1B:
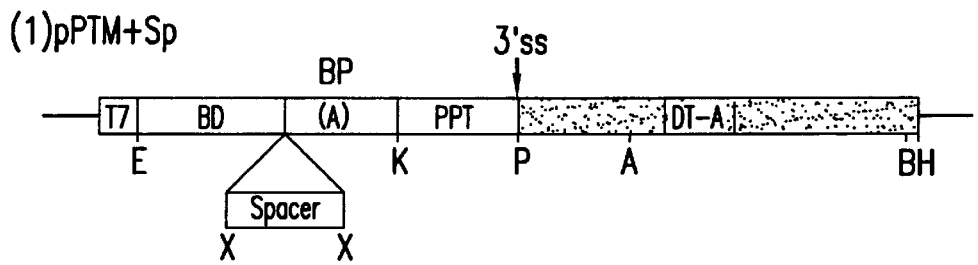
FIG. 1B. Model PTM constructs and targeted trans-splicing strategy. Schematic representation of the first generation PTMs (PTM+Sp and PTM–Sp). BD, binding domain; NBD, non-binding domain; BP, branch point; PPT, pyrimidine tract; ss, splice site and DT-A, diphtheria toxin subunit A. Unique restriction sites within the PTMS are indicated by single letters: *E. coli*, EcoRI; X, Xhol; K, Kpnl; P, Pstl; A, Accl; B, BamHI and Heterologous, HindIII.
Figure 1B:
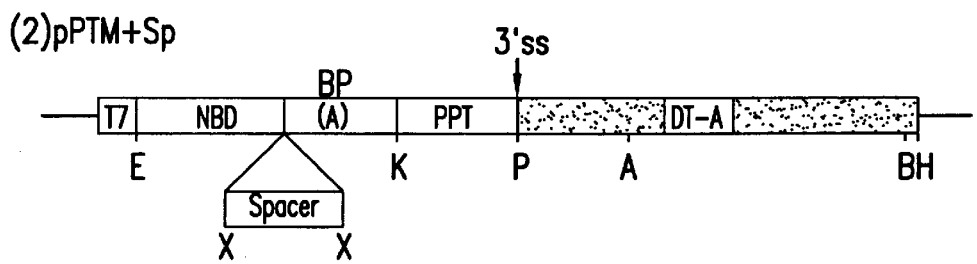

The methods of the invention encompass contacting the PTMs of the invention with a natural pre-mRNA under conditions in which a portion of the PTM is trans-spliced to a portion of the natural pre-mRNA to form a novel chimeric RNA. The target pre-mRNA is chosen as a target due to its expression within a specific cell type thus providing a mechanism for targeting expression of a novel RNA to a selected cell type. The resulting chimeric RNA may provide a desired function, or may produce a gene product in the specific cell type. The specific cells may include, but are not limited to those infected with viral or other infectious agents, benign or malignant neoplasms, or components of the immune system which are involved in autoimmune disease or tissue rejection. Specificity is achieved by modification of the binding domain of the PTM to bind to the target endogenous pre-mRNA. The gene products encoded by the chimeric RNA can be any gene, including genes having clinical usefulness, for example, therapeutic or marker genes, and genes encoding toxins.

Structure of the Pre-Trans-Splicing Molecules

The present invention provides compositions for use in generating novel chimeric nucleic acid molecules through targeted trans-splicing. The PTMs of the invention comprise (i) one or more target binding domains that targets binding of the PTM to a pre-mRNA (ii) a 3' splice region that includes a branch point, pyrimidine tract and a 3' splice acceptor site and/or 5' splice donor site; and (iii) a spacer region to separate the RNA splice site from the target binding domain. Additionally, the PTMs can be engineered to contain any nucleotide sequence encoding a translatable protein product. In yet another embodiment of the invention, the PTMs can be engineered to contain nucleotide sequences that inhibit the translation of the chimeric RNA molecule. For example, the nucleotide sequences may contain translational stop codons or nucleotide sequences that form secondary structures and thereby inhibit translation. Alternatively, the chimeric RNA may function as an anti-sense molecule thereby inhibiting translation of the RNA to which it binds.

The target binding domain of the PTM may contain one or two binding domains of at least 15 to 30 (up to several hundred) nucleotides which are complementary to and in anti-sense orientation to the targeted region of the selected pre-mRNA. This confers specificity of binding and anchors the pre-mRNA closely in space so that the spliceosome processing machinery of the nucleus can trans-splice a portion of the PTM to a portion of the pre-mRNA. A second target binding region may be placed at the 3' end of the molecule and can be incorporated into the PTM of the invention. Absolute complementarity, although preferred, is not required. A sequence "complementary" to a portion of an RNA, as referred to herein, means a sequence having sufficient complementarity to be able to hybridize with the RNA, forming a stable duplex. The ability to hybridize will depend on both the degree of complementarity and the length of the nucleic acid (See, for example, Sambrook et al., 1989, Molecular Cloning, A Laboratory Manual, 2d Ed., Cold Spring Harbor Laboratory Press, Cold Spring Harbor, N.Y.). Generally, the longer the hybridizing nucleic acid, the more base mismatches with an RNA it may contain and still form a stable duplex. One skilled in the art can ascertain a tolerable degree of mismatch by use of standard procedures to determine the melting point of the hybridized complex.

Where the PTMs are designed for use in intron-exon tagging or for peptide affinity tagging, a library of PTMs is genetically engineered to contain random nucleotide sequences in the target binding domain. The goal of generating such a library of PTM molecules is that the library will contain a population of PTM molecules capable of binding to each RNA molecule expressed in the cell. A recombinant expression vector can be genetically engineered to contain a coding region for a PTM including a restriction endonuclease site that can be used for insertion of random DNA fragments into the PTM to form random target binding domains. The random nucleotide sequences to be included in the PTM as target binding domains can be generated using a variety of different methods well known to those of skill in the art, including but not limited to, partial digestion of DNA with restriction enzymes or mechanical shearing of DNA to generate random fragments of DNA. Random binding domain regions may also be generated by degenerate oligonucleotide synthesis. The degenerate oligonucleotides can be engineered to have restriction endonuclease recognition sites on each end to facilitate cloning into a PTM molecule for production of a library of PTM molecules having degenerate binding domains.

Binding may also be achieved through other mechanisms, for example, through triple helix formation or protein/nucleic acid interactions such as those in which the PTM is engineered to recognize a specific RNA binding protein, i.e., a protein bound to a specific target pre-mRNA. Alternatively, the PTMs of the invention may be designed to recognize secondary structures, such as for example, hairpin structures resulting from intramolecular base pairing between nucleotides within an RNA molecule.

The PTM molecule also contains a 3' splice region that includes a branch point, pyrimidine tract and a 3' splice acceptor AG site and/or a 5' splice donor site. Consensus sequences for the 5' splice donor site and the 3' splice region used in RNA splicing are well known in the art (See, Moore, et al., 1993, The RNA World, Cold Spring Harbor Laboratory Press, p. 303–358). In addition, modified consensus sequences that maintain the ability to function as 5' donor splice sites and 3' splice regions may be used in the practice of the invention. Briefly, the 5' splice site consensus sequence is AG/GURAGU (where A=adenosine, U=uracil, G=guanine, C=cytosine, R=purine and /=the splice site). The 3' splice site consists of three separate sequence elements: the branch point or branch site, a polypyrimidine tract and the 3' consensus sequence (YAG). The branch point consensus sequence in mammals is YNYUR<u>A</u>C (Y=pyrimidine). The underlined A is the site of branch formation. A polypyrimidine tract is located between the branch point and the splice site acceptor and is important for different branch point utilization and 3' splice site recognition.

A spacer region to separate the RNA splice site from the target binding domain is also included in the PTM. The spacer region can have features such as stop codons which would block any translation of an unspliced PTM and/or sequences that enhance trans-splicing to the target pre-mRNA.

In a preferred embodiment of the invention, a "safety" is also incorporated into the spacer, binding domain, or elsewhere in the PTM to prevent non-specific trans-splicing. This is a region of the PTM that covers elements of the 3' and/or 5' splice site of the PTM by relatively weak complementarity, preventing non-specific trans-splicing. The PTM is designed in such a way that upon hybridization of the binding/targeting portion(s) of the PTM, the 3' and/or 5'splice site is uncovered and becomes fully active.

The "safety" consists of one or more complementary stretches of cis-sequence (or could be a second, separate, strand of nucleic acid) which weakly binds to one or both sides of the PTM branch point, pyrimidine tract, and/or 3' splice site (splicing elements), or could bind to parts of the splicing elements themselves. This "safety" binding prevents the splicing elements from being active (i.e. block U2 snRNP or other splicing factors from attaching to the PTM splice site recognition elements). The binding of the "safety" may be disrupted by the binding of the target binding region of the PTM to the target pre-mRNA, thus exposing and activating the PTM splicing elements (making them available to trans-splice into the target pre-mRNA).

A nucleotide sequence encoding a translatable protein capable of producing an effect, such as cell death, or alternatively, one that restores a missing function or acts as a marker, is included in the PTM of the invention. For example, the nucleotide sequence can include those sequences encoding gene products missing or altered in known genetic diseases. Alternatively, the nucleotide sequences can encode marker proteins or peptides which may be used to identify or image cells. In yet another embodiment of the invention nucleotide sequences encoding affinity tags such as, HIS tags (6 consecutive histidine residues) (Janknecht, et al., 1991, Proc. Natl. Acad. Sci. USA 88:8972–8976), the C-terminus of glutathione-S-transferase (GST) (Smith and Johnson, 1986, Proc. Natl. Acad. Sci. USA 83:8703–8707) (Pharmacia) or FLAG (Asp-Tyr-Lys-Asp-Asp-Asp-Lys) (SEQ ID NO:66) (Eastman Kodak/IBI, Rochester, N.Y.) can be included in PTM molecules for use in affinity purification. The use of PTMs containing such nucleotide sequences results in the production of a chimeric RNA encoding a fusion protein containing peptide sequences normally expressed in a cell linked to the peptide affinity tag. The affinity tag provides a method for the rapid purification and identification of peptide sequences expressed in the cell. In a preferred embodiment the nucleotide sequences may encode toxins or other proteins which provide some function which enhances the susceptibility of the cells to subsequent treatments, such as radiation or chemotherapy.

In a highly preferred embodiment of the invention a PTM molecule is designed to contain nucleotide sequences encoding the Diphtheria toxin subunit A (Greenfield, L., et al., 1983, Proc. Nat'l. Acad. Sci. USA 80: 6853–6857). Diphtheria toxin subunit A contains enzymatic toxin activity and will function if expressed or delivered into human cells resulting in cell death. Furthermore, various other known peptide toxins may be used in the present invention, including but not limited to, ricin, Pseudomonus toxin, Shiga toxin and exotoxin A.

Additional features can be added to the PTM molecule either after, or before, the nucleotide sequence encoding a translatable protein, such as polyadenylation signals or 5' splice sequences to enhance splicing, additional binding regions, "safety"-self complementary regions, additional splice sites, or protective groups to modulate the stability of the molecule and prevent degradation.

Additional features that may be incorporated into the PTMs of the invention include stop codons or other elements in the region between the binding domain and the splice site to prevent unspliced pre-mRNA expression. In another embodiment of the invention, PTMs can be generated with a second anti-sense binding domain downstream from the nucleotide sequences encoding a translatable protein to promote binding to the 3' target intron or exon and to block the fixed authentic cis-5' splice site (U5 and/or U1 binding sites). PTMs may also be made that require a double trans-splicing reaction for expression of the trans-spliced product. Such PTMs could be used to replace an internal exon which could be useful for RNA repair. Further elements such as a 3' hairpin structure, circularized RNA, nucleotide base modification, or a synthetic analog can be incorporated into PTMs to promote or facilitate nuclear localization and spliceosomal incorporation, and intracellular stability.

The PTMs of the invention can be used in methods designed to produce a novel chimeric RNA in a target cell. The methods of the present invention comprise delivering to the target cell a PTM which may be in any form used by one skilled in the art, for example, an RNA molecule, or a DNA vector which is transcribed into a RNA molecule, wherein said PTM binds to a pre-mRNA and mediates a trans-splicing reaction resulting in formation of a chimeric RNA comprising a portion of the PTM molecule spliced to a portion of the pre-mRNA.

Synthesis of the Trans-splicing Molecules

The nucleic acid molecules of the invention can be RNA or DNA or derivatives or modified versions thereof, single-stranded or double-stranded. By nucleic acid is meant a PTM molecule or a nucleic acid molecule encoding a PTM molecule, whether composed of deoxyribonucleotides or ribonucleosides, and whether composed of phosphodiester linkages or modified linkages. The term nucleic acid also specifically includes nucleic acids composed of bases other than the five biologically occurring bases (adenine, guanine, thymine, cytosine and uracil).

The RNA and DNA molecules of the invention can be prepared by any method known in the art for the synthesis of DNA and RNA molecules. For example, the nucleic acids may be chemically synthesized using commercially available reagents and synthesizers by methods that are well known in the art (see, e.e., Gait, 1985, Oligonucleotide Synthesis: A Practical Approach, IRL Press, Oxford, England). Alternatively, RNA molecules can be generated by in vitro and in vivo transcription of DNA sequences encoding the RNA molecule. Such DNA sequences can be incorporated into a wide variety of vectors which incorporate suitable RNA polymerase promoters such as the T7 or SP6 polymerase promoters. RNAs may be produced in high yield via in vitro transcription using plasmids such as SPS65 (Promega Corporation, Madison, Wis.). In addition, RNA amplification methods such as Q-β amplification can be utilized to produce RNAs.

The nucleic acid molecules can be modified at the base moiety, sugar moiety, or phosphate backbone, for example, to improve stability of the molecule, hybridization, transport into the cell, etc. For example, modification of a PTM to reduce the overall charge can enhance the cellular uptake of the molecule. In addition modifications can be made to reduce susceptibility to nuclease degradation. The nucleic acid molecules may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. W088/09810, published Dec. 15, 1988) or the blood-brain barrier (see, e.g., PCT Publication No. W089/10134, published Apr. 25, 1988), hybridization-triggered cleavage agents. (See, e.g., Krol et al., 1988, Bio Techniques 6:958–976) or intercalating agents. (See, e.g., Zon, 1988, Pharm. Res. 5:539–549). To this end, the nucleic acid molecules may be conjugated to another molecule, e.g., a peptide, hybridization triggered cross-linking agent, transport agent, hybridization-triggered cleavage agent, etc. Various other well-known modifications to the DNA molecules can be introduced as a means of increasing intracellular stability and half-life. Possible modifications include, but are not limited to, the addition of flanking sequences of ribo- or deoxy- nucleotides to the 5' and/or 3' ends of the molecule. In some circumstances where increased stability is desired, nucleic acids having modified internucleoside linkages such as 2'-0-methylation may be preferred. Nucleic acids containing modified internucleoside linkages may be synthesized using reagents and methods that are well known in the art (see, Uhlmann et al., 1990, Chem. Rev. 90:543–584; Schneider et al., 1990, Tetrahedron Lett. 31:335 and references sited therein).

The nucleic acids may be purified by any suitable means, as are well known in the art. For example, the nucleic acids can be purified by reverse phase chromatography or gel electrophoresis. Of course, the skilled artisan will recognize that the method of purification will depend in part on the size of the nucleic acid to be purified.

In instances where a nucleic acid molecule encoding a PTM is utilized, cloning techniques known in the art may be used for cloning of the nucleic acid molecule into an expression vector. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

The DNA encoding the PTM of interest may be recombinantly engineered into a variety of host vector systems that also provide for replication of the DNA in large scale and contain the necessary elements for directing the transcription of the PTM. The use of such a construct to transfect target cells in the patient will result in the transcription of sufficient amounts of PTMs that will form complementary base pairs with the endogenously expressed pre-mRNA targets and thereby facilitate a trans-splicing reaction between the complexed nucleic acid molecules. For example, a vector can be introduced in vivo such that it is taken up by a cell and directs the transcription of the PTM molecule. Such a vector can remain episomal or become chromosomally integrated, as long as it can be transcribed to produce the desired RNA. Such vectors can be constructed by recombinant DNA technology methods standard in the art.

Vectors encoding the PTM of interest can be plasmid, viral, or others known in the art, used for replication and expression in mammalian cells. Expression of the sequence encoding the PTM can be regulated by any promoter known in the art to act in mammalian, preferably human cells. Such promoters can be inducible or constitutive. Such promoters include but are not limited to: the SV40 early promoter region (Benoist, C. and Chambon, P. 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:14411445), the regulatory sequences of the metallothionein gene (Brinster et al., 1982, Nature 296:39–42), the viral CMV promoter, the human chorionic gonadotropin-β promoter (Hollenberg et al., 1994, Mol. Cell. Endocrinology 106:111–119), etc. Any type of plasmid, cosmid, YAC or viral vector can be used to prepare the recombinant DNA construct which can be introduced directly into the tissue site. Alternatively, viral vectors can be used which selectively infect the desired target cell.

For use of PTMs encoding peptide affinity purification tags, it is desirable to insert nucleotide sequences containing random target binding sites into the PTMs and clone them into a selectable mammalian expression vector system. A number of selection systems can be used, including but not limited to selection for expression of the herpes simplex virus thymidine kinase, hypoxanthine-guanine phosphoribosyltransferase and adenine phosphoribosyl tranferase protein in tk-, hgprt- or aprt- deficient cells, respectively. Also, anti-metabolic resistance can be used as the basis of selection for dihydrofolate tranferase (dhfr), which confers resistance to methotrexate; xanthine-guanine phosphoribosyl transferase (gpt), which confers resistance to mycophenolic acid; neomycin (neo), which confers resistance to aminoglycoside G-418; and hygromycin B phosphotransferase (hygro) which confers resistance to hygromycin. In a preferred embodiment of the invention, the cell culture is transformed at a low ratio of vector to cell such that there will be only a single vector, or a limited number of vectors, present in any one cell. Vectors for use in the practice of the invention include any eukaryotic expression vectors, including but not limited to viral expression vectors such as those derived from the class of retroviruses or adeno-associated viruses.

Uses and Administration of Trans-splicing Molecules

Use of PTM Moleculed for Gene Regulation, Gene Repair and Targeted Cell Death

The compositions and methods of the present invention will have a variety of different applications including gene regulation, gene repair and targeted cell death. For example, trans-splicing can be used to introduce a protein with toxic properties into a cell. In addition, PTMs can be engineered to bind to viral mRNA and destroy the function of the viral mRNA, or alternatively, to destroy any cell expressing the viral mRNA. In yet another embodiment of the invention, PTMs can be engineered to place a stop codon in a deleterious mRNA transcript thereby decreasing the expression of that transcript.

Targeted trans-splicing can be used to repair or correct transcripts that are either truncated or contain point mutations. The PTMs of the invention are designed to cleave a targeted transcript upstream or downstream of a specific mutation or upstream of a premature 3' and correct the mutant transcript via a trans-splicing reaction which replaces the portion of the transcript containing the mutation with a functional sequence.

Cystic fibrosis (CF) is the most common fatal genetic disease in humans. Based on both genetic and molecular analyses, the gene associated with cystic fibrosis has been isolated and its protein product deduced (Kerem, B. S. et al., 1989, Science 245:1073–1080; Riordan et al., 1989, Science 245:1066–1073;Rommans, et al., 1989, Science 245:1059–1065). The protein product of the CF associated gene is called the cystic fibrosis transmembrane conductance regulator (CFTR). In a specific embodiment of the invention, a trans-splicing reaction will be used to correct a genetic defect in the DNA sequence encoding the cystic fibrosis transmembrane regulator (CFTR) whereby the DNA sequence encoding the cystic fibrosis trans-membrane regulator protein is expressed and a functional chloride ion channel is produced in the airway epithelial cells of a patient.

Figure 13:
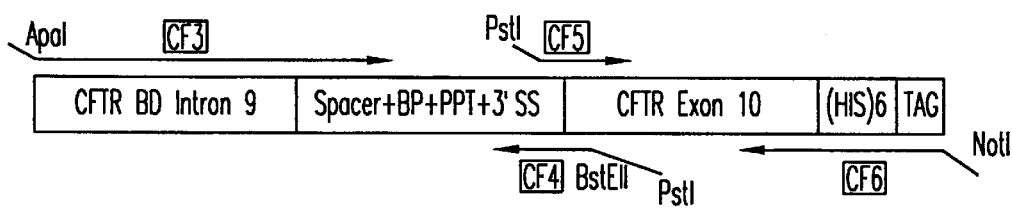
Figure 13:
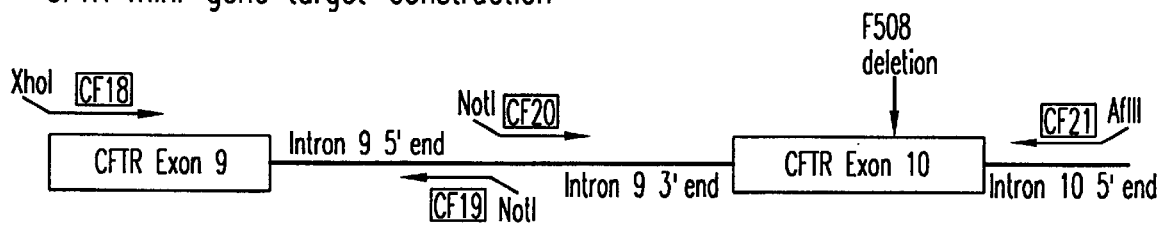
Figure 13:
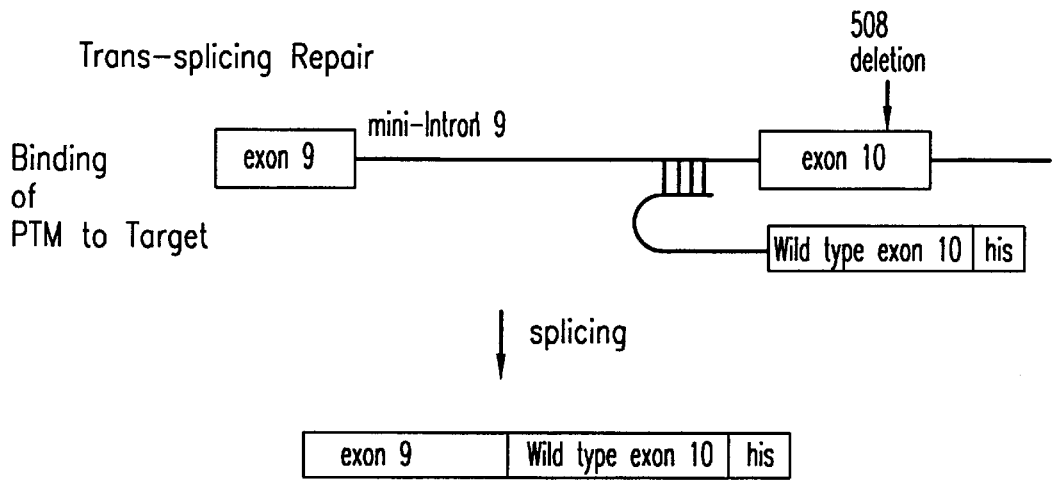
Figure 15A:
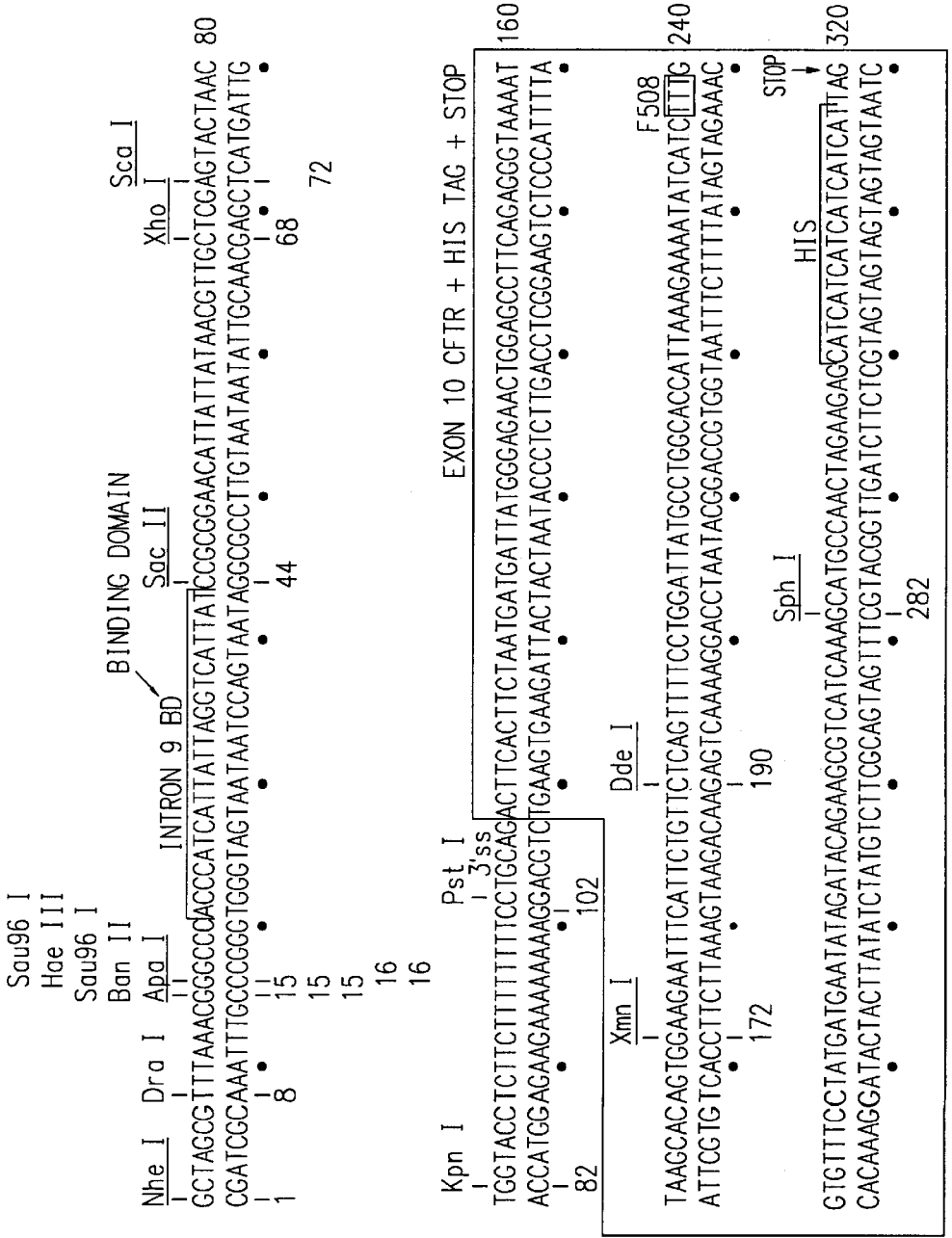
Figure 15B:
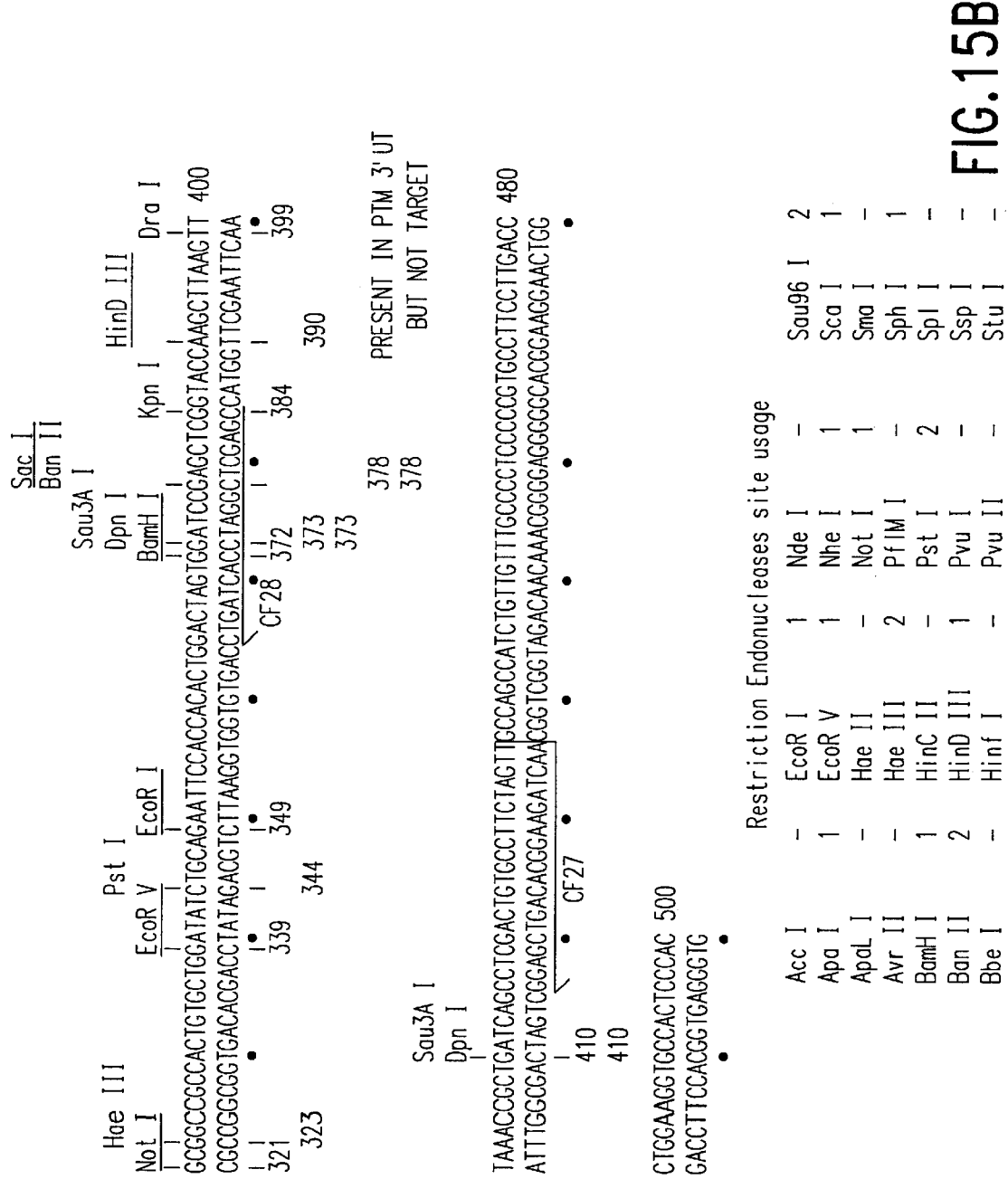

Population studies have indicated that the most common cystic fibrosis mutation is a deletion of the three nucleotides in exon 10 that encode phenylalanine at position 508 of the CFTR amino acid sequence. As indicated in FIG. 15, a trans-splicing reaction was capable of correcting the deletion at position 508 in the CFTR amino acid sequence. The PTM used for correction of the genetic defect contained a CFTR BD intron 9 sequence, a spacer sequence, a branch point, a polypyrimidine tract, a 3' splice site and a wild type CFTR BD exon 10 sequence (FIG. 13). The successful correction of the mutated DNA encoding CFTR utilizing a trans-splicing reaction supports the general application of PTMs for correction of genetic defects.

Various delivery systems are known and can be used to transfer the compositions of the invention into cells, e.g. encapsulation in liposomes, microparticles, microcapsules, recombinant cells capable of expressing the composition, receptor-mediated endocytosis (see, e.g., Wu and Wu, 1987, J. Biol. Chem. 262:4429–4432), construction of a nucleic acid as part of a retroviral or other vector, injection of DNA, electroporation, calcium phosphate mediated transfection, etc.

The compositions and methods can be used to treat cancer and other serious viral infections, autoimmune disorders, and other pathological conditions in which the alteration or elimination of a specific cell type would be beneficial. Additionally, the compositions and methods may also be used to provide a gene encoding a functional biologically active molecule to cells of an individual with an inherited genetic disorder where expression of the missing or mutant gene product produces a normal phenotype.

In a preferred embodiment, nucleic acids comprising a sequence encoding a PTM are administered to promote PTM function, by way of gene delivery and expression into a host cell. In this embodiment of the invention, the nucleic acid mediates an effect by promoting PTM production. Any of the methods for gene delivery into a host cell available in the art can be used according to the present invention. For general reviews of the methods of gene delivery see Strauss, M. and Barranger, J. A., 1997, Concepts in Gene Therapy, by Walter de Gruyter & Co., Berlin; Goldspiel et al., 1993, Clinical Pharmacy 12:488–505; Wu and Wu, 1991, Biotherapy 3:87–95; Tolstoshev, 1993, Ann. Rev. Pharmacol. Toxicol. 33:573–596; Mulligan, 1993, Science 260:926–932; and Morgan and Anderson, 1993, Ann. Rev. Biochem. 62:191–217; 1993, TIBTECH 11(5):155–215. Exemplary methods are described below.

Delivery of the nucleic acid into a host cell may be either direct, in which case the host is directly exposed to the nucleic acid or nucleic acid-carrying vector, or indirect, in which case, host cells are first transformed with the nucleic acid in vitro, then transplanted into the host. These two approaches are known, respectively, as in vivo or ex vivo gene delivery.

In a specific embodiment, the nucleic acid is directly administered in vivo, where it is expressed to produce the PTM. This can be accomplished by any of numerous methods known in the art, e.g., by constructing it as part of an appropriate nucleic acid expression vector and administering it so that it becomes intracellular, e.g. by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, J. Biol. Chem. 262:4429–4432).

In a specific embodiment, a viral vector that contains the PTM can be used. For example, a retroviral vector can be utilized that has been modified to delete retroviral sequences that are not necessary for packaging of the viral genome and integration into host cell DNA (see Miller et al., 1993, Meth. Enzymol. 217:581–599). Alternatively, adenoviral or adeno-associated viral vectors can be used for gene delivery to cells or tissues. (See, Kozarsky and Wilson, 1993, Current Opinion in Genetics and Development 3:499–503 for a review of adenovirus-based gene delivery).

Another approach to gene delivery into a cell involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. The resulting recombinant cells can be delivered to a host by various methods known in the art. In a preferred embodiment, the cell used for gene delivery is autologous to the host cell.

The present invention also provides for pharmaceutical compositions comprising an effective amount of a PTM or a nucleic acid encoding a PTM, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Examples of suitable pharmaceutical carriers are described in "Remington's Pharmaceutical sciences" by E. W. Martin.

In specific embodiments, pharmaceutical compositions are administered: (1) in diseases or disorders involving an absence or decreased (relative to normal or desired) level of an endogenous protein or function, for example, in hosts where the protein is lacking, genetically defective, biologically inactive or underactive, or under expressed; or (2) in diseases or disorders wherein, in vitro or in vivo, assays indicate the utility of PTMs that inhibit the function of a particular protein. The activity of the protein encoded for by the chimeric mRNA resulting from the PTM mediated trans-splicing reaction can be readily detected, e.g., by obtaining a host tissue sample (e.g., from biopsy tissue) and assaying it in vitro for mRNA or protein levels, structure and/or activity of the expressed chimeric mRNA. Many methods standard in the art can be thus employed, including but not limited to immunoassays to detect and/or visualize the protein encoded for by the chimeric mRNA (e.g., Western blot, immunoprecipitation followed by sodium dodecyl sulfate polyacrylamide gel electrophoresis, immunocytochemistry, etc.) and/or hybridization assays to detect formation of chimeric mRNA expression by detecting and/or visualizing the presence of chimeric mRNA (e.g., Northern assays, dot blots, in situ hybridization, and Reverse-Transcription PCR, etc.), etc.

The present invention also provides for pharmaceutical compositions comprising an effective amount of a PTM or a nucleic acid encoding a PTM, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Examples of suitable pharmaceutical carriers are described in "Remington's Pharmaceutical sciences" by E. W. Martin. In a specific embodiment, it may be desirable to administer the pharmaceutical compositions of the invention locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Other control release drug delivery systems, such as nanoparticles, matrices such as controlled-release polymers, hydrogels.

The PTM will be administered in amounts which are effective to produce the desired effect in the targeted cell. Effective dosages of the PTMs can be determined through procedures well known to those in the art which address such parameters as biological half-life, bioavailability and toxicity. The amount of the composition of the invention which will be effective will depend on the nature of the disease or disorder being treated, and can be determined by standard clinical techniques. In addition, in vitro assays may optionally be employed to help identify optimal dosage ranges.

The present invention also provides a pharmaceutical pack or kit comprising one or more containers filled with one or more of the ingredients of the pharmaceutical compositions of the invention optionally associated with such container(s) can be a notice in the form prescribed by a governmental agency regulating the manufacture, use or sale of pharmaceuticals or biological products, which notice reflects approval by the agency of manufacture, use or sale for human administration.

Use of PTM Molecules for Exon Tagging

In view of current efforts to sequence and characterize the genomes of humans and other organisms, there is a need for methods that facilitate such characterization. A majority of the information currently obtained by genomic mapping and sequencing is derived from complementary DNA (cDNA) libraries, which are made by reverse transcription of mRNA into cDNA. Unfortunately, this process causes the loss of information concerning intron sequences and the location of exon/intron boundaries.

The present invention encompasses a method for mapping exon-intron boundaries in pre-mRNA molecules comprising (i) contacting a pre-transplicing molecule containing a random target binding domain with a pre-mRNA molecule under conditions in which a portion of the pre-trans-splicing molecule is trans-spliced to a portion of the target pre-mRNA to form a chimeric mRNA; (ii) amplifying the chimeric mRNA molecule; (iii) selectively purifying the amplified molecule; and (iv) determining the nucleotide sequence of the amplified molecule thereby identifying the intron-exon boundaries.

In an embodiment of the present invention, PTMs can be used in trans-splicing reactions to locate exon-intron boundaries in pre-mRNAs molecules. PTMs for use in mapping of intron-exon boundaries have structures similar to those described above in Section 5.1. Specifically, the PTMs contain (i) a target binding domain that is designed to bind to many pre-mRNAs: (ii) a 3' splice region that includes a branch point, pyrimidine tract and a 3' splice acceptor site, or a 5' splice donor site; (iii) a spacer region that separates the mRNA splice site from the target binding domain; and (iv) a tag region that will be trans-spliced onto a pre-mRNA. For purposes of intron-exon mapping, the PTMs are genetically engineered to contain target binding domains comprising random nucleotide sequences. The random nucleotide sequences contain at least 15–30 and up to several hundred nucleotide sequences capable of binding and anchoring a pre-mRNA so that the spliceosome processing machinery of the nucleus can trans-splice a portion (tag or marker region) of the PTM to a portion of the pre-mRNA. PTMs containing short target binding domains, or containing inosines bind under less stringent conditions to the pre-mRNA molecules. In addition, strong branch point sequences and pyrimidine tracts serve to increase the non-specificity of PTM trans-splicing.

The random nucleotide sequences used as target binding domains in the PTM molecules can be generated using a variety of different methods, including, but not limited to, partial digestion of DNA with restriction endonucleases or mechanical shearing of the DNA. The use of such random nucleotide sequences is designed to generate a vast array of PTM molecules with different binding activities for each target pre-mRNA expressed in a cell. Randomized libraries of oligonucleotides can be synthesized with appropriate restriction endonucleases recognition sites on each end for cloning into PTM molecules genetically engineered into plasmid vectors. When the randomized oligonucleotides are litigated and expressed, a randomized binding library of PTMs is generated.

In a specific embodiment of the invention, an expression library encoding PTM molecules containing target binding domains comprising random nucleotide sequences can be generated using a variety of methods which are well known to those of skill in the art. Ideally, the library is complex enough to contain PTM molecules capable of interacting with each target pre-mRNA expressed in a cell.

Figure 9:
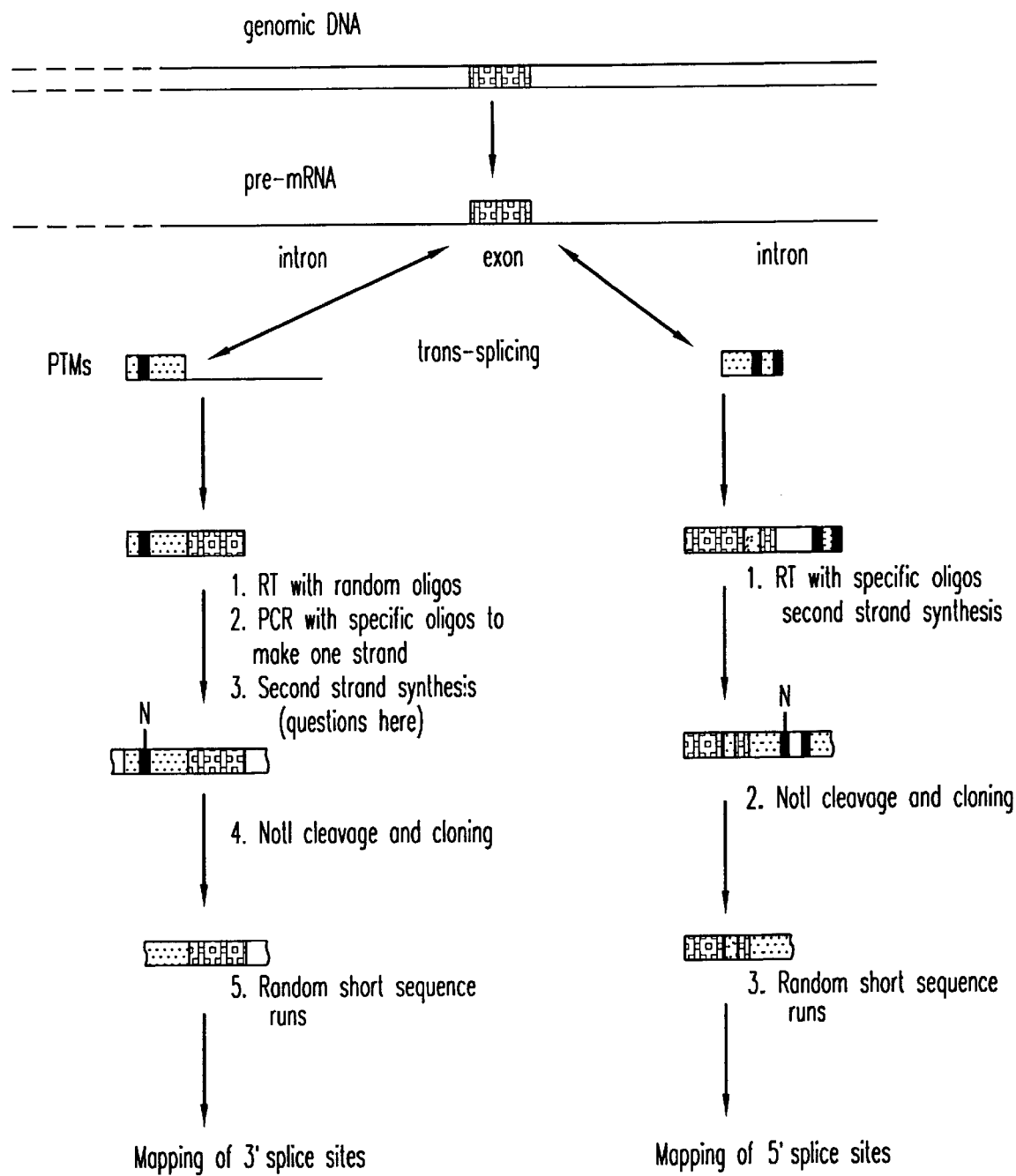
Figure 10A:
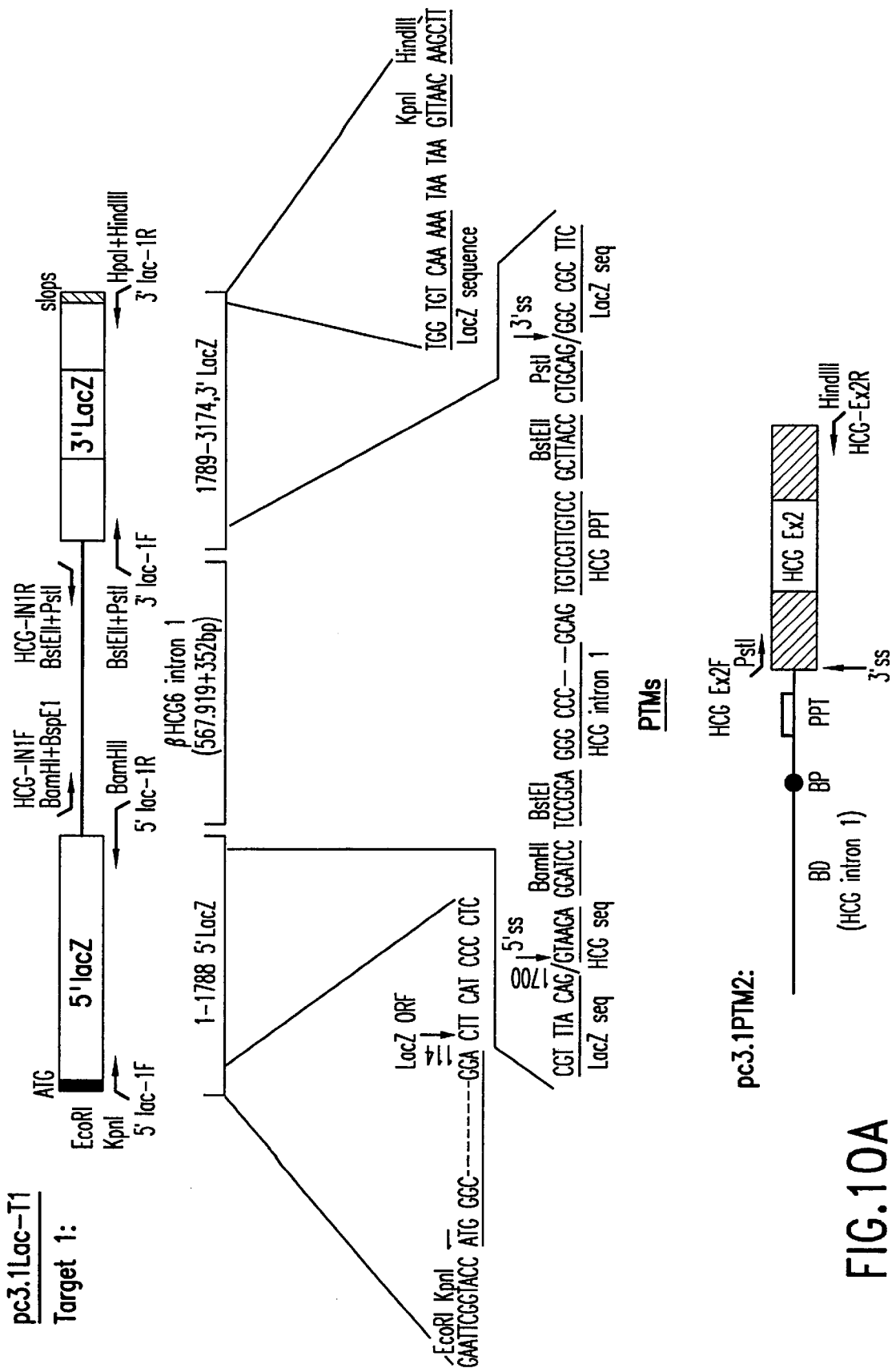
Figure 10B:
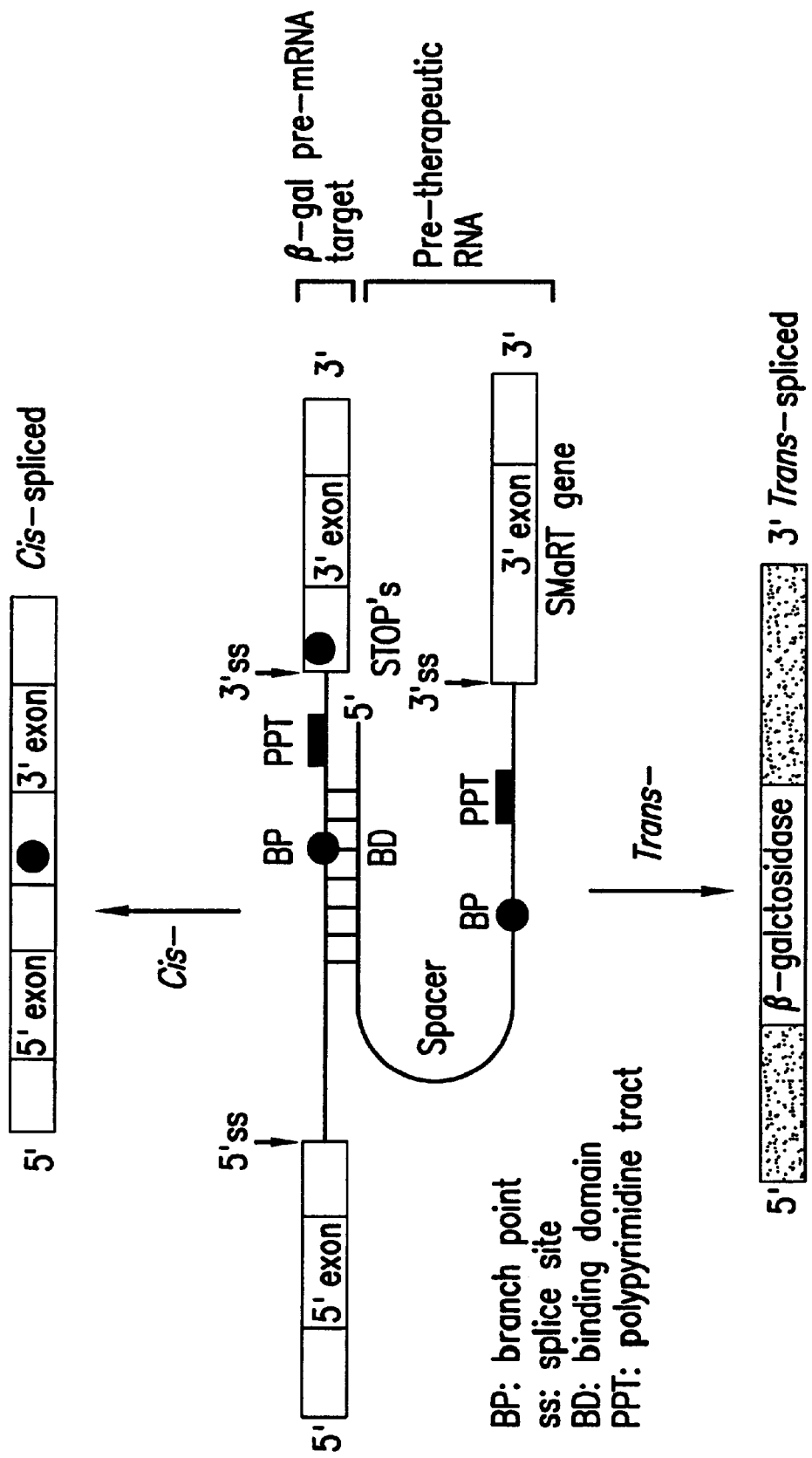
Figure 11A:
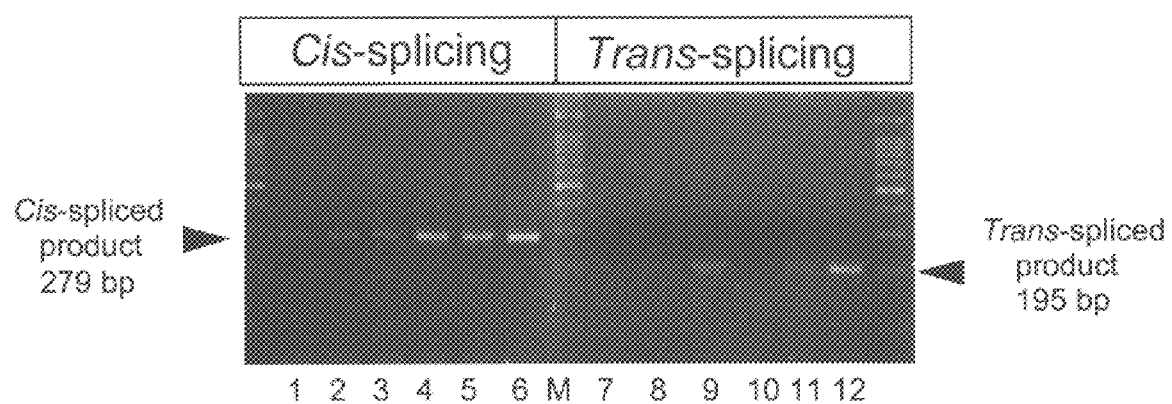
Figure 11B:
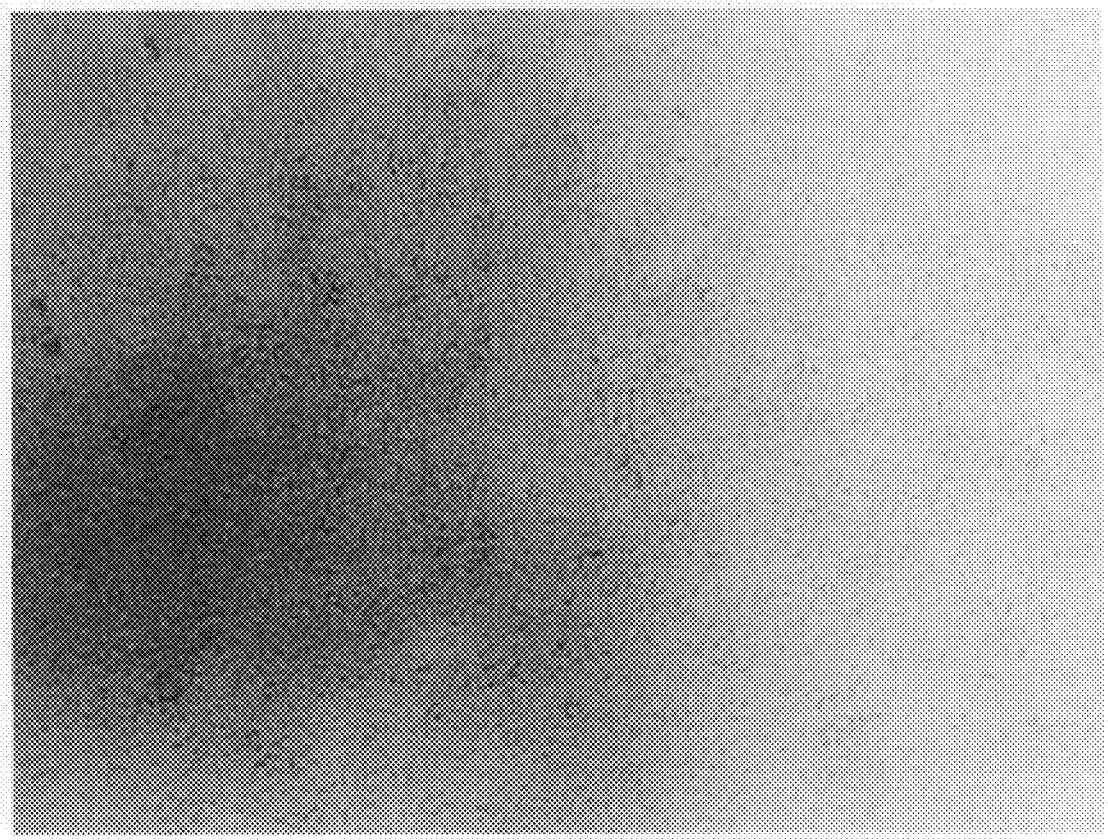
Figure 11C:
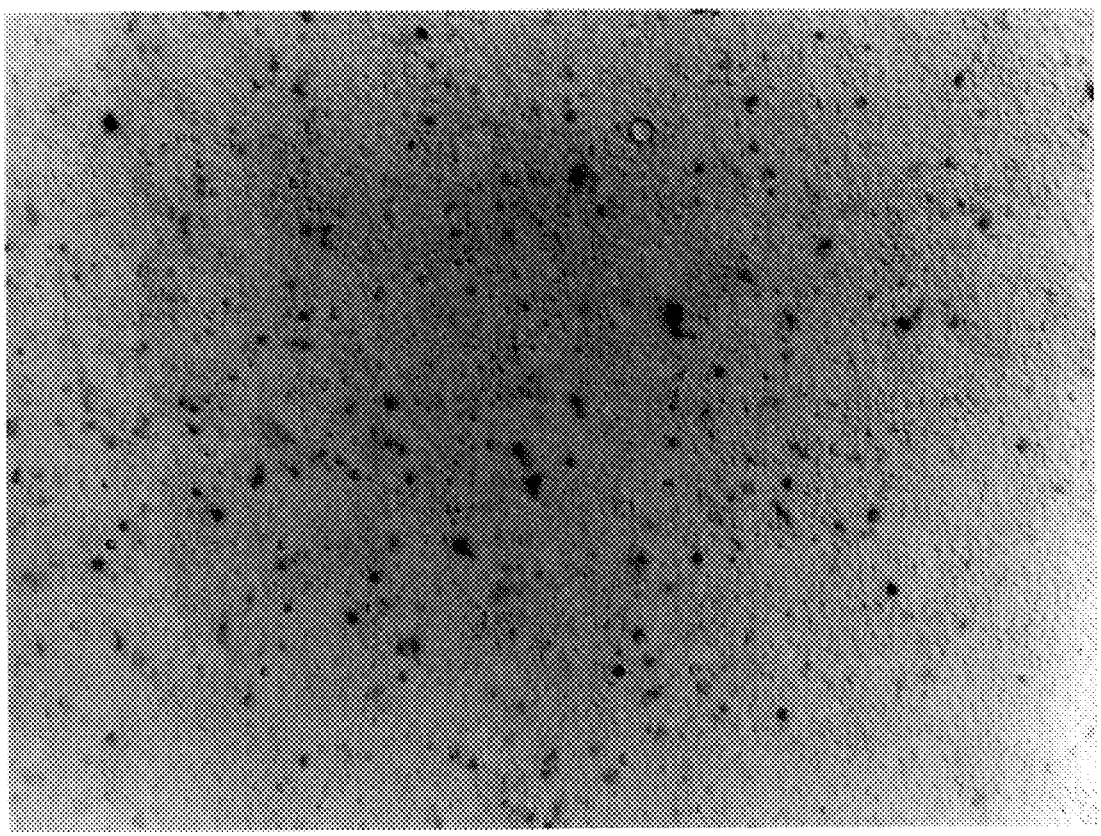

By way of example, FIG. 9 is a schematic representation of two forms of PTMs which can be utilized to map intron-exon boundaries. The PTM on the left is capable of non-specifically trans-splicing into a pre-mRNA 3' splice site, while the PTM on the right is capable of trans-splicing into a pre-mRNA 5' splice site. Trans-splicing between the PTM and the target pre-mRNA results in the production of a chimeric mRNA molecule having a specific nucleotide sequence "tag" on either the 3' or 5' end of an authentic exon.

Following selective purification, a DNA sequencing reaction is then performed using a primer which begins in the tag nucleotide sequence of the PTM and proceeds into the sequence of the tagged exon. The sequence immediately following the last nucleotide of the tag nucleotide sequence represents an exon boundary. For identification of intron-exon tags, the trans-splicing reactions of the invention can be performed either in vitro or in vivo using methods well known to those of skill in the art.

Use of PTM Moleculed for Identification of Proteins Expressed in a Cell

In yet another embodiment of the invention, PTM mediated trans-splicing reactions can be used to identify previously undetected and unknown proteins expressed in a cell. This method is especially useful for identification of proteins that cannot be detected by a two-dimensional electrophoresis, or by other methods, due to inter alia the small size of the protein, low concentration of the protein, or failure to detect the protein due to similar migration patterns with other proteins in two-dimensional electrophoresis.

The present invention relates to a method for identifying proteins expressed in a cell comprising (i) contacting a pre-transplicing molecule containing a random target binding domain and a nucleotide sequence encoding a peptide tag with a pre-mRNA molecule under conditions in which a portion of the pre-trans-splicing molecule is trans-spliced to a portion of the target pre-mRNA to form a chimeric mRNA encoding a fusion polypeptide or separating it by gel electrophoresis (ii) affinity purifying the fusion polypeptide; and (iii) determining the amino acid sequence of the fusion protein.

To identify proteins expressed in a cell, the PTMs of the invention are genetically engineered to contain: (i) a target binding domain comprising randomized nucleotide sequences; (ii) a 3' splice region that includes a branch point, pyrimidine tract and a 3' splice acceptor site and/or a 5' splice donor site; (iii) a spacer region that separates the PTM splice site from the target binding domain; and (iv) nucleotide sequences encoding a marker or peptide affinity purification tag. Such peptide tags include, but are not limited to, HIS tags (6 histidine consecutive residues) (Janknecht, et al., 1991 Proc. Natl. Acad. Sci. USA 88:8972–8976), glutathione-S-transferase (GST) (Smith, D. B. and Johnson K. S., 1988, Gene 67:31) (Pharmacia) or FLAG (Kodak/IBI) tags (Nisson, J. et al. J. Mol. Recognit., 1996, 5:585–594)

Trans-splicing reactions using such PTMs results in the generation of chimeric mRNA molecules encoding fusion proteins comprising protein sequences normally expressed in a cell linked to a marker or peptide affinity purification tag. The desired goal of such a method is that every protein synthesized in a cell receives a marker or peptide affinity tag thereby providing a method for identifying each protein expressed in a cell.

In a specific embodiment of the invention, PTM expression libraries encoding PTMs having different target binding domains comprising random nucleotide sequences are generated. The desired goal is to create a PTM expression library that is complex enough to produce a PTM capable of binding to each pre-mRNA expressed in a cell. In a preferred embodiment, the library is cloned into a mammalian expression vector that results in one, or at most, a few vectors being present in any one cell.

To identify the expression of chimeric proteins, host cells are transformed with the PTM library and plated so that individual colonies containing one PTM vector can be grown and purified. Single colonies are selected, isolated, and propagated in the appropriate media and the labeled chimeric protein exon(s) fragments are separated away from other cellular proteins using, for example, an affinity purification tag. For example, affinity chromatography can involve the use of antibodies that specifically bind to a peptide tag such as the FLAG tag. Alternatively, when utilizing HIS tags, the fusion proteins are purified using a $Ni^{2+}$ nitriloacetic acid agarose columns, which allows selective elution of bound peptide eluted with imidazole containing buffers. When using GST tags, the fusion proteins are purified using glutathione-S-transferase agarose beads. The fusion proteins can then be eluted in the presence of free glutathione.

Following purification of the chimeric protein, an analysis is carried out to determine the amino acid sequence of the fusion protein. The amino acid sequence of the fusion protein is determined using techniques well known to those of skill in the art, such as Edman Degradation followed by amino acid analysis using HPLC, mass spectrometry or an amino acid analyzation. Once identified, the peptide sequence is compared to those sequences available in protein databases, such as GenBank. If the partial peptide sequence is already known, no further analysis is done. If the partial protein sequence is unknown, then a more complete sequence of that protein can be carried out to determine the full protein sequence. Since the fusion protein will contain only a portion of the full length protein, a nucleic acid encoding the full length protein can be isolated using conventional methods. For example, based on the partial protein sequence oligonucleotide primers can be generated for use as probes or PCR primers to screen a CDNA library.

EXAMPLE

Production of Trans-splicing Molecules

The following section describes the production of PTMs and the demonstration that such molecules are capable of mediating trans-splicing reactions resulting in the production of chimeric mRNA molecules.

Materials and Methods

Construction of Pre-mRNA Molecules

Plasmids containing the wild type diphtheria toxin subunit A (DT-A, wild-type accession #K01722) and a DT-A mutant (CRM 197, no enzymatic activity) were obtained from Dr. Virginia Johnson, Food and Drug Administration, Bethesda, Md. (Uchida et al., 1973 J. Biol. Chem 248:3838). For in vitro experiments, DT-A was amplified using primers: DT-1F (5'-GGCGCTGCAGGGCGCTGATGATGTTGTTG) SEQ ID NO:2; and DT-2R (5'-GGCGAAG CTTGGATCCGACACGATTTCCTGCACAGG) SEQ ID NO:3, cut with PstI and HindIII, and cloned into PstI and HindIII digested pBS(−) vector (Stratagene, La Jolla, Calif.). The resulting clone, pDTA was used to construct the individual PTMs. (1) pPTM+: Targeted construct. Created by inserting IN3-1 (5'AATTCTCTAGATGCTT CAC-CCGGGCCTGACTCGAGTACTAACTGGTACCTCT TCTTTTTTTTCCTGCA) SEQ ID NO:4 and IN2-4 (5'-GGAAAAAAAAGAAGAGGTACCAGTTAG-TACTCGAGTCAGG CCCGGGTGAAGCATCTAGAG) SEQ ID NO:5 primers into EcoRI and PstI digested pDTA. (2) pPTM+Sp: As pPTM+ but with a 30 bp spacer sequence between the BD and BP. Created by digesting pPTM+ with XhoI and ligating in the oligonucleotides, spacer S (5'-TCGAGCAACGTTATAATAATGTTC) SEQ ID NO:6 and spacer AS (5'-TCGAGAACATTATT ATAACGTTGC) SEQ ID NO:7. For in vivo studies, an EcoRI and HindIII fragment of pcPTM+Sp was cloned into mammalian expression vector pcDNA3.1 (Invitrogen), under the control of a CMV promoter. Also, the methionine at codon 14 was changed into isoleucine to prevent initiation of translation. The resulting plasmid was designated as pcPTM+Sp. (3) pPTM+ CRM: As pPTM+Sp but the wild type DT-A was substituted with CRM mutant DT-A (T. Uchida, et al., 1973, J. Biol. Chem. 248:3838). This was created by PCR amplification of a DT-A mutant (mutation at G52E) using primers DT-1F and DT-2R. For in vivo studies, an EcoRI HindIII fragment of PTM+CRM was cloned into pc3.1DNA that resulted in pcPTM+ARM. (4) PTM−: Non-targeted construct. Created by digestion of PTM+with EcoRI and Pst I, gel purified to remove the binding domain followed by ligation of the oligonucleotides, IN-5 (5'-ATCTCTAGATCAGGCCCGGGTGAAGCC CGAG) SEQ ID NO: 8 and IN-6 (5'-TGCTTCACCC GGGCCTGATCTAGAG) SEQ ID NO: 9. (5) PTM−Sp, is an identical version of the PTM−, except it has a 30 bp spacer sequence at the PstI site. Similarly, the splice mutants [Py(−)AG(−) and BP(−)Py(−)AG(−)] and safety variants [PTM+SF-Py1, PTM+SF-Py2, PTM+SFBP3 and PTM+ SFBP3-Py1] were constructed either by insertion or deletion of specific sequences (see Table 1).

contained 4 μl of annealed mRNA complex (100 ng of target and 200 ng of PTM), 1×splice buffer (2 Memorandum $MgCl_2$, 1 Memorandum ATP, 5 Memorandum creatinine phosphate, and 40 Memorandum KCl) and 4 μl of HeLa splice nuclear extract (Promega) in a 12.5 μl final volume. Reactions were incubated at 30° C. for the indicated times and stopped by the addition of an equal volume of high salt buffer (7 M urea, 5% SDS, 100 Memorandum LiCl, 10 Memorandum EDTA and 10 Memorandum TrisHCI, pH 7.5). Nucleic acids were purified by extraction with phenol:chloroform:isoamyl alcohol (50:49:1) followed by ethanol precipitation.

TABLE 1

Binding/non-binding domain, BP, PPT and 3' as sequences of different PTMs

| PTM construct | BD/NBD | BP | PPT | 3'ss |
| --- | --- | --- | --- | --- |
| PTM + Sp (targeted) | :TGCTTCACCCGGGCCTGA (SEQ ID NO:10) | TACTA<u>A</u>C | CTCTTCTTTTTTTCC (SEQ ID NO: 11) | CAG |
| PTM − Sp (non-targeted) | :CAACGTTATAATAATGTT (SEQ ID NO:12) | TACTA<u>A</u>C | CTCTTCTTTTTTTCC (SEQ ID NO:11) | CAG |
| PTM + Py (−)AG(−)BP(−) | :TGCTTCACCCGGGCCTGA (SEQ ID NO:10) | GGCTG<u>A</u>T | CTGTGATTAATAGCGG (SEQ ID NO:13) | ACG |
| PTM + Py(−)AG(−) | :TGCTTCACCCGGGCCTGA (SEQ ID NO: 10) | TACTA<u>A</u>C | CCTGGACGCGGAAGTT (SEQ ID NO: 14) | ACG |
| PTM + SF | :CTGGGACAAGGACACTGCTT CACCCGGTTAGTAGACCACA GCCCTGAAGCC (SEQ ID NO: 15) | TACTA<u>A</u>C | CTTCTGTTTTTTCTC (SEQ ID NO: 16) | CAG |
| PTM + SF − Py1 | :As in PTM + SF | TACTA<u>A</u>C | CTTCTGTATTATTCTC (SEQ ID NO: 17) | CAG |
| PTM + SF − Py2 | :As in PTM + SF | TACTA<u>A</u>C | GTTCTGTCCTTGTCTC (SEQ ID NO:18) | CAG |
| PTM + SF − BP3 | :As in PTM + SF | TGCTG<u>A</u>C | CTTCTGTTTTTTCTC (SEQ ID NO:16) | CAG |
| PTM + SFBP3 − Py1 | :As in PTM + SF | TGCTG<u>A</u>C | CTTCTGTATTATTCTC (SEQ ID NO: 17) | CAG |

Nucleotides in bold indicate the mutations compared to normal BP, PPT and 3' splice site.
Branch site A is underlined. The nucleotides in italics indicates the mismatch introduced into safety BD to mask the BP sequence in the PTM.

A double trans-splicing PTM construct (DS-PTM) was also made adding a 5' splice site and a second target binding domain complementary to the second intron of βHCG pre-mRNA to the 3' end of the toxin coding sequence of PTM+SF (FIG. A).

βHCG6 Target Pre-mRNA

To produce the in vitro target pre-mRNA, a SacI fragment of βHDG gene 6 (accession #X00266) was cloned into pBS(−). This produced an 805 bp insert from nucleotide 460 to 1265, which includes the 5' untranslated region, initiation codon, exon 1, intron 1, exon 2, and most of intron 2. For in vivo studies, an EcoRI and BamHI fragment was cloned into mammalian expression vector (pc3.1DNA), producing βHCG6.

mRNA Preparation

For in vitro splicing experiments, βHCG6, β-globin pre-mRNA and different PTM mRNAs were synthesized by in vitro transcription of BamHI and HindIII digested plasmid DNAs respectively, using T7 mRNA polymerase (Pasman & Garcia-Blanco, 1996, Nucleic Acids Res. 24:1638). Synthesized mRNAs were purified by electrophoresis on a denaturing polyacrylamide gel, and the products were excised and eluted.

In Vitro Splicing

PTMs and target pre-mRNA were annealed by heating at 98° C. followed by slow cooling to 30–34° C. Each reaction Reverse Transcription-PCR Reactions RT-PCR analysis was performed using EZ-RT PCR kit (Perkin-Elmer, Foster City, Calif.). Each reaction contained 10 ng of cis- or trans-spliced mRNA, or 1–2 μg of total mRNA, 0.1 μl of each 3' and 5' specific primer, 0.3 Memorandum of each dNTP, 1×EZ buffer (50 Memorandum bicine, 115 Memorandum potassium acetate, 4% glycerol, pH 8.2), 2.5 Memorandum magnesium acetate and 5 U of rTth DNA polymerase in a 50 μl reaction volume. Reverse transcription was performed at 60° C. for 45 min followed by PCR amplification of the resulting cDNA as follows: one cycle of initial denaturation at 94° C. for 30 sec, and 25 cycles of denaturation at 94° C. for 18 sec and annealing and extension at 60° C. for 40 sec, followed by a 7 min final extension at 70° C. Reaction products were separated by electrophoresis in agarose gels.

Primers used in the study were as follows:
DT-1F: GGCGCTGCAGGGCGCTGATGATGTTGTTG SEQ ID NO: 19
DT-2R: GGCGAAGCTTGGATCCGACACGATTTC-CTGCACAGG SEQ ID NO: 20
DT-3R: CATCGTCATAATTTCCTTGTG SEQ ID NO: 21
DT-4R: ATGGAATCTACATAACCAGG SEQ ID NO: 22
DT-5R: GAAGGCTGAGCACTACACGC SEQ ID NO: 23
HCG-R2: CGGCACCGTGGCCGAAGTGG, SEQ ID NO: 24
Bio-HCG-F: ACCGGAATTCATGAAGCCAGGTACAC-CAGG SEQ ID NO: 25

β-globulin-F: GGGCAAGGTGAACGTGGATG SEQ ID NO: 26

β-globulin-R: ATCAGGAGTGGACAGATCC SEQ ID NO: 27

Cell Growth, Transfection and mRNA Isolation

Human lung cancer cell line H1299 (ATCC accession # CRL-5803) was grown in RPMI medium supplemented with 10% fetal bovine serum at 37° C. in a 5% $CO_2$ environment. Cells were transfected with pcSp+CRM (CRM is a non-functional toxin), a vector expressing a PTM, or vector alone (pcDNA3.1) using lipofectamine reagent (Life Technologies, Gaithersburg, Md.). The assay was scored for neomycin resistance ($neo^r$) colony formation two weeks after transfection. Four $neo^3$ colonies were selected and expanded under continued neo selection. Total cellular mRNA was isolated using RNA exol (BioChain Institute, Inc., San Leandro, Calif.) and used for RT-PCR.

Trans-Splicing in Tumors in Nude Mice

Eleven nude mice were bilaterally injected (except B10, B11 and B12 had 1 tumor) into the dorsal flank subcutaneous space with $1 \times 10^7$ H1299 human lung tumor cells (day 1). On day 14, the mice were given an appropriate dose of anesthesia and injected with, or without electroporation (T820, BTX Inc., San Diego, Calif.) in several orientations with a total volume of 100 μl of saline containing 100 μg pcSp+CRM with or without pcβHCG6 or pcPTM+Sp. Solutions injected into the right side tumors also contained India ink to mark needle tracks. The animals were sacrificed 48 hours later and the tumor excised and immediately frozen at −80° C. For analysis, 10 mg of each tumor was homogenized and mRNA was isolated using a Dynabeads mRNA direct kit (Dynal) following the manufacturers directions. Purified mRNA (2 μl of 10 μl total volume) was subjected to RT-PCR using βHCG-F and DT-5R primers as described earlier. All samples were re-amplified using DT-3R, a nested DT-A primer and biotinylated βHCG-F and the products were analyzed by electrophoresis on a 2% agarose gel. Samples that produced a band were processed into single stranded DNA using M280 Streptavidin Dynabeads and sequenced using a toxin specific primer (DT-3R).

Results

Synthesis of PTM

Figure 1C:
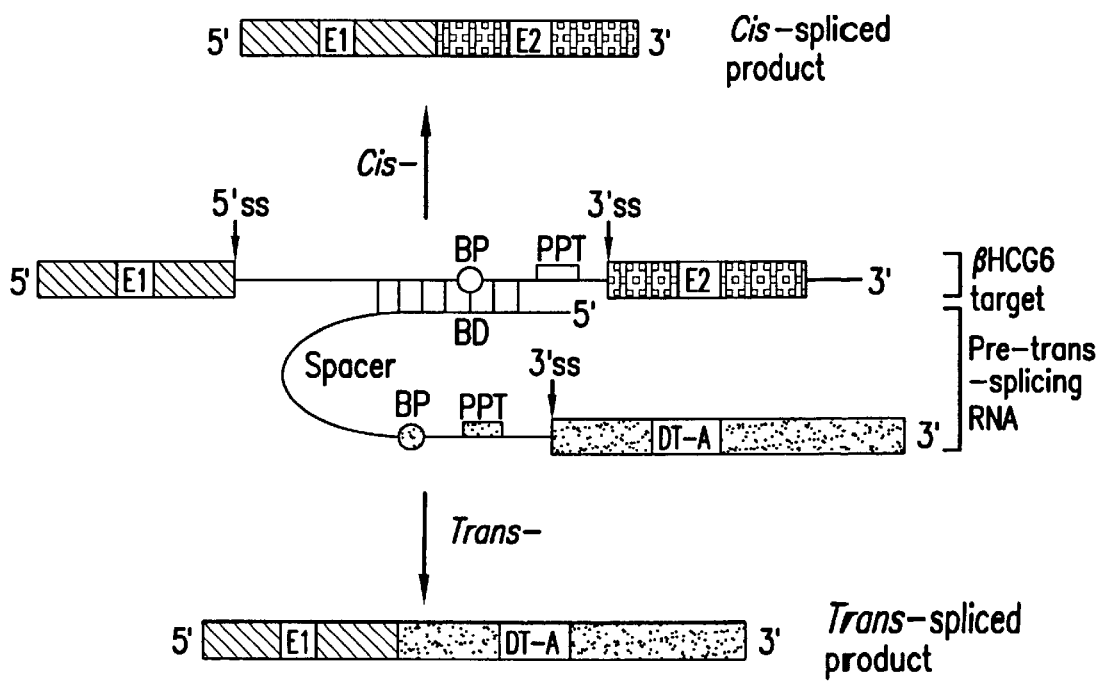
FIG. 1C. Schematic drawing showing the binding of PTM+Sp via conventional Watson Crick base pairing to the βHCG6 target pre-mRNA and the proposed cis- and trans-splicing mechanism.

A prototypical trans-splicing mRNA molecule, pcPTM+Sp (FIG. 1A) was constructed that included: an 18 nt target binding domain (complementary to βHCG6 intron 1), a 30 nucleotide spacer region, branch point (BP) sequence, a polypyrimidine tract (PPT) and an AG dinucleotide at the 3' splice site immediately upstream of an exon encoding diphtheria toxin subunit A (DT-A) (Uchida et al., 1973, J. Biol. Chem. 248:3838). Later DT-A exons were modified to eliminate translation initiation sites at codon 14. The PTM constructs were designed for maximal activity in order to demonstrate trans-splicing; therefore, they included potent 3' splice elements (yeast BP and a mammalian PPT) (Moore et al., 1993, In The mRNA World, R. F. Gesteland and J. F. Atkins, eds. (Cold Spring Harbor, N.Y.: Cold Spring Harbor Laboratory Press). βHCG6 pre-mRNA (Talmadge et al., 1984, Nucleic Acids Res. 12:8415) was chosen as a model target as this gene is expressed in most tumor cells. It is not expressed in normal adult cells, with the exception of some in the pituitary gland and gonads. (Acevedo et al., 1992, Cancer 76:1467; Hoon et al., 1996, Int J. Cancer 69:369; Bellet et al., 1997, Cancer Res. 57:516). As shown in FIG. 1C, pcPTM+Sp forms conventional Watson-Crick base pairs by its binding domain with the 3' end of βHCG6 intron 1, masking the intronic 3' splice signals of the target. This feature is designed to facilitate trans-splicing between the target and the PTM.

HeLa nuclear extracts were used in conjunction with established splicing procedures (Pasman & Garcia-Blanco, 1996, Nucleic Acids Res. 24:1638) to test if a PTM construct could invade the βHCG6 pre-mRNA target. The products of in vitro trans-splicing were detected by RT-PCR, using primers specific for chimeric mRNA molecules. The predicted product of a successful trans-splicing reaction is a chimeric mRNA comprising the first exon of βHCG6, followed immediately by the exon contributed from pcPTM+Sp encoding DT-A (FIG. 1C). Such chimeric mRNAs were readily detected by RT-PCR using primers βHCG-F (specific to βHCG6 exon 1) and DT-3R (specific to DT-A, FIG. 2, lanes 1–2). At time zero or in the absence of ATP, no 466 bp product was observed, indicating that this reaction was both ATP and time dependent.

Figure 2A:
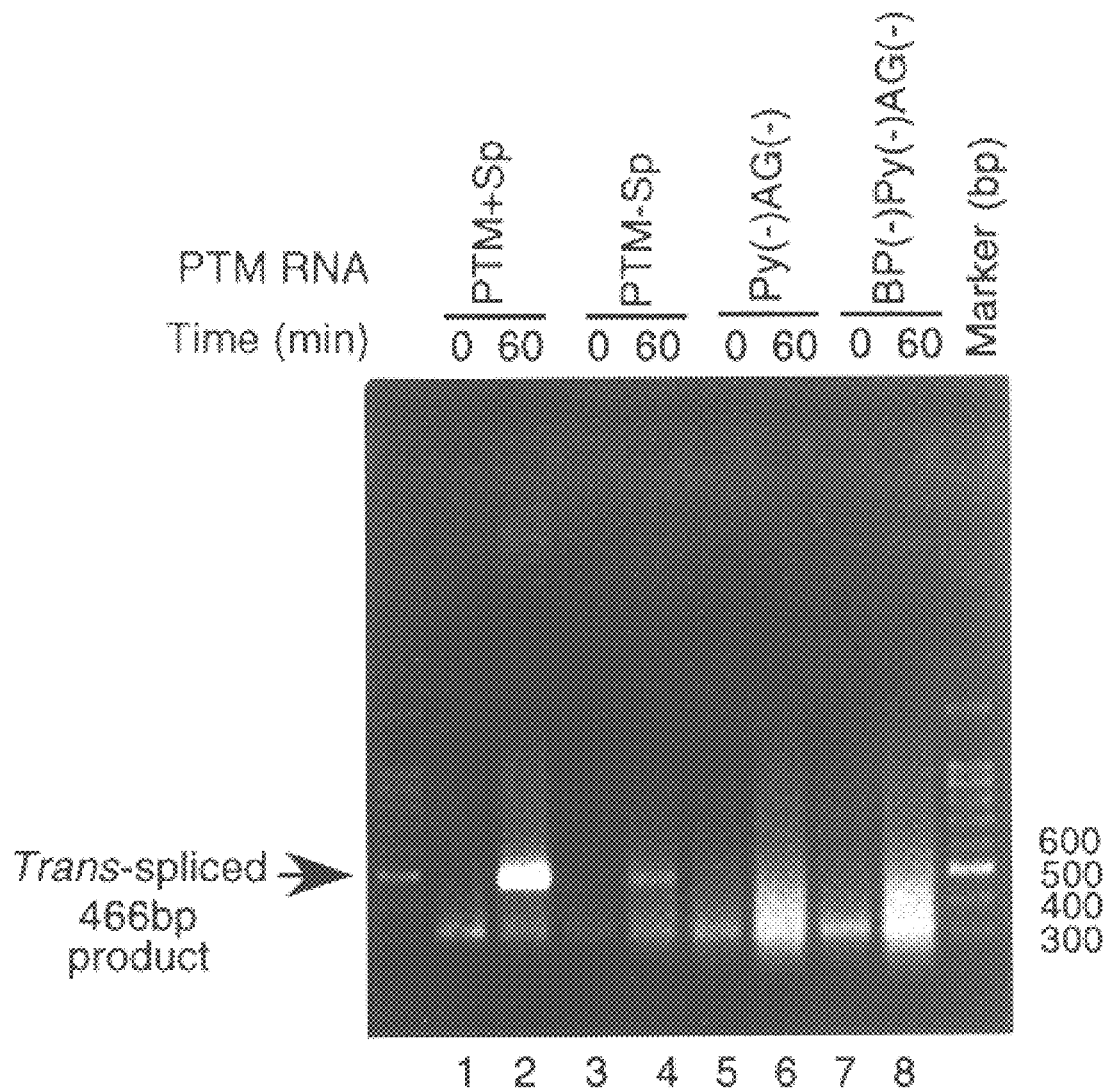
FIG. 2A. In vitro trans-splicing efficiency of various PTM constructs into βHCG6 target. A targeted binding domain and active splice sites correlate with PTM trans-splicing activity. Full length targeted (pcPTM+Sp), non-targeted (PTM–Sp) and the splice mutants [Py(–)AG(–) and BP(–)Py(–)AG(–)] PTM RNAs were added to splicing reactions containing βHCG6 target pre-mRNA. The products were RT-PCR amplified using primers βHCG-F (specific for target βHCG6 exon 1) and DT-5R (complementary to DT-A) and analyzed by electrophoresis in a 1.5% agarose gel.
Figure 2B:
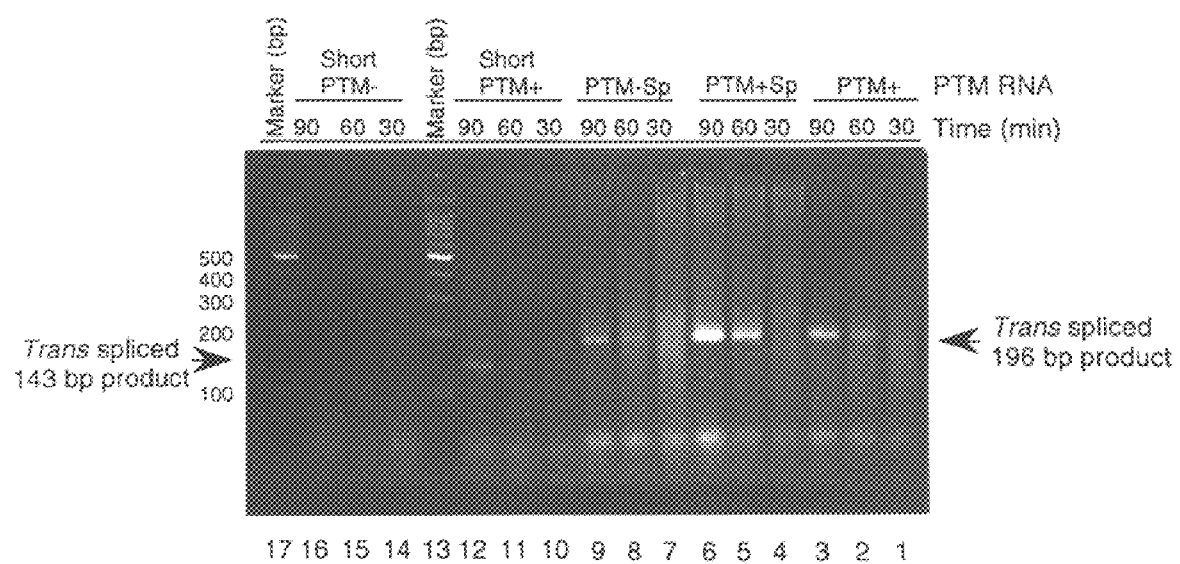
FIG. 2B. In vitro trans-splicing efficiency of various PTM constructs. Full length PTM with a spacer between the binding domain and splice site (PTM+Sp), PTM without the spacer region (PTM+) and short PTMs that contain a target binding domain (short PTM+) or a non-target binding region (PTM–) were added to splicing reactions containing βHCG target pre-mRNA. The products were RT-PCR amplified using primers βHCG-F and DT-3. For reactions containing the short PTMs, the reverse PCR primer was DT-4, since the binding site for DT-3 was removed from the PTM.

The target binding domain of pcPTM+Sp contained 18 nucleotides complementary to βHCG6 intron 1 pre-mRNA and demonstrated efficient trans-splicing (FIG. 2A, lanes 1–2). Trans-splicing efficiency decreased at least 8 fold (FIG. 2, lanes 3–4) using non-targeted PTM–Sp, which contains a non-complementary 18 nucleotide "non-binding domain". Trans-splicing efficiencies of PTM mRNAs with or without a spacer between the binding domain and BP were also compared. This experiment demonstrated a significant increase in the efficiency of trans-splicing by the addition of a spacer (FIG. 2B, lanes 2+5). To facilitate the recruitment of splicing factors required for efficient trans-splicing, some space may be needed between the 3' splice site and the double stranded secondary structure produced by the binding domain/target interaction.

To investigate the effect of PTM length on trans-splicing specificity, shorter PTMs were synthesized from AccI cut PTM plasmid (see FIG. 1). This eliminated 479 nt from the 3' end of the DT-A coding sequence. FIG. 2B shows the trans-splicing ability of a targeted short PTM(+) (lanes 10–12), compared to a non-targeted short PTM(−) (lanes 14–17). Short PTM+produced substantially more trans-spliced product (FIG. 2B, lane 12) than its counterpart, non-targeted short PTM (FIG. 2B, lane 17). These experiments indicate that longer PTMs may have increased potential to mediate trans-splicing non-specifically.

Accuracy of PTM Spliceosome Mediated Trans Splicing

Figure 3:
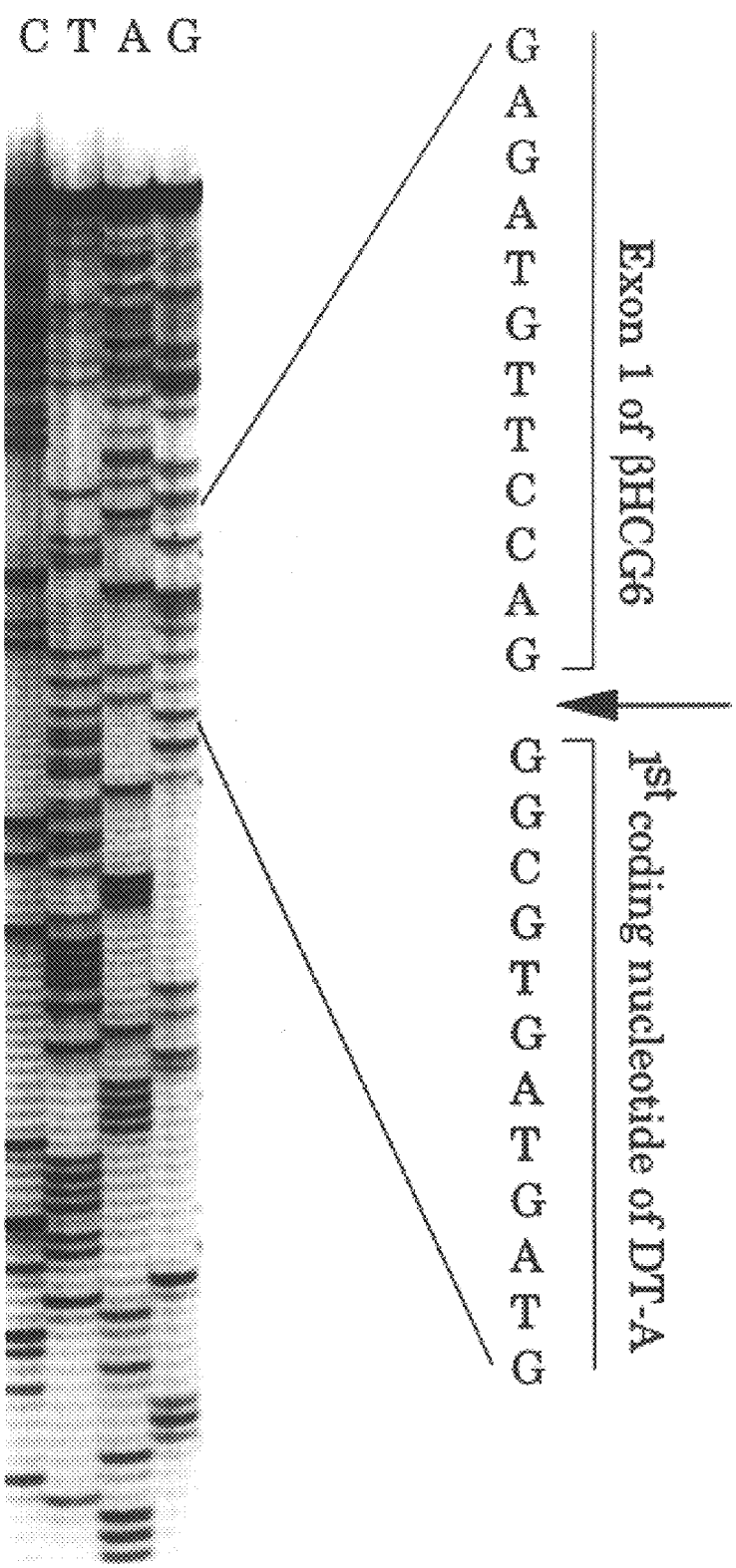
FIG. 3. Nucleotide sequence demonstrating the in vitro trans-spliced product between a PTM and target pre-mRNA (SEQ ID NO:53). The 466 bp trans-spliced RT-PCR product from FIG. 2 (lane 2) was re-amplified using a 5' biotin labeled forward primer (βHCG-F) and a nested unlabeled reverse primer (DT-3R). Single stranded DNA was purified and sequenced directly using toxin specific DT-3R primer. The arrow indicates the splice junction between the last nucleotide of target βHCG6 exon I and the first nucleotide encoding DT-A.

To confirm that trans-splicing between the pcPTM+Sp and βHCG6 target is precise, RT-PCR amplified product was produced using 5' biotinylated βHCG-F and nonbiotinylated DT-3R primers. This product was converted into single stranded DNA and sequenced directly with primer DT-3R (DT-A specific reverse primer) using the method of Mitchell and Merril (1989, Anal. Biochem. 178:239). Trans-splicing occurred exactly between the predicted splice sites (FIG. 3), confirming that a conventional pre-mRNA can be invaded by an engineered PTM construct during splicing; moreover, this reaction is precise.

Figure 8A:
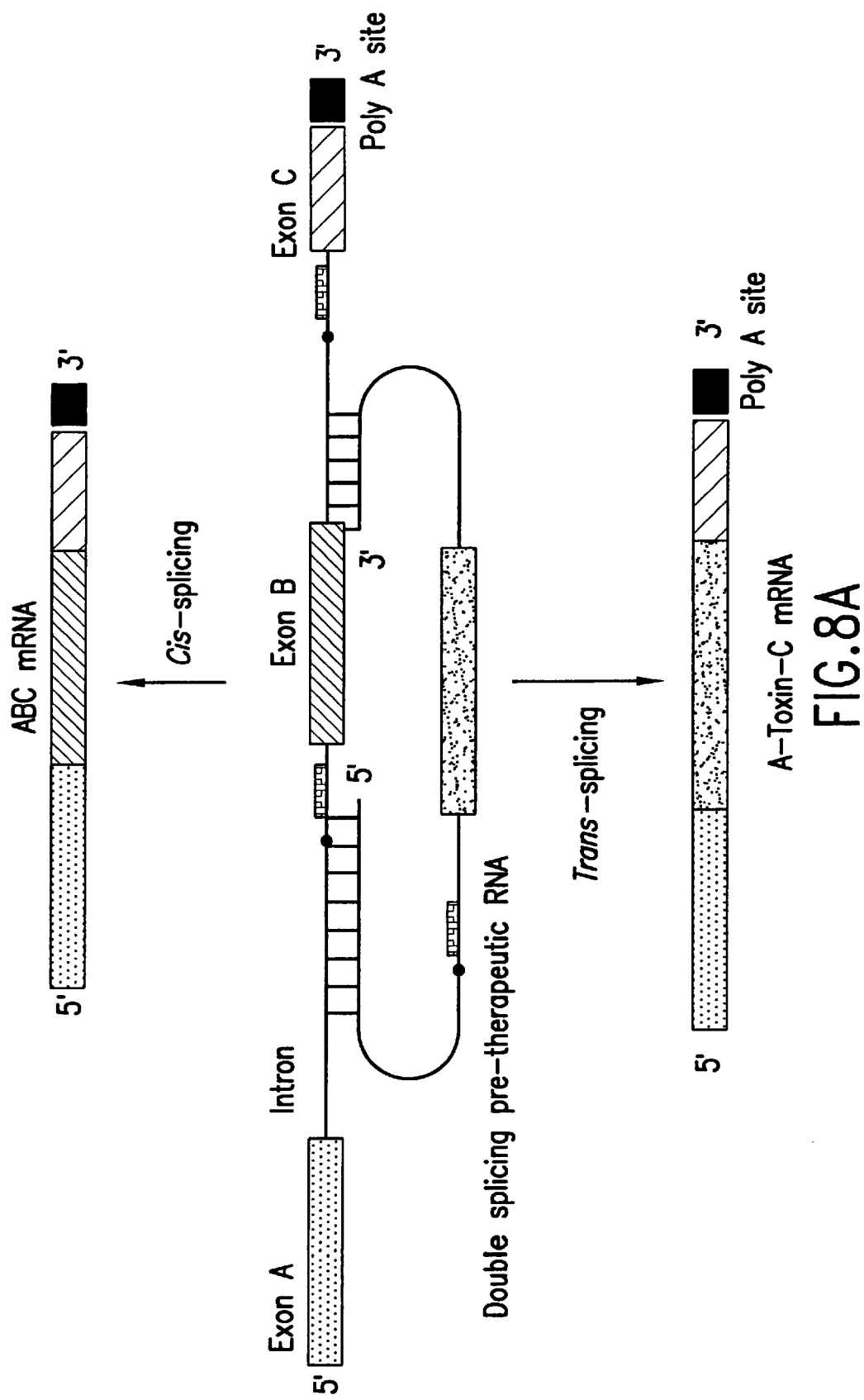
Figure 8B:
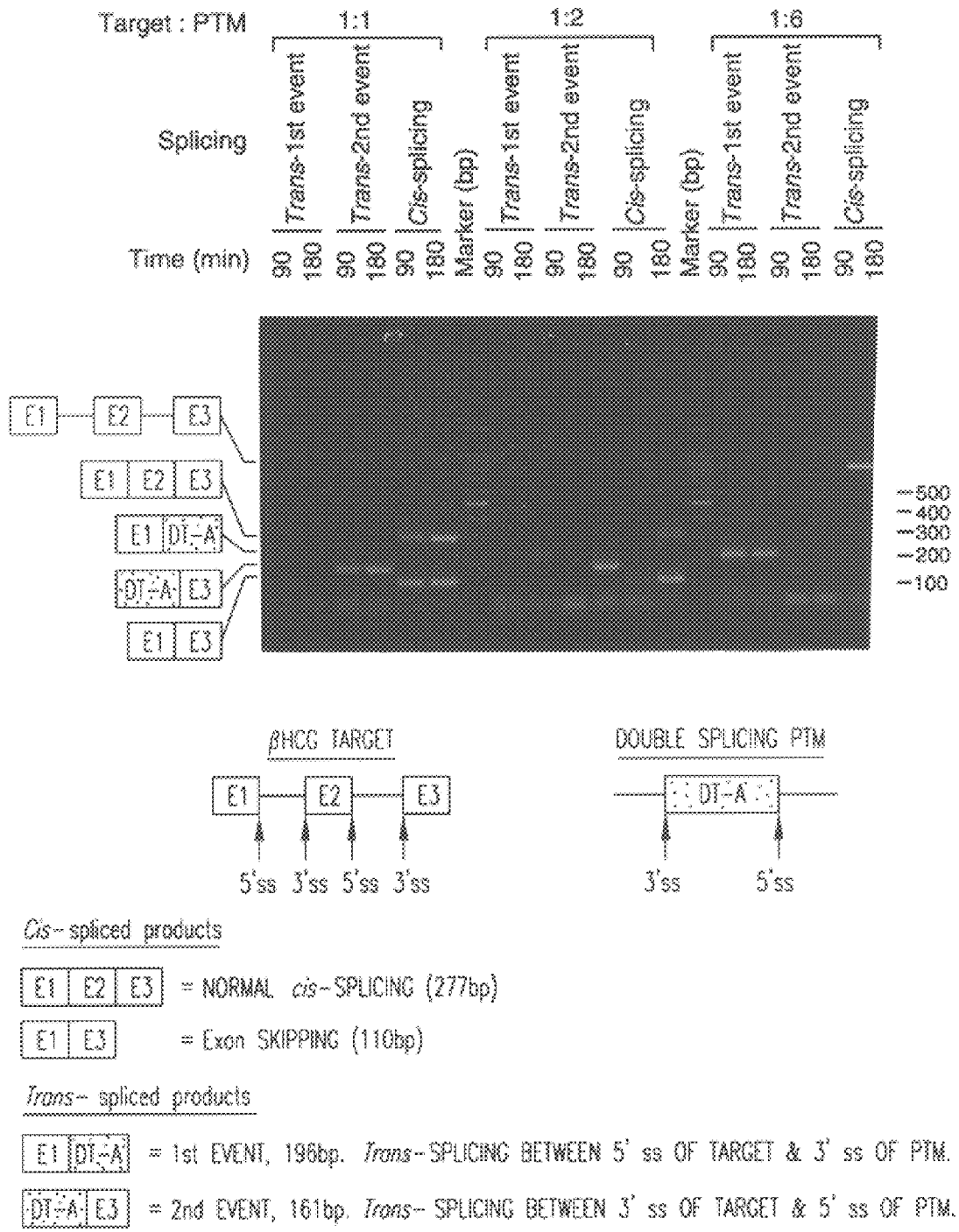

In addition selective trans-splicing of a double splicing PTM (DS-PTM) was observed (FIG. 8B). The DS-PTM can produce trans-splicing by contributing either a 3' or 5' splice site. Further, DS-PTMs can be constructed which will be capable of simultaneously double trans-splicing, at both a 3' and 5' site, thereby permitting exon replacement. FIG. 8B demonstrates that in this construct the 5' splice site is most active at a 1:1 concentration of target βHCG pre-mRNA:DS-PTM. At a 1:6 ratio the 3' splice site is more active.

Slice Sites are Essential for PTM Trans-Splicing

In general, the 3' splice site contains three elements: 1) a BP sequence located 5' of the acceptor site, 2) a PPT consisting of a short run of pyrimidine residues, and 3) a YAG trinucleotide splice site acceptor at the intron-exon border (Senapathy et al., 1990, Cell 91:875; Moore et al., 1993). Deletion or alteration of one of these sequence elements are known to either decrease or abolish splicing (Aebi et al., 1986; Reed & Maniatis 1988, Genes Dev. 2:1268; Reed, 1989, Genes Dev. 3:2113; Roscigno et al., 1993, J. Biol. Chem. 268:11222; Coolidge et al., 1997, Nucleic Acids Res. 25:888). The role of these conserved elements in targeted trans-splicing was addressed experimentally. In one case [(BP(-)Py(-)AG(-)], all three cis elements (BP, PPT and AG dinucleotide) were replaced by random sequences. A second splicing mutant [(Py(-)AG(-)] was constructed in which the PPT and the 3' splice site acceptor were mutated and substituted by random sequences. Neither construct was able to support trans-splicing in vitro (FIG. 2A, lanes 5–8), suggesting that, as in the case of conventional cis-splicing, the PTM trans-splicing process also requires a functional BP, PPT and AG acceptor at the 3' splice site.

Development of a "Safety" Splice Site to Increase Specificity

Figure 4A:
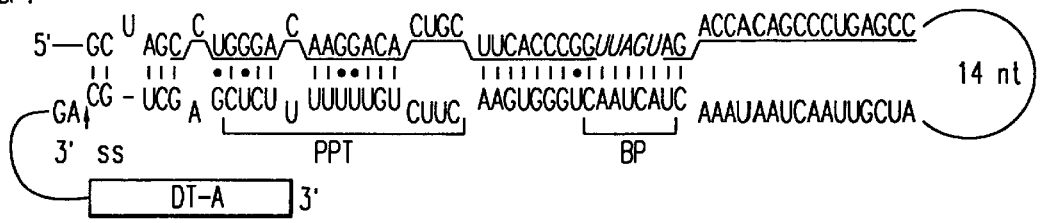
FIG. 4A. Schematic diagram of the "safety" PTM and variations, demonstrating the PTM intramolecular base-paired stem, intended to mask the BP and PPT from splicing factors (SEQ splice acceptor site and/or a 5' splice donor site; and a spacer region that separates the RNA splice site from the target binding domain. In addition, the PTMs of the invention can be engineered to contain any nucleotide sequences encoding a translatable protein product.
Figure 4A:
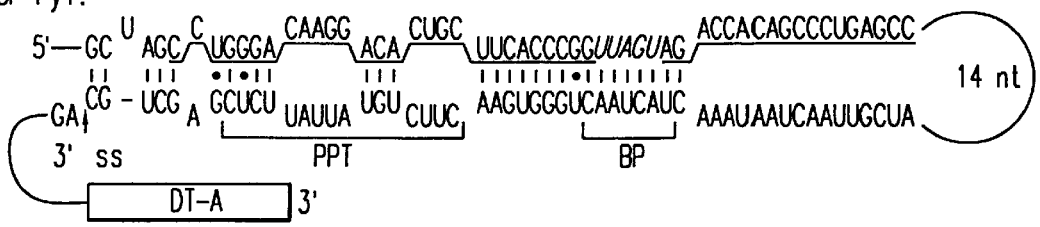
Figure 4A:
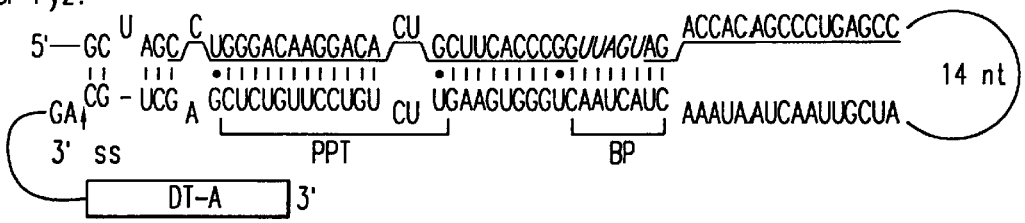
Figure 4B:
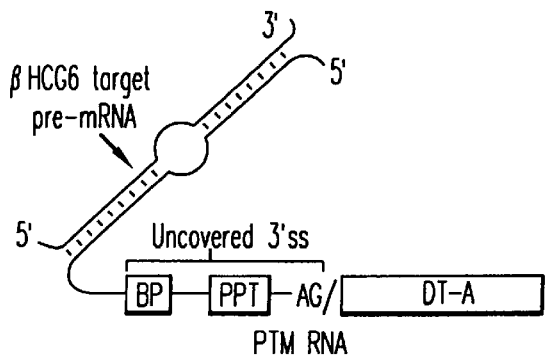

To improve the levels of target specificity achieved by the inclusion of a binding domain or by shortening the PTM, the target-binding domain of several PTM constructs was modified to create an intra-molecular stem to mask the 3' splice site (termed a "safety PTM"). The safety stem is formed by portions of the binding domain that partially base pair with regions of the PTM 3' splice site or sequences adjacent to them, thereby blocking the access of spliceosomal components to the PTM 3' splice site prior to target acquisition (FIG. 4A, PTM+SF). Base pairing between free portions of the PTM binding domain and βHCG6 target region unwinds the safety stem, allowing splicing factors such as U2AF to bind to the PTM 3' splice site and initiate trans-splicing (FIG. 4B).

This concept was tested in splicing reactions containing either PTM+SF (safety) or pcPTM+Sp (linear), and both target (βHCG6) and non-target (β-globin) pre-mRNA. The spliced products were subsequently analyzed by RT-PCR and gel electrophoresis. Using βHCG-F and DT-3R primers, the specific 196 bp trans-spliced band was demonstrated in reactions containing βHCG target and either linear PTM (pcPTM+Sp, FIG. 5, lane 2) or safety PTM (PTM+SF, FIG. 5, lane 8). Comparison of the targeted trans-splicing between linear PTM (FIG. 5, lane 2) and safety PTM (FIG. 5, lane 8) demonstrated that the safety PTM trans-spliced less efficiently than the linear PTM.

Figure 5:
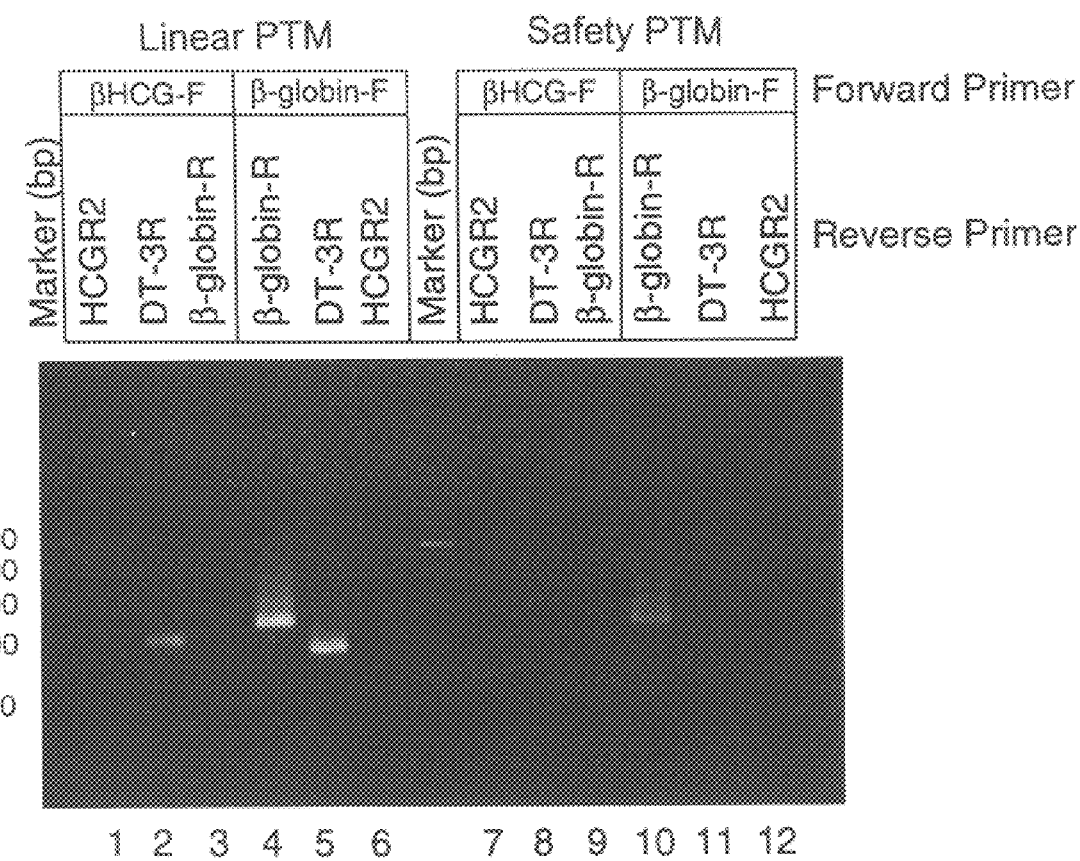

Non-targeted reactions were amplified using β-globin-F (specific to exon 1 of β-globin) and DT-3R primers. The predicted product generated by non-specific PTM trans-splicing with β-globin pre-mRNA is 189 bp. Non-specific trans-splicing was evident between linear PTM and β-globin pre-mRNA (FIG. 5, lane 5). In contrast, non-specific trans-splicing was virtually eliminated by the use of safety PTM (FIG. 5, lane 11). This was not unexpected, since the linear PTM was designed for maximal activity to prove the concept of spliceosome-mediated trans-splicing. The open structure of the linear PTM combined with its potent 3' splice sites strongly promotes the binding of splicing factors. Once bound, these splicing factors can potentially initiate trans-splicing with any 5' splice site, in a process similar to trans-splicing in trypanosomes. The safety stem was designed to prevent splicing factors, such as U2AF from binding to the PTM prior to target acquisition. This result is consistent with a model that base-pairing between the free portion of the binding domain and the βHCG6 target unwinds the safety stem (by mRNA-mRNA interaction), uncovering the 3' splice site, permitting the recruitment of splicing factors and initiation of trans-splicing. No trans-splicing was detected between β-globin and βHCG6 pre-mRNAs (FIG. 5, lanes 3, 6, 9 and 12).

In Vitro Trans-Splicing of Safety PTM and Variants

Figure 4C:
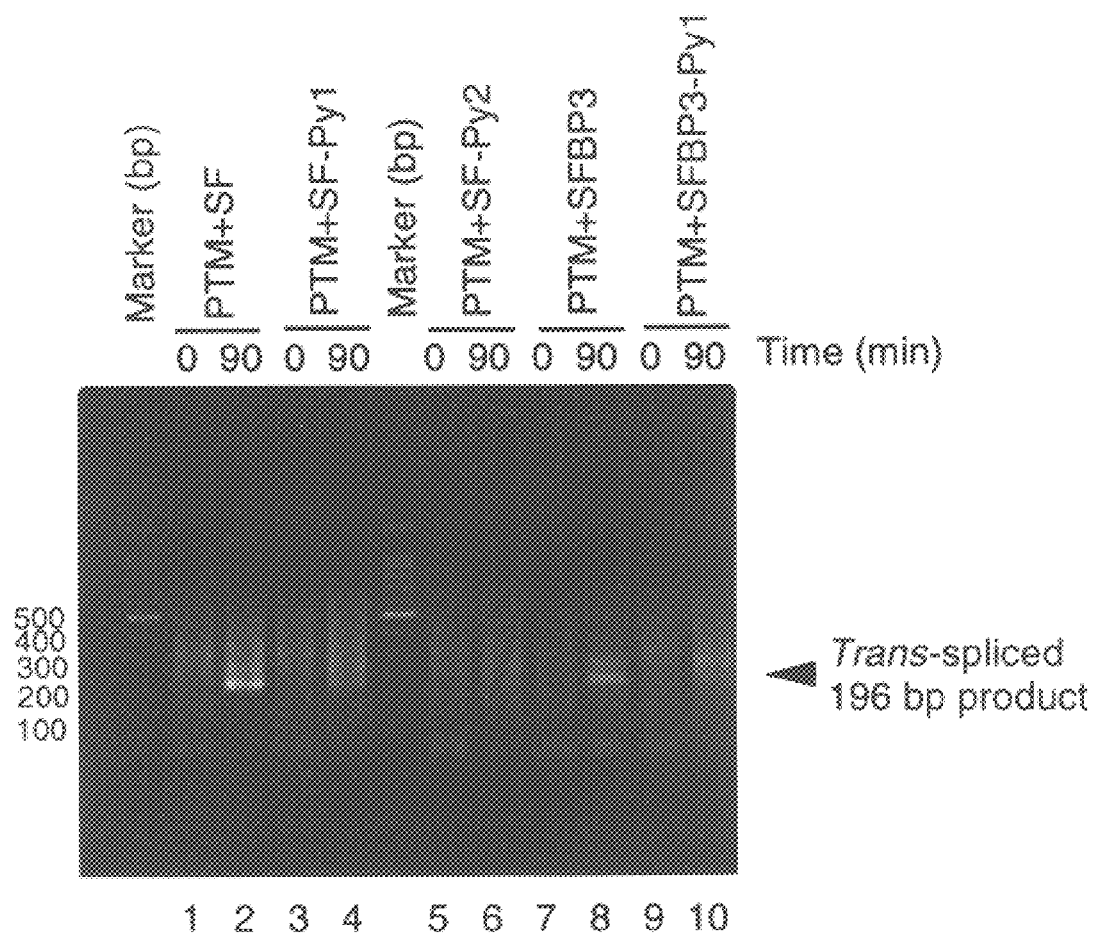

To better understand the role of cis-elements at the 3' splice site in trans-splicing a series of safety PTM variants were constructed in which either the PPT was weakened by substitution with purines and/or the BP was modified by base substitution (see Table I). In vitro trans-splicing efficiency of the safety (PTM+SF) was compared to three safety variants, which demonstrated a decreased ability to trans-splice. The greatest effect was observed with varient 2 (PTM+SFPy2), which was trans-splicing incompetent (FIG. 4C, lanes 5–6). This inhibition of trans-splicing may be attributed to a weakened PPT and/or the higher $T_m$ of the safety stem. In contrast, variations in the BP sequence (PTM+SFBP3) did not markedly effect trans-splicing (FIG. 4C, lanes 7–8). This was not surprising since the modifications introduced were within the mammalian branch point consensus range YNYURAC (where Y=pyrimidine, R=purine and N=any nucleotide) (Moore et al., 1993). This finding indicates that the branch point sequence can be removed without affecting splicing efficiency. Alterations in the PPT (PTM+SF−Py1) decreased the level of trans-splicing (lanes 3–4). Similarly, when both BP and PPT were altered PTM+SFBP3−Py1, they caused a further reduction in trans-splicing (FIG. 4C, lanes 9–10). The order of trans-splicing efficiency of these safety variants is PTM+SF>PTM+SFBP3>PTM+SFPy1>PTM+SFBP3−Py1>PTM+SFPy2. These results confirm that both the PPT and BP are important for efficient in vitro trans-splicing (Roscigno et al., 1993, J. Biol. Chem. 268:11222).

Competition Between Cis- and Trans-Splicing

Figure 6A:
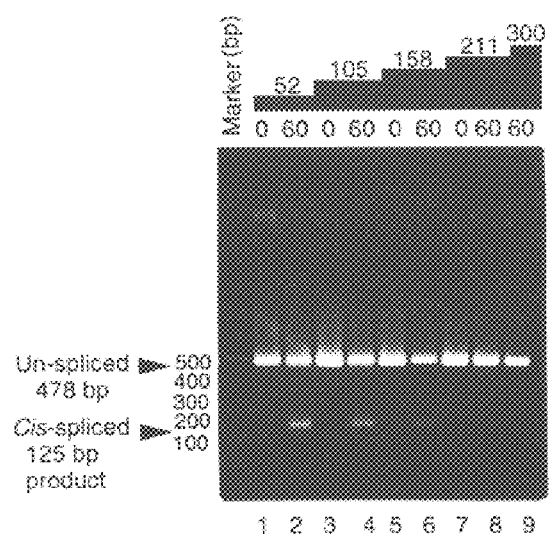
Figure 6B:
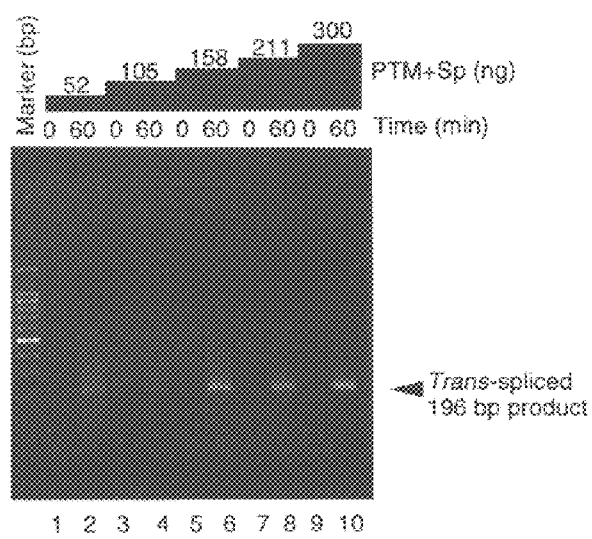

To determine if it was possible to block pre-mRNA cis-splicing by increasing concentrations of PTM, experiments were performed to drive the reaction towards trans-splicing. Splicing reactions were conducted with a constant amount of βHCG6 pre-mRNA target and various concentrations of trans-splicing PTM. Cis-splicing was monitored by RT-PCR using primers to βHCG-F (exon 1) and βHCG-R2 (exon 2). This amplified the expected 125 bp cis-spliced and 478 bp unspliced products (FIG. 6A). The primers βHCG-F and DT-3R were used to detect trans-spliced products (FIG. 6B). At lower concentrations of PTM, cis-splicing (FIG. 6A, lanes 1–4) predominated over trans-splicing (FIG. 6B, lanes 1–4). Cis-splicing was reduced approximately by 50% at a PTM concentration 1.5 fold greater than target. Increasing the PTM mRNA concentration to 3 fold that of target inhibited cis-splicing by more than 90% (FIG. 6A, lanes 7–9), with a concomitant increase in the trans-spliced product (FIG. 6B, lanes 6–10). A competitive RT-PCR was performed to simultaneously amplify both cis and trans-spliced products by including all three primers (βHCG-F, HCG-R2 and DT-3R) in a single reaction. This experiment had similar results to those seen in FIG. 6, demonstrating that under in vitro conditions, a PTM can effectively block target pre-mRNA cis-splicing and replace it with the production of an engineered trans-spliced chimeric mRNA.

Trans-Splicing in Tissue Culture

Figure 7A:
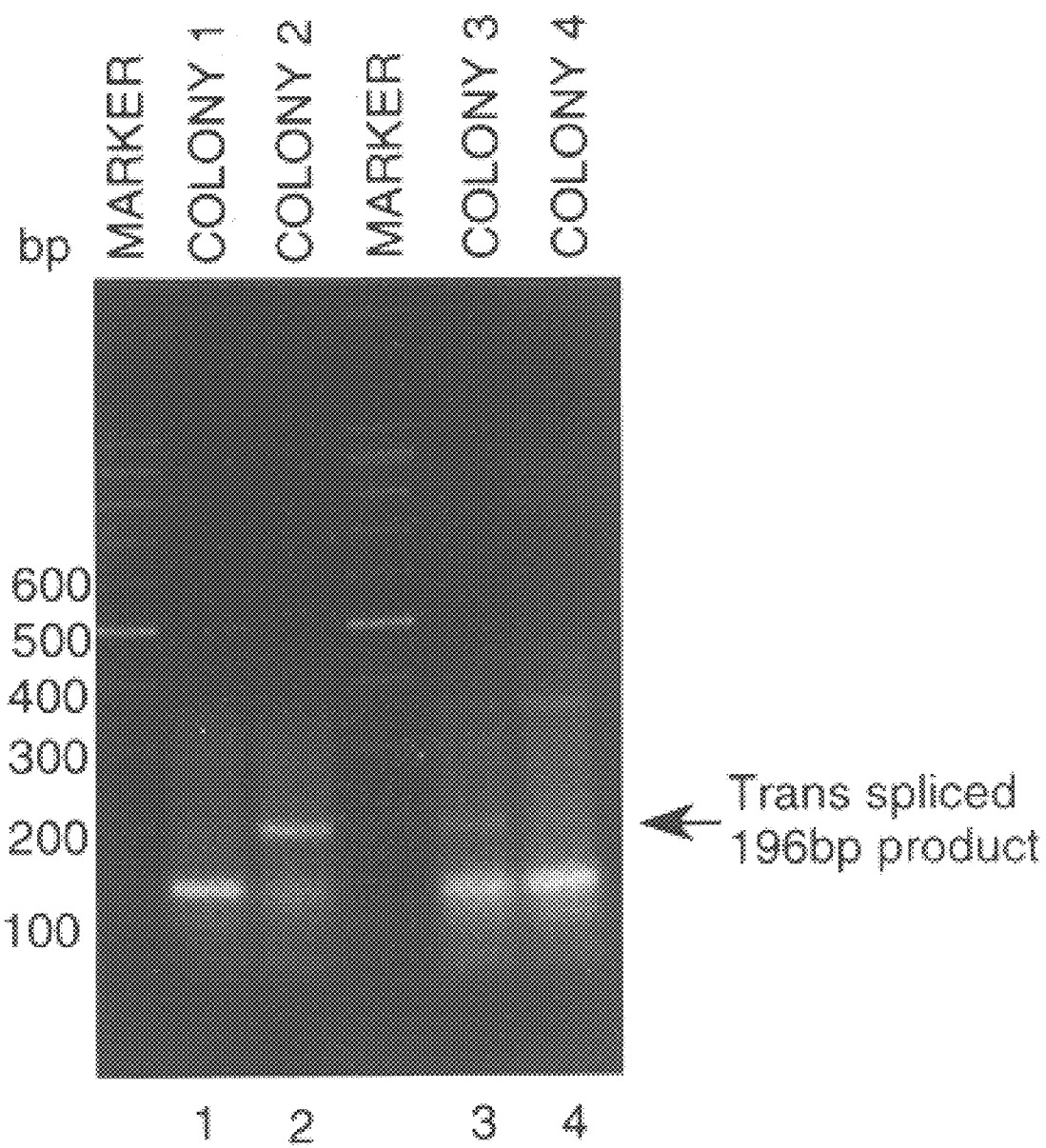

To demonstrate the mechanism of trans-splicing in a cell culture model, the human lung cancer line H1299 (βHCG6 positive) was transfected with a vector expressing SP+CRM (a non-functional diphtheria toxin) or vector alone (pcDNA3.1) and grown in the presence of neomycin. Four neomycin resistant colonies were individually collected after 14 days and expanded in the continued presence of neomycin. Total mRNA was isolated from each clone and analyzed by RT-PCR using primers βHCG-F and DT-3R. This yielded the predicted 196 bp trans-spliced product in three out of the four selected clones (FIG. 7A, lanes 2, 3 and 4). The amplified product from clone #2 was directly sequenced, confirming that PTM driven trans-splicing occurred in human cells exactly at the predicted splice sites of endogenously expressed βHCG6 target exon 1 and the first nucleotide of DT-A (FIG. 7B).

Trans-Splicing in an In Vivo Model

To demonstrate the mechanism of trans-splicing in vivo, the following experiment was conducted in athymic (nude) mice. Tumors were established by injecting 10^7 H1299 cells into the dorsal flank subcutaneous space. On day 14, PTM expression plasmids were injected into tumors. Most tumors were then subjected to electroporation to facilitate plasmid delivery (see Table 2, below). After 48 hrs, tumors were removed, poly-A mRNA was isolated and amplified by RT-PCR. Trans-splicing was detected in 8 out of 19 PTM treated tumors. Two samples produced the predicted trans-spliced product (466 bp) from mRNA after one round of RT-PCR. Six additional tumors were subsequently positive for trans-splicing by a second PCR amplification using a nested set of primers that produced the predicted 196 bp product (Table 2). Each positive sample was sequenced, demonstrating that βHCG6 exon 1 was precisely trans-spliced to the coding sequence of DT-A (wild type or CRM mutant) at the predicted splice sites. Six of the positive samples were from treatment groups that received cotransfected plasmids, pcPTM+CRM and pcHCG6, which artificially increased the concentration of target pre-mRNA. This was done to enhance the probability of detecting trans-spliced events. The other two positive tumors were from a group that received only pcPTM+Sp (wild type DT-A). These tumors were not transfected with βHCG6 expression plasmid, demonstrating once again, as in the tissue culture model described in Section 6.2.7, that trans-splicing occurred between the PTM and endogenous βHCG6 pre-mRNA produced by tumor cells.

TABLE 2

Trans-splicing in tumors in nude mice

| Group | Plasmid | Tumor Left | Tumor Right | Electroporation | RT-PCR (For 466 bp) Left | RT-PCR (For 466 bp) Right | Nested PCR (For 196 bp) | Splice junction sequence |
|---|---|---|---|---|---|---|---|---|
| [1]B1 | pCMV – Sport | B1-1 | B1-2 | – | – | – | – | – |
| B2 | pCMV – Sport | B1-3 | B1-4 | [a]1000 V/cm | – | – | – | – |
| B3 | pcSp + CRM | B3-1 | B3-2 | [a]1000 V/cm | – | – | – | – |
|  |  | B3-3 | B3-4 | [a]1000 V/cm | – | – | – | – |
| B4 | pcSp + CRM | B4-1 | B4-2 | [b]50 V/cm | – | – | – | – |
|  |  | B4-3 | B4-4 | [c]25 V/cm | – | – | – | – |
| B5 | pcSp + CRM/ pcHCG6 | B5-1 | B5-2 | [a]1000 V/cm | + | – | + | + ATGTTCCAG↓GGCGTGATGAT (SEQ ID NO: 65) |
|  |  | B5-3 | B5-4 | [a]1000 V/cm | + | – | + | + ATGTTCCAG↓GGCGTGATGAT (SEQ ID NO: 65) |
| B6 | pcSp + CRM/ pcHCG6 | B6-1 | B6-2 | [b]50 V/cm | – | – | – | – |
|  |  | B6-3 | B6-4 | [c]25 V/cm | – | – | + | + ATGTTCCAG↓GGCGTGATGAT (SEQ ID NO: 65) |
| B7 | pc PTM + Sp | B7-1 |  | [a]1000 V/cm | – | – | – |  |
| B8 | pc PTM + Sp | B8-1 |  | [b]50 V/cm | – | + |  | ATGTTCCAG↓GGCGTGATGAT (SEQ ID NO: 65) |
| [1]B9 | pc PTM + Sp | B9-1 |  | – | – | + |  | ATGTTCCAG↓GGCGTGATGAT (SEQ ID NO: 65) |

[a]6 pulses of 99 μs sets of 3 pulses administered orthogonally
[b]8 pulses of 10 ms sets of 4 pulses administered orthogonally
[c]8 pulses of 50 ms sets of 4 pulses administered orthogonally
[1]did not receive electroporation

EXAMPLE lacZ Trans-Splicing Model

In order to demonstrate and evaluate the generality of the mechanism of spliceosome mediated targeted trans-splicing between a specific pre-mRNA target and a PTM, a simple model system based on expression of enzyme β-galactosidase was developed. The following section describes results demonstrating successful splicesome mediated targeted trans-splicing between a specific target and a PTM.

Materials and Methods

Primer Sequences

The following primers were used for testing the lacZ model system:

5' Lac-1F GCATGAATTCGGTACCATGGGGGGGT-TCTCATCATCATC SEQ ID NO: 28
5' Lac-1R CTGAGGATCCTCTTACCTGTAAACGC-CCATACTGAC SEQ ID NO: 29
3' Lac-1F GCATGGTAACCCTGCAGGGCGGCT-TCGTCTGGGACTGG SEQ ID NO: 30
3' Lac-1R CTGAAAGCTTGTTAACTTAT-TATTTTTGACACCAGACC SEQ ID NO: 31
3' Lac-Stop GCATGGTAACCCTGCAGGGCGGCT-TCGTCTAATAATGGGACTGGGTG SEQ ID NO: 32
HCG-In1F GCATGGATCCTCCGGAGGGC-CCCTGGGCACCTTCCAC SEQ ID NO: 33
HCG-In1R CTGACTGCAGGGTAACCGGACAAGGA-CACTGCTTCACC SEQ ID NO: 34
HCG-Ex2F GCATGGTAACCCTGCAGGGGCTGCTGCT-GTTGCTG SEQ ID NO: 35
HCG-Ex2R CTGAAAGCTTGTTAACCAGCTCAC-CATGGTGGGGCAG SEQ ID NO: 36
Lac-TR1 (Biotin): 7-GGCTTTCGCTACCTGGAGAGAC SEQ ID NO: 37
Lac-TR2 GCTGGATGCGGCGTGCGGTCG SEQ ID NO: 38
HCG-R2: CGGCACCGTGGCCGAAGTGG SEQ ID NO: 39

Construction of the lacZ Pre-mRNA Target Molecule

The lacZ target 1 pre-mRNA (pc3.1 lacT1) was constructed by cloning of the following three PCR products: (i) the 5' fragment of lacZ; followed by (ii) βHCG6 intron 1; (iii) and the 3' fragment of lacZ. The 5' and 3' fragment of the lacZ gene were PCR amplified from template pcDNA3.1/His/LacZ (Invitrogen, San Diego, Calif.) using the following primers: 5' Lac-1F and 5' Lac-1R (for 5' fragment), and 3' Lac-1F and 3' Lac-1R (for 3' fragment). The amplified lacZ 5 fragment is 1788 bp long which includes the initiation codon, and the amplified 3' fragment is 1385 bp long and has the natural 5' and 3' splice sites in addition to a branch point, polypyrimidine tract and βHCG6 intron 1. The βHCG6 intron 1 was PCR amplified using the following primers: HCG-In1F and HCG-In1R.

The lacZ target 2 is an identical version of lacZ target 1 except it contains two stop codons (TAA TAA) in frame four codons after the 3' splice site. This was created by PCR amplification of the 3' fragment (lacZ) using the following primers: 3' Lac-Stop and 3' Lac 1R and replacing the functional 3' fragment in LacZ target 1.

Construction of pc3.1 PTM1 and pc3.1 PTM2

The pre-trans-splicing molecule, pc3.1 PTM1 was created by digesting pPTM+Sp with PstI and HindIII and replacing the DNA fragment encoding the DT-A toxin with the a DNA fragment encoding the functional 3' end of lacZ. This fragment was generated by PCR amplification using the following primers: 3' Lac-1F and 3' Lac-1R. For cell culture experiments, an EcoRI and HindIII fragment of pc3.1 PTM2 which contains the binding domain to HCG intron 1, a 30 bp spacer, a yeast branch point (TACTAAC), and strong polypyrimidine tract followed by the lacZ cloned was cloned into pcDNA3.1.

The pre-trans-splicing molecule, pc3.1 PTM2 was created by digesting pPTM+Sp with PstI and HindIII and replacing the DNA fragment encoding the DT-A toxin with the βHCG6 exon 2. βHCG6 exon 2 was generated by PCR amplification using the following primers: HCG-Ex2F and HCG-Ex2R. For cell culture experiments, an EcoRI and HindIII fragment of pc3.1 PTM2 which contains the binding domain to HCG intron 1, a 30 bp spacer, a yeast branch point (TACTAAC), and strong polypyrimidine tract followed by the βHCG6 exon 2 cloned was used.

Co-Transfection of the lacZ Splice Target Pre-mRNA and PTMS into 293T Cells

Human embryonic kidney cells (293T) were grown in DMEM medium supplemented with 10% FBS at 37° C. in a 5% $CO_2$. Cells were co-transfected with pc3.1 LacT1 and pc3.1 PTM2, or pc3.1 LacT2 and pc3.1 PTM, using Lipofectamine Plus (Life Technologies, Gaithersburg, Md.) according to the manufacturer's instructions. 24 hours post-transfection, the cells were harvested; total RNA was isolated and RT-PCR was performed using specific primers for the target and PTM molecules. β-galactosidase activity was also monitored by staining the cells using a β-gal staining kit (Invitrogen, San Deigo, Calif.).

Results

Figure 12A:
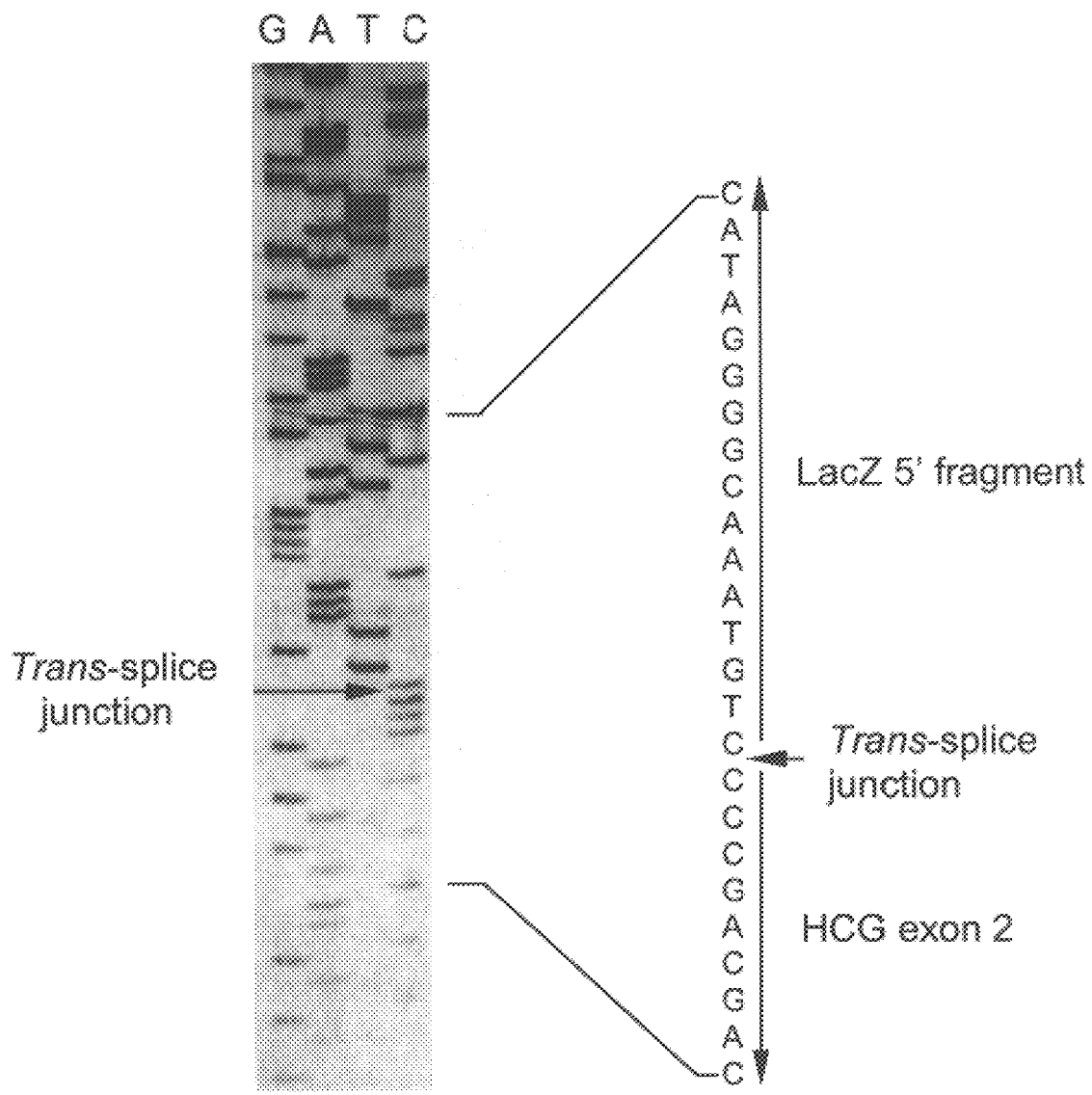

The lacZ Splice Target Cis-Splices Efficiently to Produce Functional β-Galactosidase To test the ability of the splice target pre-mRNA to cis-splice efficiently, pc3.1 lacT1 was transfected into 293 T cells using Lipfectamine Plus reagent (Life Technologies, Gaithersburg, Md.) followed by RT-PCR analysis of total RNA. Sequence analysis of the cis-spliced RT-PCR product indicated that splicing was accurate and occurred exactly at the predicted splice sites (FIG. 12B). In addition, accurate cis-splicing of the target pre-mRNA molecule results in formation of a mRNA capable of encoding active β-galactosidase which catalyzes the hydrolysis of β-galactosidase, i.e., X-gal, producing a blue color that can be visualized under a microscope. Accurate cis-splicing of the target pre-mRNA was further confirmed by successfully detecting β-galactosidase enzyme activity.

Repair of defective lacZ target 2 pre-mRNA by trans-splicing of the functional 3' lacZ fragment (PTM1) was measured by staining for β-galactosidase enzyme activity. For this purpose, 293T cells were co-transfected with lacZ target 2 pre-mRNA (containing a defective 3' fragment) and PTM1 (containing functional 3' lacZ activity). 24 hours post-transfection cells were assayed for β-galactosidase enzyme activity. Efficient trans-splicing of PTM1 into the lacZ target 2 pre-mRNA will result in the production of functional β-galactosidase activity. As demonstrated in FIG. 11B–E, trans-splicing of PTM 1 into lacZ target 2 results in restoration of β-galactosidase enzyme activity up to 5% to 10% compared to control.

Targeted Trans-Splicing Between the lacZ Target Pre-mRNA and PTM2.

To assay for trans-splicing, lacZ target pre-mRNA and PTM2 were transfected into 293 T cells. Following transfection, total RNA was analyzed using RT-PCR. The following primers were used in the PCR reactions: lacZ-TR1 (lacZ 5' exon specific) and HCGR2 (βHCGR exon 2 specific). The RT PCR reaction produced the expected 195 bp trans-spliced product (FIG. 11, lanes 2 and 3) demonstrating efficient trans-splicing between the lacZ target pre-mRNA and PTM 2. Lane 1 represents the control, which does not contain PTM 2.

The efficiency of the trans-splicing was also measured by staining for β-galactosidase enzyme activity. To assay for trans-splicing, 293T cells were co-transfected with lacZ target pre-mRNA and PTM 2. 24 hours post-transfection, cells were assayed for β-galactosidase activity. If there is efficient trans-splicing between the target pre-mRNA and the PTM, a chimeric mRNA is produced consisting of the 5' fragment of the lacZ target pre-mRNA and βHCG6 exon 2 is formed which is incapable of coding for an active β-galactosidase. Results from the co-transfection experiments demonstrated that trans-splicing of PTM2 into lacZ target 1 resulted in the reduction of β-galactosidase activity by 10–15% compared to the control.

To further confirm that trans-splicing between the lacZ target pre-mRNA and PTM2 is accurate, RT-PCR was performed using 5' biotinylated lacZ-TR1 and non-biotinylated HCGR2 primers. Single stranded DNA was isolated and sequenced directly using HCGR2 primer (HCG exon 2 specific primer). As evidenced by the sequence of the splice junction, trans-splicing occurred exactly as predicted between the splice sites (FIGS. 12A and 12B), confirming that a conventional pre-mRNA can be invaded by an engineered PTM during splicing, and moreover, that this reaction is precise.

EXAMPLE

Correction of the Cystic Fibrosis Transmembrane Regulator Gene

Cystic fibrosis (CF) is one of the most common genetic diseases in the world. The gene associated with CF has been isolated and its protein product deduced (Kerem, B. S. et al., 1989, Science 245:1073–1080; Riordan et al., 1989, Science 245:1066–1073;Rommans, et al., 1989, Science 245:1059–1065). The protein product of the CF associated gene is referred to as the cystic fibrosis trans-membrane conductance regulator (CFTR). The most common disease-causing mutation which accounts for ~70% of all mutant alleles is a deletion of three nucleotides in exon 10 that encode for a phenylalanine at position 508 (ΔF508). The following section describes the successful repair of the cystic fibrosis gene using spliceosome mediated trans-splicing and demonstrates the feasibility of repairing CFTR in a model system.

Materials and Methods

Pre-Trans Splicing Molecule

The CFTR pre-trans-splicing molecule (PTM) consists of a 23 nucleotide binding domain complimentary to CFTR an AG dinucleotide at the 3' splice site immediately upstream of the sequence encoding CFTR exon 10 (wild type sequence containing F508). This initial PTM was designed for maximal activity in order to demonstrate trans-splicing; therefore the PTM included a UACUAAC yeast consensus BP sequence and an extensive PPT. An 18 nucleotide HIS tag (6 histamine codons) was included after wild type exon 10 coding sequence to allow specific amplification and isolation of the trans-spliced products and not the endogenous CFTR. The oligonucleotides used to generate the two fragments included unique restriction sites. (ApaI and PstI, and PstI and NotI, respectively) to facilitate directed cloning of amplified DNA into the mammalian expression vector pcDNA3.1.

The Target CFTR Pre-mRNA Mini-Gene

Figure 16:
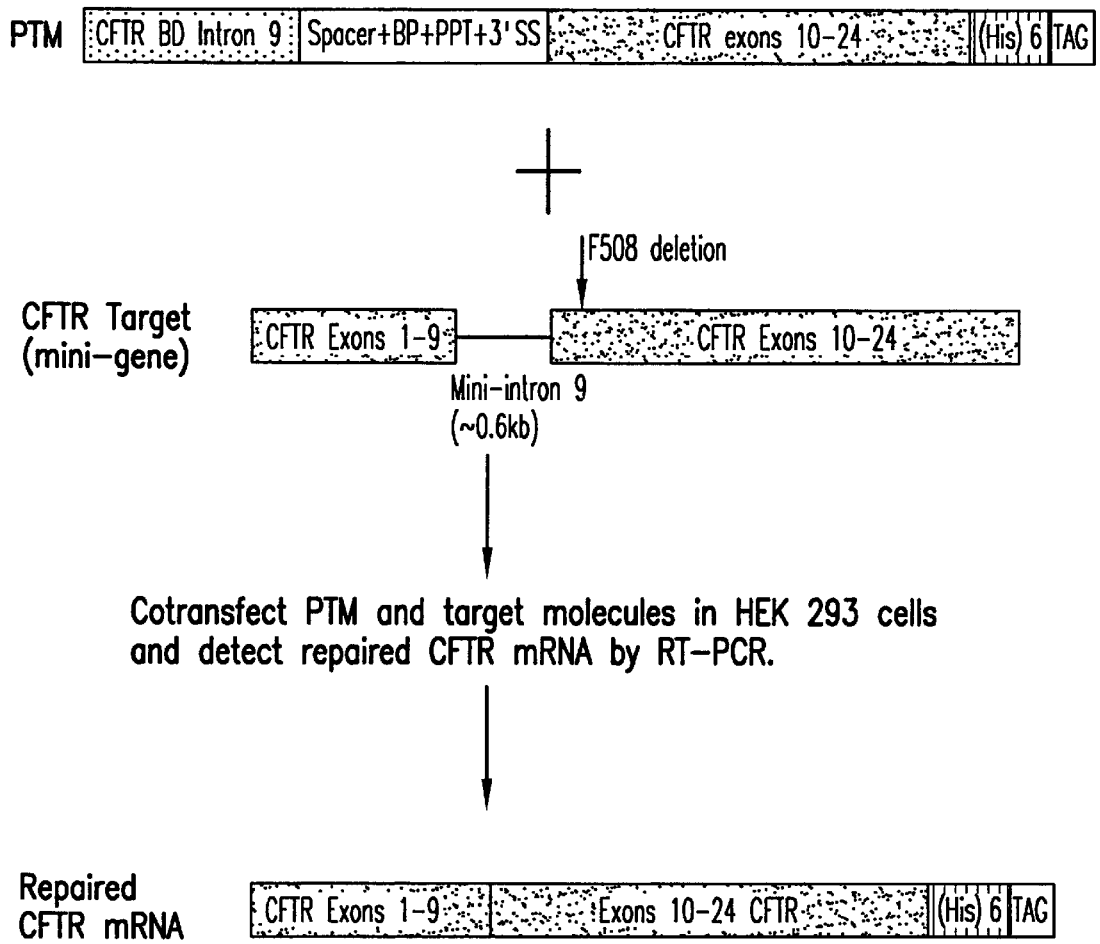
Figure 17:
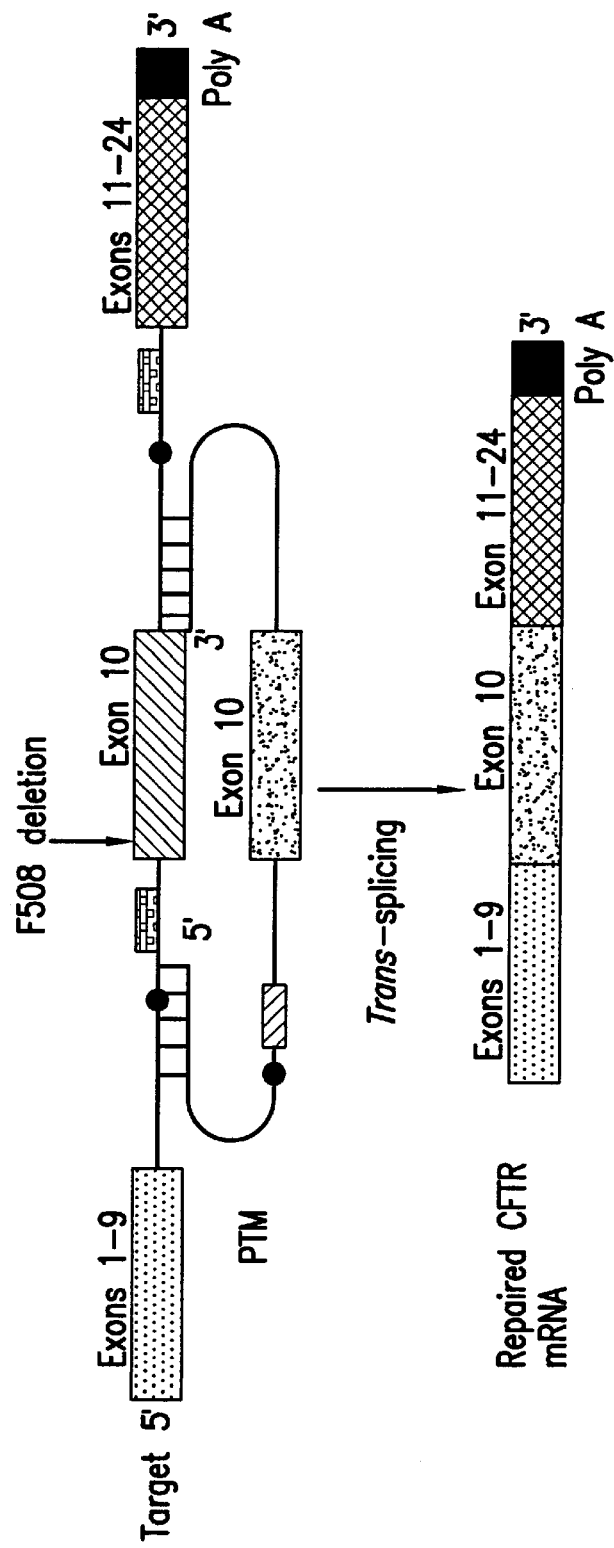

The CFTR mini-gene target is shown in FIG. 13 and consists of CFTR exon 9; the functional 5' and 3' regions of intron 9 (260 and 265 nucleotides from each end, respectively); exon 10 [ΔF508]; and the 5' region of intron 10 (96 nucleotides). In addition, as depicted in FIG. 16, a mini-target gene comprising CFTR exons 1–9 and 10–24 can be used to test the use of spliceosome mediated trans-splicing for correction of the cystic fibrosis mutation. FIG. 17, shows a double splicing PTM that may also be used for correction of the cystic fibrosis mutation. As shown, the double splicing PTM contains CFTR BD intron 9, a spacer, a branch point, a polypyrimidine tract, a 3' splice site, CFTR exon 10, a spacer, a branch point, a polypyrimidine tract, a 5' splice site and CFTR BD exon 10.

Oligonucleotides

The following oligonucleotides were used to create CFTR PTM:

```
Forward CF3
        ACCT GGGCCC ACC CAT TAT TAG GTC ATT AT CCGCGG AAC ATT ATA      SEQ ID NO:40
             ApaI site.  Intron 9 CFTR, -12 to -34.

Reverse CF4
        ACCT CTGCAGGTGACC CTG CAG GAA AAA AAA GAA G                    SEQ ID NO:41
             PstI. BstEI.   PPT.

Forward CF5
        ACCT CTGCAG ACT TCA CTT CTA ATG ATG AT                         SEQ ID NO:42
             PstI.  Exon 10 CFTR, +1 to +24

Reverse CF6
        ACCT GCGGCCGC CTA ATG ATG ATG ATG ATG ATG CTC TTC TAG TTG      SEQ ID NO:43
             GCA TGC
             Not I.    Stop Polyhistamine tag      Exon 10 CFTR,
             +15 to +132
``` intron 9 (3' end, −13 to −31), a 30 nucleotide spacer region (to allow efficient binding of spliceosomal components), branch point (BP) sequence, polypyrimidine tract (PPT) and The following nucleotides were used to create the CFTR TARGET pre-mRNA mini gene (Exon 9+mini-Intron 9+Exon 10+5' end Intron 10):

```
Forward CF18
        GACCT CTCGAG GGA TTT GGG GAA TTA TTT GAG    SEQ ID NO:44
              XhoI   Exon 9 CFTR, 1 to 21.

Reverse CF19
        CTGACCT GCGGCCGC TAC AGT GTT GAA GTG TGT GGT SEQ ID NO:45
        GC
               NotI.    Intron 9 5'end.

Forward CF20
        CTGACCT GCGGCCGC CCA ACT ATC TGA ATC ATG TG  SEQ ID NO:46
               NotI.    Intron 9 3'end.
```

The following oligonucleotides were used for detection of trans-spliced products:

```
Reverse Bio-His
        CTA ATG ATG ATG ATG ATG                     SEQ ID NO:48
        Stop. Polyhistidine tag (5'biotin label).

Reverse Bio-His(2)
        CGC CTA ATG ATG ATG ATG ATG                 SEQ ID NO:49
        3'UT Stop. Polyhistidine tag (5'biotin label).

Forward CF8
        CTT CTT GT ACT CCT GTC CTG                  SEQ ID NO:50
        Exon 9 CFTR.

Forward CF18
        GACCT CTCGAG GGA TTT GGG GAA TTA TTT GAG    SEQ ID NO:51
              Xhol. Exon 9 CFTR.

Reverse CF28
        AAC TAG AAG GCA CAG TCG AGG                 SEQ ID NO:52
        Pc3.1 vector sequence (present in PTM 3'UT but not target).
```

Results

Figure 14:
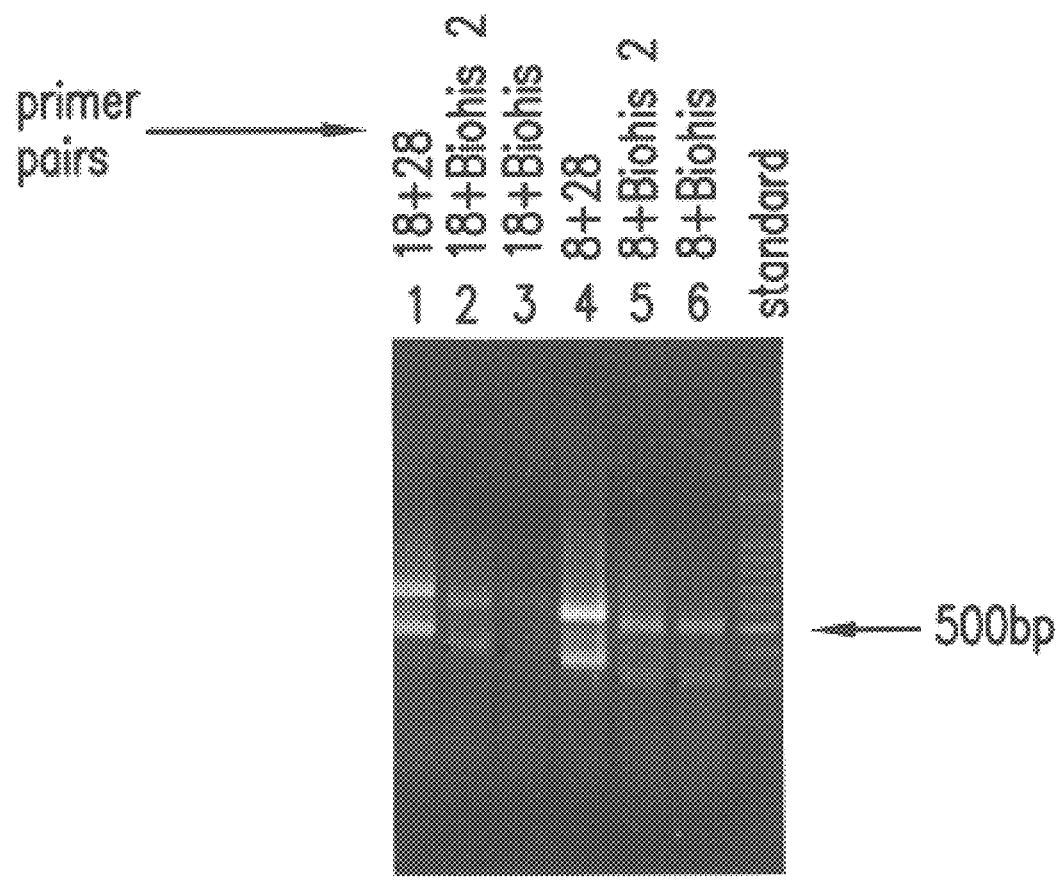

The PTM and target pre-mRNA were co-transfected in 293 embryonic kidney cells using lipofectamine (Life Technologies, Gaithersburg, Md.). Cells were harvested 24 h post transfection and RNA was isolated. Using PTM and target-specific primers in RT-PCR reactions, a trans-spliced product was detected in which mutant exon 10 of the target pre-mRNA was replaced by the wild type exon 10 of the PTM (FIG. 14). Sequence analysis of the trans-spliced product confirmed the restoration of the three nucleotide deletion and that splicing was accurate, occurring at the predicted splice sites (FIG. 15), demonstrating for the first time RNA repair of the cystic fibrosis gene, CFTR.

The present invention is not to be limited in scope by the specific embodiments described herein. Indeed, various modifications of the invention in addition to those described herein will become apparent to those skilled in the art from the foregoing description and accompanying Figures. Such modifications are intended to fall within the scope of the appended claims. Various references are cited herein, the disclosure of which are incorporated by reference in their entireties.

We claim:

1. A cell comprising a nucleic acid molecule wherein said nucleic acid molecule comprises:
   a) one or more target binding domains that target binding of the nucleic acid molecule to a cystic fibrosis trans-membrane conductance regulator pre-mRNA expressed within the cell;
   b) a 3' splice region comprising a branch point, a pyrimidine tract and a 3' splice acceptor site;
   c) a spacer region that separates the 3' splice region from the target binding domain; and
   d) a nucleotide sequence to be trans-spliced to the target pre-mRNA;
wherein said nucleic acid molecule is recognized by nuclear splicing components within the cell.

2. A cell comprising a nucleic acid molecule wherein said nucleic acid molecule comprises:
   a) one or more target binding domains that target binding of the nucleic acid molecule to a cystic fibrosis trans-membrane conductance regulator pre-mRNA expressed within the cell;
   b) a 3' splice acceptor site;
   c) a spacer region that separates the 3' splice region from the target binding domain; and
   d) a nucleotide sequence to be trans-spliced to the target pre-mRNA;
wherein said nucleic acid molecule is recognized by nuclear splicing components within the cell.

3. A cell comprising a nucleic acid molecule wherein said nucleic acid molecule comprises:
   a) one or more target binding domains that target binding of the nucleic acid molecule to a cystic fibrosis trans-membrane conductance regulator pre-mRNA expressed within the cell;
   b) a 5' splice site;
   c) a spacer region that separates the 5' splice site from the target binding domain; and
   d) a nucleotide sequence to be trans-spliced to the target pre-mRNA;
wherein said nucleic acid molecule is recognized by nuclear splicing components within the cell.

4. The cell of claim 1 wherein the nucleic acid molecule further comprises a 5' donor site.

5. The cell of claim 1 wherein the nucleic acid molecule further comprises a safety nucleotide sequence comprising one or more complementary sequences that bind to one or more sides of the 3' splice region.

6. The cell of claim 1 wherein the binding of the nucleic acid molecule to the target pre-mRNA is mediated by complementary base pairing, triple helix formation, or protein-nucleic acid interaction.

7. The cell of claim 1 wherein the nucleotide sequence to be trans-spliced to the target pre mRNA encodes a translatable cystic fibrosis trans-membrane conductance regulator polypeptide.

8. The cell of claim 1 wherein the nucleotide sequence to be trans-spliced to the target pre-mRNA encodes exon 10 of the cystic fibrosis trans-membrane conductance regulator protein.

9. A cell comprising a recombinant vector wherein said vector expresses a nucleic acid molecule comprising:
   a) one or more target binding domains that target binding of the nucleic acid molecule to a cystic fibrosis trans-membrane conductance regulator pre-mRNA expressed within the cell;
   b) a 3' splice region comprising a branch point, a pyrimidine tract and a 3' splice acceptor site;
   c) a spacer region that separates the 3' splice region from the target binding domain; and
   d) a nucleotide sequence to be trans-spliced to the target pre-mRNA;

wherein said nucleic acid molecule is recognized by nuclear splicing components within the cell.

10. A cell comprising a recombinant vector wherein said vector expresses a nucleic acid molecule comprising:
   a) one or more target binding domains that target binding of the nucleic acid molecule to a cystic fibrosis trans-membrane conductance regulator pre-mRNA expressed within the cell;
   b) a 3' splice acceptor site;
   c) a spacer region that separates the 3' splice region from the target binding domain; and
   d) a nucleotide sequence to be trans-spliced to the target pre-mRNA;
wherein said nucleic acid molecule is recognized by nuclear splicing components within the cell.

11. A cell comprising a recombinant vector wherein said vector expresses a nucleic acid molecule comprising:
   a) one or more target binding domains that target binding of the nucleic acid molecule to a cystic fibrosis trans-membrane membrane conductance regulator pre-mRNA expressed within the cell;
   b) a 5' splice site;
   c) a spacer region that separates the 5' splice site from the target binding domain; and
   d) a nucleotide sequence to be trans-spliced to the target pre-mRNA;
wherein said nucleic acid molecule is recognized by nuclear splicing components within the cell.

12. The cell of claim 9 wherein the nucleic acid molecule further comprises a 5' donor site.

13. A method of producing a chimeric RNA molecule in a cell comprising:
   contacting a target pre-mRNA expressed in the cell with a nucleic acid molecule recognized by nuclear splicing components wherein said nucleic acid molecule comprises:
      a) one or more target binding domains that target binding of the nucleic acid molecule to a cystic fibrosis trans-membrane conductance regulator pre-mRNA expressed within the cell;
      b) a 3' splice region comprising a branch point, a pyrimidine tract and a 3' splice acceptor site;
      c) a spacer region that separates the 3' splice region from the target binding domain; and
      d) a nucleotide sequence to be trans-spliced to the target pre-mRNA;
   under conditions in which a portion of the nucleic acid molecule is trans-spliced to a portion of the target pre-mRNA to form a chimeric RNA within the cell.

14. A method of producing a chimeric RNA molecule in a cell comprising:
   contacting a target pre-mRNA expressed in the cell with a nucleic acid molecule recognized by nuclear splicing components wherein said nucleic acid molecule comprises:
      a) one or more target binding domains that target binding of the nucleic acid molecule to a cystic fibrosis trans-membrane conductance regulator pre-mRNA expressed within the cell;
      b) a 3' splice acceptor site;
      c) a spacer region that separates the 3' splice region from the target binding domain; and
      d) a nucleotide sequence to be trans-spliced to the target pre-mRNA;
   under conditions in which a portion of the nucleic acid molecule is trans-spliced to a portion of the target pre-mRNA to form a chimeric RNA within the cell.

15. A method of producing a chimeric RNA molecule in a cell comprising: contacting a target pre-mRNA expressed within the cell with a nucleic acid molecule recognized by nuclear splicing components wherein said nucleic acid molecule comprises:
   a) one or more target binding domains that target binding of the nucleic acid molecule to a cystic fibrosis trans-membrane conductance regulator pre-mRNA expressed within the cell;
   b) a 5' splice site;
   c) a spacer region that separates the 5' splice site from the target binding domain; and
   d) a nucleotide sequence to be tran-spliced to the targer pre-mRNA;
wherein a chimeric RNA molecule is produced within the cell.

16. A method of claim 13 wherein the nucleic acid molecule further comprises a 5' donor site.

17. The method of claim 13, wherein the chimeric RNA molecule comprises sequences encoding a translatable protein.

18. A nucleic acid molecule comprising:
   a) one or more target binding domains that target binding of the nucleic acid molecule to a cystic fibrosis trans-membrane conductance regulator pre-mRNA expressed within a cell;
   b) a 3' splice region comprising a branch point, a pyrimidine tract and a 3' splice acceptor site;
   c) a spacer region that separates the 3' splice region from the target binding domain;
   d) a safety sequence comprising one or more complementary sequences that bind to one or both sides of the 3' splice site; and
   e) a nucleotide sequence to be trans-spliced to the target pre-mRNA;
wherein said nucleic acid molecule is recognized by nuclear splicing components within the cell.

19. A nucleic acid molecule comprising:
   a) one or more target binding domains that target binding of the nucleic acid molecule to a cystic fibrosis trans-membrane conductance regulator pre-mRNA expressed within a cell;
   b) a 3' splice acceptor site;
   c) a spacer region that separates the 3' splice region from the target binding domain;
   d) a safety sequence comprising one or more complementary sequences that bind to one or both sides of the 3' splice site; and
   e) a nucleotide sequence to be trans-spliced to the target pre-mRNA;
wherein said nucleic acid molecule is recognized by nuclear splicing components within the cell.

20. A nucleic acid molecule comprising:
   a) one or more target binding domains that target binding of the nucleic acid molecule to a cystic fibrosis trans-membrane conductance regulator pre-mRNA expressed within a cell;
   b) a 5' splice site;
   c) a spacer region that separates the 5' splice site from the target binding domain;
   d) a safety sequence comprising one or more complementary sequences that bind to one or both sides of the 5' splice site; and
   e) a nucleotide sequence to be trans-spliced to the target pre-mRNA;

wherein said nucleic acid molecule is recognized by nuclear splicing components within the cell.

21. The nucleic acid molecule of claim 18 wherein the nucleic acid molecule further comprises a 5' donor site.

22. The nucleic acid molecule of claim 18 wherein the binding of the nucleic acid molecule to the target pre-mRNA is mediated by complementary base pairing, triple helix formation, or protein-nucleic acid interaction.

23. The nucleic acid molecule of claim 18 wherein the nucleotide sequences to be trans-spliced to the target pre-mRNA encode a translatable cystic fibrosis trans-membrane conductance regulator polypeptide.

24. The nucleic acid molecule of claim 18 wherein the nucleotide sequence to be trans-spliced to the target pre-mRNA encodes exon 10 of the cystic fibrosis trans-membrane conductance regulator protein.

25. The nucleic acid molecule of claim 20 wherein the binding of the nucleic acid molecule to the target pre-mRNA is mediated by complementary base pairing, triple helix formation, or protein-nucleic acid interaction.

26. The nucleic acid molecule of claim 20 wherein the nucleotide sequence to be trans-spliced to the target pre-mRNA encodes a translatable cystic fibrosis trans-membrane conductance polypeptide.

27. The nucleic acid molecule of claim 20 wherein the nucleotide sequence to be trans-spliced to the target pre-mRNA encodes exon 10 of the cystic fibrosis trans-membrane conductance regulator protein.

28. A eukaryotic expression vector wherein said vector expresses a nucleic acid molecule comprising:
   a) one or more target binding domains that target binding of the nucleic acid molecule to a cystic fibrosis trans-membrane conductance protein pre-mRNA expressed within a cell;
   b) a 3' splice region comprising a branch point, a pyrimidine tract and a 3' splice acceptor site;
   c) a spacer region that separates the 3' splice region from the target binding domain; and
   d) a nucleotide sequence to be trans-spliced to the target pre-mRNA;

wherein said nucleic acid molecule is recognized by nuclear splicing components within the cell.

29. A eukaryotic expression vector wherein said vector expresses a nucleic acid molecule comprising:
   a) one or more target binding domains that target binding of the nucleic acid molecule to a cystic fibrosis trans-membrane conductance protein pre-mRNA expressed within a cell;
   b) a 3' splice acceptor site;
   c) a spacer region that separates the 3' splice region from the target binding domain; and
   d) a nucleotide sequence to be trans-spliced to the target pre-mRNA;

wherein said nucleic acid molecule is recognized by nuclear splicing components within the cell.

30. A eukaryotic expression vector wherein said vector expresses a nucleic acid molecule comprising:
   a) one or more target binding domains that target binding of the nucleic acid molecule to a cystic fibrosis trans-membrane conductance protein pre-mRNA expressed within a cell;
   b) a 5' splice site;
   c) a spacer region that separates the 5' splice site from the target binding domain; and
   d) a nucleotide sequence to be trans-spliced to the target pre-mRNA;

wherein said nucleic acid molecule is recognized by nuclear splicing components within the cell.

31. The vector of claim 28 wherein the nucleic acid nolecule further 5' donor site.

32. A composition comprising a physiologically acceptable carrier and a nucleic molecule according to any claims 28–31.

* * * * *